US012329539B2

(12) United States Patent
Han et al.

(10) Patent No.: US 12,329,539 B2
(45) Date of Patent: Jun. 17, 2025

(54) NON-INVASIVE SKIN SENSOR FOR LONG-TERM MONITORING AND METHOD FOR FABRICATING THE SAME

(71) Applicants: AMOREPACIFIC CORPORATION, Seoul (KR); MASSACHUSETTS INSTITUTE OF TECHNOLOGY, Cambridge, MA (US)

(72) Inventors: Jiyeon Han, Yongin-si (KR); Eunjoo Kim, Yongin-si (KR); Yeongin Kim, Cambridge, MA (US); Jeehwan Kim, Cambridge, MA (US); Hanwool Yeun, Cambridge, MA (US)

(73) Assignees: AMOREPACIFIC CORPORATION, Seoul (KR); MASSACHUSETTS INSTITUTE OF TECHNOLOGY

( * ) Notice: Subject to any disclaimer, the term of this patent is extended or adjusted under 35 U.S.C. 154(b) by 689 days.

(21) Appl. No.: 17/669,920

(22) Filed: Feb. 11, 2022

(65) Prior Publication Data
US 2022/0354428 A1 Nov. 10, 2022

Related U.S. Application Data

(60) Provisional application No. 63/185,513, filed on May 7, 2021.

(51) Int. Cl.
*A61B 5/00* (2006.01)
*A61B 5/01* (2006.01)
*A61B 5/0537* (2021.01)

(52) U.S. Cl.
CPC ............. *A61B 5/6833* (2013.01); *A61B 5/01* (2013.01); *A61B 5/0537* (2013.01); *A61B 5/443* (2013.01); *A61B 2560/0242* (2013.01); *A61B 2562/0261* (2013.01); *A61B 2562/06* (2013.01); *A61B 2562/164* (2013.01)

(58) Field of Classification Search
CPC ............. A61B 5/6833; A61B 2562/06; A61B 2562/164
See application file for complete search history.

(56) References Cited

U.S. PATENT DOCUMENTS

| | | | | |
|---|---|---|---|---|
| 2015/0351689 A1* | 12/2015 | Adams | ................. | A61B 5/6833 600/300 |
| 2020/0111815 A1* | 4/2020 | Lius | ...................... | G06F 3/0412 |
| 2020/0187848 A1* | 6/2020 | Han | ...................... | H10N 30/073 |
| 2021/0175283 A1* | 6/2021 | Wang | ...................... | H01L 25/50 |

OTHER PUBLICATIONS

Kim, D. H. et al., "Epidermal Electronics", Science, vol. 333, 2011, pp. 838-843 (8 pages total).

(Continued)

*Primary Examiner* — Daniel L Cerioni
(74) *Attorney, Agent, or Firm* — Sughrue Mion, PLLC

(57) ABSTRACT

Embodiments relate to a non-invasive electronic device including at least one sensing unit capable of accurately monitoring a user's health condition for a long time such as a few weeks without malfunction while it is worn on the wearer's skin in a non-invasive manner and a method for fabricating the non-invasive electronic device. The non-invasive electronic device includes for example, a skin sensor device.

17 Claims, 42 Drawing Sheets

(56) References Cited

OTHER PUBLICATIONS

Chu. Bryant et al., "Bring on the bodyNET", Nature, 2017, vol. 549, pp. 328-330 (3 pages total).

Xu, S. et al., "Skin sensors are the future of health care", Nature, 2019, vol. 571, pp. 319-321 (3 pages total).

Someya, T. et al., "Toward a new generation of smart skins", Nat. Biotechnol., 2019, vol. 37, pp. 382-388 (7 pages total).

Rogers, J. A. et al., "Materials and Mechanics for Stretchable Electronics", Science, 2010, vol. 327, pp. 1603-1607 (6 pages total).

Webb, R. C. et al., "Ultrathin conformal devices for precise and continuous thermal characterization of human skin", Nat. Mater., 2013, vol. 12, pp. 938-944 (8 pages total).

Kim, D.-H. et al., "Stretchable and Foldable Silicon Integrated Circuits", Science, 2008, vol. 320, pp. 507-511 (6 pages total).

Kim, J. et al., "Stretchable silicon nanoribbon electronics for skin prosthesis", Nat. Commun., 2014, vol. 5, No. 5747, ncomms6747 (11 pages total).

Sim, K. et al., "Metal oxide semiconductor nanomembrane-based soft unnoticeable multifunctional electronics for wearable human-machine interfaces", Sci. Adv., 2019, vol. 5, eaav9653 (11 pages total).

Jang, K. I. et al., "Rugged and breathable forms of stretchable electronics with adherent composite substrates for transcutaneous monitoring", Nat. Commun., 2014, vol. 5, No. 4779, ncomms5779 (10 pages total).

Choi, M. K. et al., "Cephalopod-Inspired Miniaturized Suction Cups for Smart Medical Skin", Adv. Healthcare Mater., 2016, vol. 5, pp. 80-87 (8 pages total).

Tian, L. et al., "Large-area MRI-compatible epidermal electronic interfaces for prosthetic control and cognitive monitoring", Nat. Biomed. Eng., 2019, vol. 3, pp. 194-205 (16 pages total).

Ray, T. et al., "Soft, skin-interfaced wearable systems for sports science and analytics", Curr. Opin. Biomed. Eng., 2019, vol. 9, pp. 47-56 (10 pages total).

Gambhir, S. S. et al., "Toward achieving precision health", Sci. Transl. Med., 2018, vol. 10, eaao3612 (6 pages total).

Son, D.et al., "Multifunctional wearable devices for diagnosis and therapy of movement disorders", Nat. Nanotechnol., 2014, vol. 9, pp. 397-404 (8 pages total).

Chung, H. U. et al., "Binodal, wireless epidermal electronic systems with in-sensor analytics for neonatal intensive care", Science, 2019, vol. 363, eaau0780, pp. 1-12 (14 pages total).

Miyamoto, A. et al., "Inflammation-free, gas-permeable, lightweight, stretchable on-skin electronics with nanomeshes", Nat. Nanotechnol., 2017, vol. 12, pp. 907-913 (8 pages total).

Peng, X. et al., "A breathable, biodegradable, antibacterial, and self-powered electronic skin based on all-nanofiber triboelectric nanogenerators", Sci. Adv., 2020, vol. 6, eaba9624 (11 pages total).

Rogers, J. A. et al., "Synthesis, assembly and applications of semiconductor nanomembranes", Nature, 2011, vol. 477, pp. 45-53 (9 pages total).

Yu, K. J. et al., "Inorganic semiconducting materials for flexible and stretchable electronics", npj Flex. Electron., 2017, vol. 1 (14 pages total).

Cho, Y. et al., "Engineering the shape and structure of materials by fractal cut", Proc. Natl. Acad. Sci., 2014, vol. 111, No. 49, pp. 17390-17395 (6 pages total).

Kim, K. B. et al., "Extremely Versatile Deformability beyond Materiality: A New Material Platform through Simple Cutting for Rugged Batteries", Adv. Eng. Mater., 2019, vol. 21, 1900206 (8 pages total).

Kim, B. J. et al., "Fatigue-Free, Electrically Reliable Copper Electrode with Nanohole Array", Small, 2012, vol. 8, pp. 3300-3306 (7 pages total).

Jang, K. I. et al., "Soft network composite materials with deterministic and bio-inspired designs", Nat. Commun., 2015, vol. 6, No. 6566, ncomms7566 (11 pages total).

Ma, Y. et al., "Design and application of 'J-shaped' stress-strain behavior in stretchable electronics: a review", Lab Chip, 2017, vol. 17, pp. 1689-1704 (16 pages total).

Lamberti, A. et al., "PDMS membranes with tunable gas permeability for microfluidic applications", RSC Adv., 2014, vol. 4, pp. 61415-61419 (5 pages total).

Beker, L. et al., "A bioinspired stretchable membrane-based compliance sensor", Proc. Natl. Acad. Sci., 2020, vol. 117, No. 21, pp. 11314-11320 (7 pages total).

Petersen, L. J. et al., "A novel model of inflammatory pain in human skin involving topical application of sodium lauryl sulfate" Inflamm. Res., 2010, vol. 59, pp. 775-781(7 pages total).

Kim, Y. et al., "Remote epitaxy through graphene enables two-dimensional material-based layer transfer", Nature, 2017, vol. 544, pp. 340-343 (12 pages total).

Kong, W. et al., "Polarity governs atomic interaction through two-dimensional materials", Nat. Mater., 2018, vol. 17, pp. 999-1004 (7 pages total).

Bae, S. H. et al., "Graphene-assisted spontaneous relaxation towards dislocation-free heteroepitaxy", Nat. Nanotechnol., 2020, vol. 15, pp. 272-276 (6 pages total).

Kum, H. S. et al., "Heterogeneous integration of single crystalline complex-oxide membranes", Nature, 2020, vol. 578, pp. 75-81 (19 pages total).

Lee, Y. Y. et al., "Stretching-Induced Growth of PEDOT-Rich Cores: A New Mechanism for Strain-Dependent Resistivity Change in PEDOT:PSS Films", Adv. Funct. Mater., 2013, vol. 23, pp. 4020-4027 (8 pages total).

Kim, B. J. et al., "Crack nucleation during mechanical fatigue in thin metal films on flexible substrates", Acta Mater., 2013, vol. 61, pp. 3473-3481 (9 pages total).

Seo, J. et al., "Direct Graphene Transfer Printing Using Mechanically Controlled, Large Area and Its Application to Transfer Graphene/Copper Freestanding Layer", Adv. Funct. Mater., 2018, vol. 28, 1707102 (9 pages total).

* cited by examiner

NON-INVASIVE SKIN SENSOR FOR LONG-TERM MONITORING AND METHOD FOR FABRICATING THE SAME

CROSS-REFERENCE TO RELATED APPLICATION

This application claims priority to U.S. patent application Ser. No. 63/185,513, filed on May 7, 2021, and all the benefits accruing therefrom under 35 U.S.C. § 119, the contents of which in its entirety are herein incorporated by reference.

TECHNICAL FIELD

Embodiments of the present disclosure relate to a non-invasive electronic device, and more particularly, to a non-invasive electronic device with improved interface capable of preventing the accumulation of skin waste products and having high adhesion to skin and a method for fabricating the same.

BACKGROUND ART

Electronic skins (e-skins), which are electronic sensors mechanically affecting human skin, have been long developed as an ideal electronic platform for non-invasive human health monitoring irrespective of time and space. To achieve reliable health monitoring, interface between e-skin and skin needs to be compliant and invulnerable to damage. Non-patent Literature 1 (Rogers, J. A., Someya, T. & Huang, Y. Materials and mechanics for stretchable electronics. Science (80-.). 327, 1603-1607 (2010)) and Non-patent Literature 2 (Webb, R. C. et al. Ultrathin conformal devices for precise and continuous thermal characterization of human skin. Nat. Mater. 12, 938-944 (2013)) disclose electronic skins. However, the existing e-skins cannot perfectly permeate skin waste products, and thus the intimate interface degrades over time, which impedes accurate long-term health monitoring related to normal daily activities. Moreover, a high-performance single crystal semiconductor device is not embedded into an e-skin platform due to a thick and rigid substrate.

DISCLOSURE

Technical Problem

According to an aspect of the present disclosure, it is provided an electronic module for monitoring a user's skin condition.

Additionally, according to another aspect of the present disclosure, it is directed to providing a non-invasive electronic device for long-term monitoring, including the electronic module.

Besides, it is directed to providing a method for fabricating the electronic module or the non-invasive electronic device.

Technical Solution

An electronic module for monitoring a user's skin condition according to an aspect of the present disclosure may comprise a first passivation layer closer to the skin; an electronic circuit unit built on the first passivation layer, and including interconnects made of a conductive material and at least one sensing unit including a semiconductor property material, the sensing unit including at least one type of sensing unit of one or more of temperature sensing units; one or more of hydration sensing unit; one or more phot sensing units or one or more of strain sensing units; and a second passivation layer formed on the electronic circuit unit. Here, each of the first passivation layer, the electronic circuit unit and the second passivation layer includes a plurality of through-holes, and at least some of the plurality of through-holes of each of the first passivation layer, the electronic circuit unit and the second passivation layer form a hole pattern. Each of the hole pattern of the first passivation layer, the hole pattern of the electronic circuit unit and the hole pattern the second passivation layer has a planar pattern corresponding to each other to form an open channel when the first passivation layer, the electronic circuit unit and the second passivation layer are stacked.

In an embodiment, each of the plurality of through-holes may include each hole pattern formed by a plurality of dumbbell holes, each dumbbell hole is configured to connect between circular parts at two ends, and the plurality of dumbbell holes is arranged in an interdigitated array with respect to adjacent other dumbbell holes such that a circular part is adjacent to an extended part of the adjacent other dumbbell hole.

In an embodiment, each hole pattern may further include each of a plurality of circular holes, and each circular hole is formed in each sub region surrounded by the dumbbell holes arranged in the interdigitated array.

In an embodiment, some of the hole pattern of the first passivation layer, the hole pattern of the electronic circuit unit and the hole pattern of the second passivation layer may have respective specifications that are different from some other hole patterns.

In an embodiment, the temperature sensing unit may include a temperature responsive layer connected to the adjacent interconnect. Here, the temperature responsive layer generates an electric current in response to temperature, and the temperature responsive layer is connected to be positioned on a same plane as the adjacent interconnect.

In an embodiment, the temperature responsive layer may include a hole pattern formed by a plurality of through-holes, partially corresponding to the hole pattern of the first passivation layer and the hole pattern of the second passivation layer.

In an embodiment, the hydration sensing unit may include a plurality of electrodes connected to the adjacent interconnect—the plurality of electrodes including at least one first electrode and at least one second electrode; and a hydration responsive layer formed on a surface of the electrode. Each of the plurality of electrodes and the hydration responsive layer includes a plurality of through-holes that form an open channel when stacked upon each other. The through-holes of the electrodes and the through-holes of the hydration responsive layer have a planar shape corresponding to a planar shape of the through-holes of the first passivation layer and the second passivation layer at least in part.

In an embodiment, the hydration sensing unit may have a cantilever structure such that the first electrode of the hydration sensing unit extends from the interconnect of a first side, and the second electrode of the hydration sensing unit extends from the interconnect of a second side, and the extended parts of the at least one first electrode and the at least one second electrode are arranged in an interdigitated array.

In an embodiment, the photo sensing unit may include a photo responsive layer having two ends positioned on a surface of the adjacent interconnect, wherein the photo responsive layer generates an electric current in response to light irradiation, and the photo responsive layer generates the electric current when a specific band of light is irradiated, or generates the changed electric current when an intensity of the irradiated light changes.

In an embodiment, a part of the second passivation layer formed at a sensing area of the photo sensing unit may further include at least one auxiliary through-hole.

In an embodiment, the photo sensing unit may further include a capping layer formed at an interface between the part of the second passivation layer having the auxiliary through-hole and the photo sensing unit.

In an embodiment, the strain sensing unit may include an active layer having two ends positioned on a surface of the adjacent interconnect. Here, the active layer generates an electric current in response to strain of the electronic module.

In an embodiment, the strain sensing unit may further include at least one of a first capping layer formed at an interface between the active layer and the first passivation layer, or a second capping layer formed at an interface between the active layer and the second passivation layer.

In an embodiment, the electronic circuit unit may include a pair of strain sensing units. One of strain sensing units is positioned on the first passivation layer to sense x-axial strain, and the other strain sensing unit is positioned on the first passivation layer to sense y-axial strain.

A non-invasive electronic device according to another aspect of the present disclosure may comprise the electronic module according to the above mentioned embodiments. The non-invasive electronic device may comprise: a skin attachable flexible patch which contacts the first passivation layer, wherein the flexible patch includes a plurality of through-holes, and at least some of the plurality of through-holes of the flexible patch form a hole pattern, and the hole pattern of the flexible patch has a planar pattern corresponding to the hole pattern of the electronic module to form a perforated pattern when stacked with the electronic module.

In an embodiment, the plurality of through-holes of the flexible patch may include at least one specific through-hole that is different from the through-hole of the hole pattern. A size of the specific through-hole is different from a size of the through-hole that forms the hole pattern of the electronic module, and the photo sensing unit and the strain sensing unit are built in the specific through-hole.

In an embodiment, the flexible patch may further include a supporter which extends from one side to the other side in the specific through-hole to support the photo sensing unit.

A method for fabricating a non-invasive electronic device for long-term monitoring of a user's skin condition according to other aspect of the present disclosure may comprise forming a first sacrificial layer on a first substrate; building an electronic module on the first sacrificial layer; and removing the first sacrificial layer to separate the first substrate from the electronic module and bonding to a flexible patch. Here, the step of building the electronic module comprises patterning each layer in the electronic module to form an open channel running between a surface of the electronic module and an opposite surface.

In an embodiment, the step of building the electronic module may comprise forming a first passivation layer on the first sacrificial layer; building an electronic circuit unit on the first passivation layer; forming a second passivation layer on the electronic circuit unit; and patterning the first passivation layer and the second passivation layer stacked such that a plurality of through-holes is formed in the first passivation layer and the second passivation layer. Here, the plurality of through-holes of the first passivation layer and the second passivation layer form hole patterns corresponding to each other.

In an embodiment, building the electronic circuit unit may comprise building at least one sensing unit which senses a change in the skin condition—the sensing unit including at least one of a temperature sensing unit or a hydration sensing unit; and building interconnects connected to the sensing unit. Where building the interconnect comprises forming the interconnect made of a conductive material on the first passivation layer; patterning the interconnect to form a plurality of through-holes; and patterning the temperature sensing unit or the hydration sensing unit to form a plurality of through-holes. Here, the plurality of through-holes of the interconnect form a hole pattern, and the hole pattern of the interconnect partially corresponds to the hole pattern of the first passivation layer and the second passivation layer. The plurality of through-holes of the temperature sensing unit or the plurality of through-holes of the hydration sensing unit form a hole pattern, and the hole pattern of the temperature sensing unit or the hydration sensing unit corresponds to a sub pattern of the hole pattern of the first passivation layer and the second passivation layer at least in part. The sub pattern of the hole pattern of the first passivation layer and the second passivation layer is a pattern formed in a region that is different from a region corresponding to the hole pattern of the interconnect in the hole pattern of the first passivation layer and the second passivation layer.

In an embodiment, the first sacrificial layer may be removed through an electrochemical etching process. The separated first substrate is reused to fabricate other electronic module.

In an embodiment, the method may further comprise after removing the first sacrificial layer, cleaning off a residue of an etching solution remaining on a module structure from which the first substrate is separated.

In an embodiment, removing the first sacrificial layer and bonding to a flexible patch may include forming a second sacrificial layer on the surface of the electronic module; attaching a transferor onto the second sacrificial layer; and bonding the second sacrificial layer and the electronic module to a surface of the flexible patch through the transferor.

In an embodiment, the flexible patch bonded with the second sacrificial layer and the electronic module may be coated on a mold substrate. The mold substrate has a furrow pattern formed by a plurality of island steps, and each island step has a planar shape that matches each through-hole that forms the hole pattern of the flexible patch. In an embodiment, the bonding may comprise bonding such that each island step of the mold substrate corresponds to each through-hole of the electronic module.

In an embodiment, a size of the through-hole of the hole pattern of the flexible patch may be different from a size of the through-hole of the electronic module.

In an embodiment, bonding the second sacrificial layer and the electronic module to the surface of the flexible patch through the transferor may comprise separating the mold substrate from the flexible patch coated on the mold substrate, bonded with the electronic module through the transferor; separating the transferor in a state that the electronic module is bonded to the flexible patch; and removing the second sacrificial layer after separating the transferor.

In an embodiment, the transferor may be a thermal release tape (TRT). The transfer is detached by heating to being removed from the skin module.

In an embodiment, the second sacrificial layer may be made of a water-insoluble material that is different from the first sacrificial layer. The second sacrificial layer is removed through chemical etching.

In an embodiment, the method may further comprise cleaning off a residue of an etching solution or a surface residue from a structure of the skin sensor device from which the second sacrificial layer is removed.

Advantageous Effects

The electronic device according to an aspect of the present disclosure is noninvasively attached to a user's skin. The electronic device can accurately monitor the wearer's skin condition by at least one sensing unit in the device attached for a long time, for example, a few weeks without malfunction.

DESCRIPTION OF DRAWINGS

The following is a brief introduction to necessary drawings in the description of the embodiments to describe the technical solutions of the embodiments of the present disclosure or the existing technology more clearly. It should be understood that the accompanying drawings are for the purpose of describing the embodiments of the present disclosure and not intended to be limiting of the present disclosure. Additionally, for clarity of description, the accompanying drawings may show some elements to which a variety of modifications such as exaggeration and omission are applied.

BEST MODE

Figure 1:
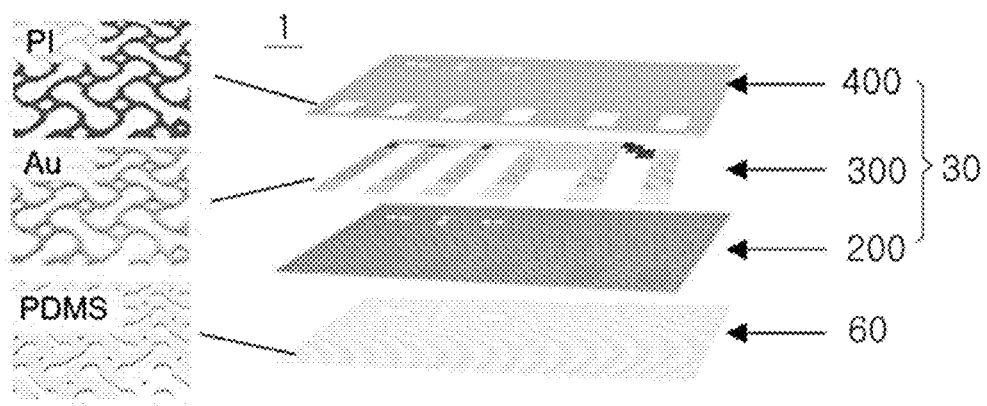
FIG. 1 is an exploded perspective view of a skin sensor device according to an aspect of the present disclosure.

The terms first, second and the like are used to describe a variety of portions, components, regions, layers and/or sections, but not limited thereto. These terms are used to distinguish a portion, component, region, layer or section from another. Accordingly, a first portion, component, region, layer or section described below may be referred to as a second portion, component, region, layer or section without departing from the scope of the present disclosure.

The term describing the relative space such as "below", "on" or the like may be used to describe a relationship of an element to another shown in the drawing more easily. These terms are intended to include the intended meaning in the drawing as well as other meanings or operations of the device in use. For example, when a device in the drawing is inverted, elements described as being "below" other elements are described as being "on" them. Accordingly, the term "below" taken as an example include up and down directions. The device may rotate 90° or at any other angle, and the term describing the relative space is interpreted accordingly.

When an element is referred to as being "on" another element, the element may be on the other element, or intervening elements may be interposed between. In contrast, when an element is referred to as being "directly on" another element, there is no intervening element between them.

As used herein, the singular forms are intended to include the plural forms as well, unless the context clearly indicates otherwise. The term "comprising" when used in this specification, specifies the presence of stated features, regions, integers, steps, operations, elements and/or components, but does not preclude the presence or addition of one or more other features, regions, integers, steps, operations, elements and/or components.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The terms as used herein are provided to refer to specific embodiments, but not intended to limit the present disclosure.

Hereinafter, the embodiments of the present disclosure will be described in detail with reference to the drawings.

A non-invasive electronic device according to embodiments of the present disclosure includes an electronic module 30 that can operate on a user's skin. The electronic device is a non-invasive electronic device that can be attached to the user's skin. In certain embodiments, when the non-invasive electronic device includes at least one sensing unit to sense a change in the condition of the skin to which the electronic module is attached, it can be used as a sensor device (hereinafter, "skin sensor device") attached to the user's skin to monitor the user's skin condition. In the specification, the electronic module including the sensing unit may be referred to as a sensor module.

Hereinafter, the non-invasive electronic device according to the present disclosure is described with regard to the certain embodiments in which the non-invasive electronic device includes the electronic module 30 (hereinafter, "the sensor module 30") including the sensing unit and operates as a skin sensor device, but this is for clarity of description only. It will be clearly understood by those skilled in the art that the embodiments of the present disclosure are not necessarily limited to the embodiments in which the electronic module of the present disclosure includes the sensing unit, or the non-invasive electronic device of the present disclosure is used as the skin sensor device.

Figure 2:
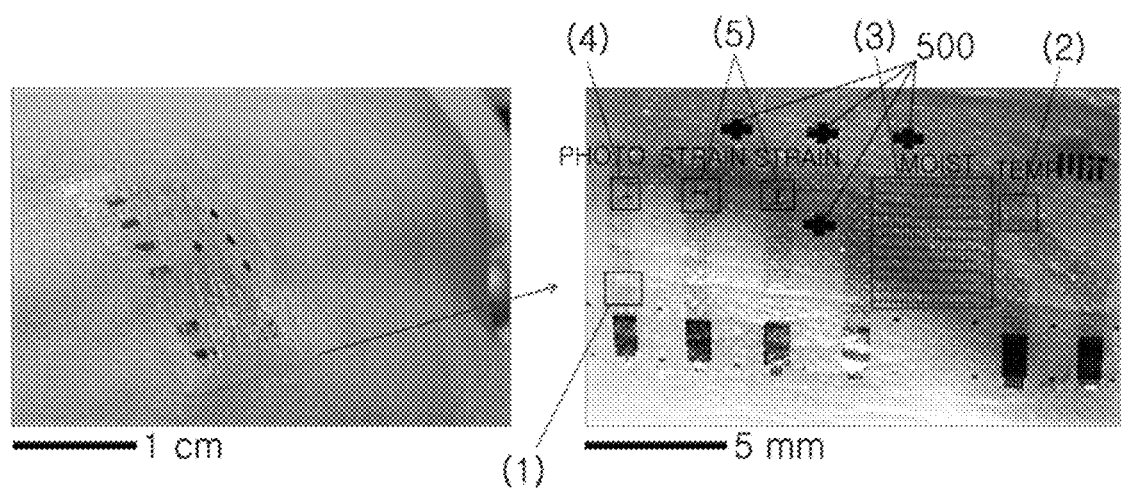
FIG. 2 is an image of the skin sensor device of FIG. 1 attached to a user's skin.

FIG. 1 is an exploded perspective view of a skin sensor device according to an aspect of the present disclosure, and FIG. 2 is an image of the skin sensor device of FIG. 1 attached to a user's skin.

Referring to FIGS. 1 and 2, the skin sensor device 1 includes a sensor module 30 and a flexible patch 60.

The skin sensor device 1 is fixed on the user's skin by the flexible patch 60. The flexible patch 60 supports the sensor module 30 and fixes the position of the sensor module 30 close to the skin.

The flexible patch 60 has a sufficient thickness to support the weight of the sensor module 30. For example, the flexible patch 60 may be 20 um in thickness.

Additionally, the flexible patch 60 comes into contact with the skin to attach the skin sensor device 1 to the skin. The flexible patch 60 is configured such that at least one surface has sufficient viscosity to attach to the skin.

The flexible patch 60 is made of a material with flexibility and adhesion properties. The flexible patch 60 may be made of, for example, a material including polydimethylsioxane (PDMS), but is not limited thereto.

As described above, the flexible patch 60 needs to have adhesion properties, and at the same time, have a supporting structure.

Figure 3:
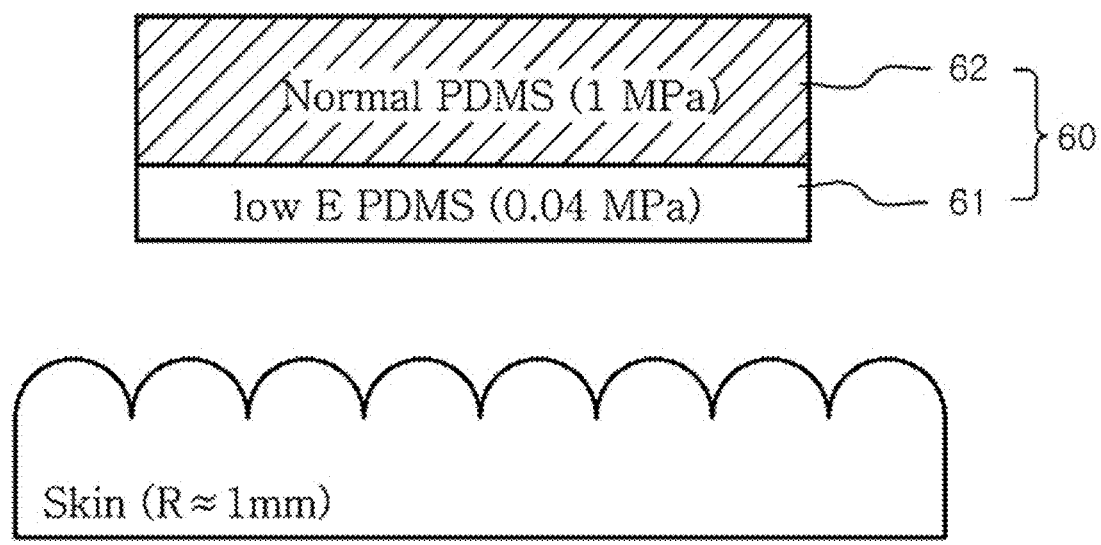
FIG. 3 is a cross-section view of a flexible patch of a bi-layer structure having different rigidity according to an embodiment of the present disclosure.

FIG. 3 is a cross-section view of the flexible patch 60 of a bi-layer structure having different rigidity according to an embodiment of the present disclosure.

Referring to FIG. 3, the flexible patch 60 may have a bi-layer structure including two sub layers (hereinafter, a first flexible layer 61 and a second flexible layer 62) having different rigidity. When rigidity is different, the elastic modulus of each sub layer 61, 62 may be different.

The first flexible layer 61 is a sub layer that contacts the skin, and the flexible patch 60 is attached to the skin by the first flexible layer 61.

The second flexible layer 62 is formed on the first flexible layer 61. The second flexible layer 62 has higher rigidity than the first flexible layer 61 to support the integrated components (for example, the sensor module 30, etc.) on the flexible patch 60 and appropriately control the bending of the flexible patch 60 so as to make handling easier. The second flexible layer 62 having higher rigidity may have lower elastic modulus than the first flexible layer 61, and in turn, has weaker adhesion strength to the skin.

In contrast, the first flexible layer 61 that is attached to the skin is softer than the second flexible layer 62 having weaker adhesion strength to the skin. The first flexible layer 61 has lower flexural rigidity D1 than the flexural rigidity D2 of the second flexible layer 62. For example, the first flexible layer 61 may have lower elastic modulus E1 (for example, 0.04 MPa) to achieve conformal attachment to the skin surface, and the second flexible layer 62 may have higher elastic modulus E2 (for example, 1 MPa).

In an embodiment, the flexible patch 60 may be made of off-stoichiometric PDMS to have higher adhesion strength and lower elastic modulus. The off-stoichiometric PDMS includes a pre-polymer and a curing agent.

The first flexible layer 61 and the second flexible layer 62 may include the pre-polymer and the curing agent. Here, the second flexible layer 62 may be configured to have a higher ratio of the curing agent than the first flexible layer 61.

In an example, the first flexible layer 61 may include the pre-polymer and the curing agent at a 40:1 ratio, and the second flexible layer 62 may include the pre-polymer and the curing agent at a 10:1 ratio. Due to this difference in the ratio of the curing agent, the flexural rigidity D of the first flexible layer 61 and the second flexible layer 62 is differently determined.

Additionally, the flexible patch 60 has a perforated pattern formed by a plurality of through-holes. By the perforated pattern of the flexible patch 60, the skin sensor device 1 has stronger adhesion, higher air permeability and stronger durability. The perforated pattern will be described in more detail below with reference to FIGS. 8 to 12.

The sensor module 30 may include an electronic circuit unit 300; and a first passivation layer 200 and/or a second passivation layer 400. In certain embodiments, the sensor module 30 may include the first passivation layer 200 and the second passivation layer 400 to protect the electronic circuit unit 300.

The passivation layers 200, 400 protect the electronic circuit unit 300 from an external environment by preventing the exposure of the electronic circuit unit 300.

The first passivation layer 200 is a protective layer interposed between the flexible patch 60 and the electronic circuit unit 300. When the skin sensor device 1 is attached to the skin, the first passivation layer 200 is disposed at a lower position than the second passivation layer 400 with respect to the skin surface, so it may be herein referred to as a lower passivation layer. Under this attachment structure, the first passivation layer 200 is positioned below the electronic circuit unit 300.

The first passivation layer 200 prevents the direct contact of the electronic circuit unit 300 with the flexible patch 60. Additionally, the first passivation layer 200 prevents damage of the electronic circuit unit 300 (especially, the lower end of the unit) in the process of fabricating the sensor module 30. For example, as described below with reference to FIG. 29I, the first passivation layer 200 prevents damage of the electronic circuit unit 300 in the process of removing a first sacrificial layer 110.

The second passivation layer 400 is a protective layer positioned on the electronic circuit unit 300. When the skin sensor device 1 is attached to the skin, the second passivation layer 400 is disposed at a higher position than the first passivation layer 200 with respect to the skin surface, so it may be herein referred to as an upper passivation layer. The second passivation layer 400 is formed on the surface of the electronic circuit unit 300 to cover the electronic circuit unit 300 and prevent the exposure of the electronic circuit unit 300. The second passivation layer 400 may have a larger area than the electronic circuit unit 300. The second passivation layer 400 may have a region that covers the electronic circuit unit 300 and other region that does not cover the electronic circuit unit 300 and covers the underlying component (for example, the first passivation layer 200).

Additionally, the second passivation layer 400 not only prevents the exposure of the electronic circuit unit 300 but also keeps the position of the electronic circuit unit 300 near a Nature Machine Plane (NMP) of the skin sensor device 1. Accordingly, the mechanical robustness of the skin sensor device 1 is improved.

The passivation layers 200, 400 may be made of a material including polyimide (PI) and epoxy, but is not limited thereto. The passivation layers 200, 400 may be made of the same material or different materials.

The passivation layers 200, 400 may have the same thickness, or different thicknesses.

For example, the passivation layers 200, 400 may have the thickness of 2 um and Young's modulus of 2.8 GPa.

Additionally, when the passivation layers 200, 400 are stacked upon each other, each includes a plurality of through-holes to form a perforated pattern. The plurality of through-holes for each layer may form a pattern of a specific array structure. The planar structure of the hole patterns of the passivation layers 200, 400 will be described in more detail below with reference to FIGS. 8 to 12.

The electronic circuit unit 300 is an electronic circuit including a device unit which operates to perform the monitoring function of the sensor module 30. The electronic circuit unit 300 includes interconnect 301 and at least one device unit.

The interconnect 301 is a circuit component used to implement the electronic circuit, and is configured to allow the flow of electric current outputted from the device units (for example, a sensing unit) of the electronic circuit unit 300. The interconnect 301 may be connected to the electrodes of the sensing unit to transmit the electric current outputted from the electrodes.

The interconnect 301 is positioned on the surface of the flexible patch 60. When the sensor module 30 includes the first passivation layer 200, the interconnect 301 may be positioned on the first passivation layer 200.

The interconnect 301 may be formed in some or all of regions in which the device unit(s) are not disposed in the corresponding layer. For example, the interconnect 301 may be formed to connect regions I, II, III, IIII of FIG. 1 in which the sensing unit is positioned.

The interconnect 301 is made of a conductive material. The interconnect 301 may be made of, for example, a material including Au, but is not limited thereto.

The sensing unit is a device unit installed on the first passivation layer 200, and includes a material having semiconductor properties. The sensing unit may generate the electric current in response to a change in the skin itself or the surrounding environment. The sensing unit may be used to monitor the skin condition. The generated electric current (for example, the variable electric current) flows from the sensing unit 310, 320, 330, 340 to an analyzer (not shown) through the interconnect 301.

In the certain embodiments, the sensor module 30 may include a temperature sensing unit 310; a hydration sensing unit 320; a photo sensing unit 330 and/or a strain sensing unit 340 to sense strain on the attached skin. When the electronic circuit unit 300 includes the sensing unit, the sensor module 30 may perform the operation of sensing a change in the user's skin condition, and the skin sensor device 1 may be used to obtain temperature information, moisture information and strain information of the skin and/or light information.

The at least one sensing unit 310, 320, 330, 340 may be distributed in different regions on the NMP surface of the sensor module 30 according to the type. For example, as shown in FIG. 2, the temperature sensing unit 310 may be built in region 2, the hydration sensing unit 320 may be built in region 3, the photo sensing unit 330 may be built in region 4, and the strain sensing unit 340 may be built in region 5.

The temperature sensing unit 310 senses the temperature of the attached skin. The temperature sensing unit 310 may generate the changed electric current in response to a change in the temperature of the attached skin. The skin sensor device 1 may measure the user's skin temperature by the sensor module 30 including the temperature sensing unit 310.

Figure 4:
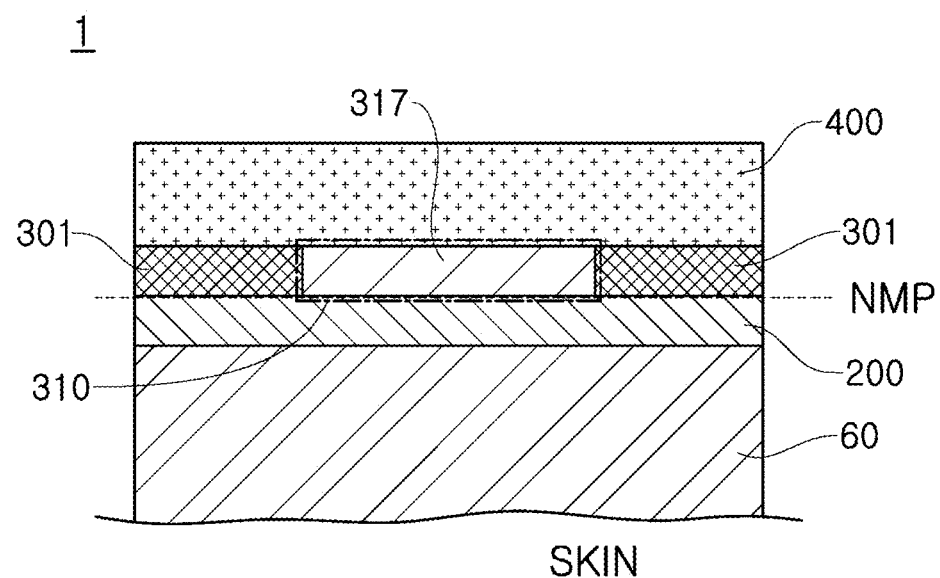
FIG. 4 is a schematic cross-sectional view of a temperature sensing unit according to an embodiment of the present disclosure.

FIG. 4 is a schematic cross-sectional view of the temperature sensing unit according to an embodiment of the present disclosure.

Referring to FIG. 4, the temperature sensing unit 310 may include a temperature responsive layer 317.

The temperature responsive layer 317 is made of a material that changes in semiconductor properties in response to a change in temperature. The change in semiconductor properties is represented as a change in electric current, resistance, or other electricity related properties. The temperature responsive material may include, for example, Pt, but is not limited thereto.

The temperature sensing unit 310 may generate the electric current in response to the temperature by the temperature responsive layer 317. As the temperature responsive layer 317 changes in electrical properties in response to a change in temperature, the temperature sensing unit 310 may generate the electric current that changes in response to a change in temperature.

The temperature responsive layer 317 is connected to the interconnect 301 positioned near the temperature sensing unit 310. Some or all of the edges of the temperature responsive layer 317 having a predetermined area may be connected to the adjacent interconnect 301. The connected part of the adjacent interconnect 301 may act as the electrode of the temperature sensing unit 310.

In an embodiment, the temperature responsive layer 317 may be connected to be positioned on the same plane as the interconnect 301. The temperature sensing unit 310 is a planar structure integrally formed with the interconnect 301, and the planar part of the temperature sensing unit 310 and the planar part of the interconnect 301 may be implemented as layers of the electronic circuit unit 300 made of different materials.

Here, being positioned on the same plane represents that the temperature responsive layer 317 is not connected on the surface of the adjacent interconnect 301 and is positioned on the same plane. Being positioned on the same plane encompasses that a step is formed on the upper surface due to different thicknesses when the interconnect 301 and the temperature responsive layer 317 are positioned on the same plane.

At least some (for example, one end and/or the other end) of the edges of the temperature responsive layer 317 may be directly connected to the side of the interconnect 301 positioned on the first passivation layer 200. Thus, the temperature responsive layer 317 is positioned on the same plane as the interconnect 301 (the surface of the first passivation layer 200).

The electric current generated by the temperature responsive layer 317 is transmitted to the analyzer (not shown) through the connected interconnect 301.

In some embodiments, the temperature responsive layer 317 may be formed with a different thickness from the adjacent interconnect 301. For example, when the temperature responsive layer 317 is a Pt layer and the interconnect 301 is an Au layer, the thickness of the Pt layer 317 may be 35 nm to 45 nm, for example, approximately 40 nm, and the thickness of the Au layer 301 may be 95 nm to 105 nm, for example, approximately 100 nm.

In some other embodiments, the temperature sensing unit 310 may be formed with the same thickness as the interconnect 301. For example, the temperature responsive layer 317 and the interconnect 301 may have the thickness of 100 nm.

Additionally, when some or all of the interconnects 301 are stacked with the other components 60, 200, 400, each includes a plurality of through-holes to form a perforated pattern. The plurality of through-holes formed in the interconnect 301 may form a pattern of a specific array structure corresponding to the hole patterns of the other components. The hole pattern of the interconnect 301 will be described in more detail below with reference to FIG. 4, etc.

The hydration sensing unit 320 senses moisture in the attached skin. The hydration sensing unit 320 may generate the changed electric current in response to a change in moisture in the attached skin. The skin sensor device 1 may measure the amount of moisture of the user by the sensor module 30 including the hydration sensing unit 320.

Figure 5:
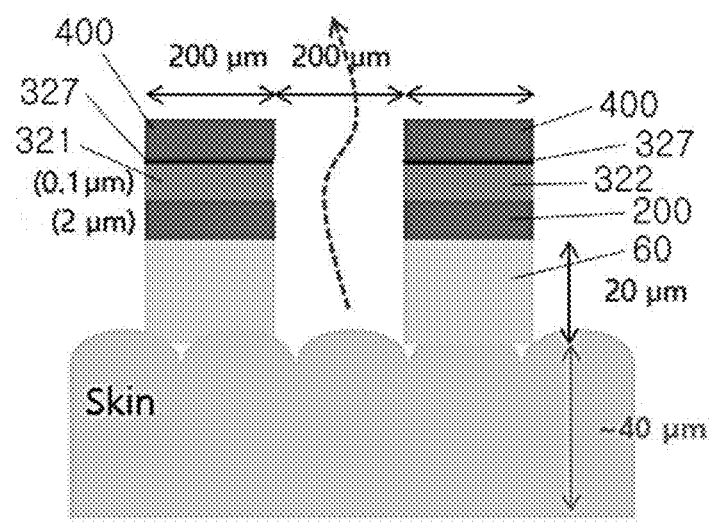
FIG. 5 is a schematic cross-sectional view of a hydration sensing unit according to an embodiment of the present disclosure.

FIG. 5 is a schematic cross-sectional view of the hydration sensing unit according to an embodiment of the present disclosure.

Referring to FIG. 5, the hydration sensing unit 320 is positioned between the interconnects 301. The hydration sensing unit 320 includes a plurality of electrodes 321, 322 and a hydration responsive layer 327.

The plurality of electrodes includes at least one electrode 321 and at least one electrode 322. The electrode 321 is connected to one interconnect 301, and the electrode 322 is connected to the other interconnect 301.

The electrodes 321, 322 have such a cantilever structure that one end is connected to the interconnect 301 and extends to the other side from the connected interconnect 301. The edges of a board extended from the electrodes 321, 322 may extend across the planar part of the dumbbell hole (for example, the edge surrounding the dumbbell hole) of the first passivation layer.

In certain embodiments, a set of the plurality of electrodes may include a subset of the plurality of electrodes 321 and another subset of the plurality of electrodes 322. The plurality of electrodes 321, 322 may be built with an interdigitated electrodes structure. The extended parts (i.e., the board) of the cantilever of the electrodes 321, 322 in the hydration sensing unit 320 are arranged in an interdigitated array. The board of the electrode 322 is positioned near the board of the electrode 321.

The interdigitated electrodes 321, 322 are formed for non-galvanic, capacitive-type hydration sensors.

In an embodiment, the width of the extended board of the electrode 321 or the width of the extended board of the electrode 322 may be equal to the distance between the adjacent electrodes 321, 322 arranged in an interdigitated array.

For example, as shown in FIG. 5, the interspacing of the board of the electrode 321, the board of the electrode 322 and the electrodes 321, 322 may be 200 um.

In an embodiment, the electrodes 321, 322 may be formed with the same thickness as the interconnect 301. For example, the electrodes 321, 322 and the interconnect 301 may have the thickness of 100 nm.

The hydration responsive layer 327 is formed on the surface of the electrodes 321, 322. The hydration responsive layer 327 includes a material that changes in semiconductor properties in response to a change in hydration. The change in semiconductor properties is represented as a change in electrical properties such as electric current properties. The hydration responsive material may include, for example, Pt, Cr and/or Au, but is not limited thereto.

The hydration responsive layer 327 may have a smaller thickness than the electrodes 321, 322. For example, when the electrodes 321, 322 are 100 nm in thickness, the hydration responsive layer 327 may be 0.5 nm to 1.5 nm, for example, approximately 1 nm in thickness. However, this is provided by way of illustration, and the thickness of the electrodes 321, 322 is not limited thereto.

The hydration responsive layer 327 may generate the electric current in response to moisture. The hydration responsive layer 327 may generate the changed electric current in response to a change in skin moisture or ambient moisture. The generated electric current is transmitted to the analyzer (not shown) through the electrodes 321, 322 and the interconnect 301.

Additionally, each of the electrodes 321, 322 and the hydration responsive layer 327 includes a plurality of through-holes. The electronic circuit unit 300 including the hydration sensing unit 320 forms a perforated pattern when stacked with the other components 60, 200, 400. In certain embodiments, some or all of the plurality of through-holes of the electrodes 321, 322 and the hydration responsive layer 327 may form a pattern of a specific array structure corresponding to the hole patterns of the other components 60, 200, 400 at least in part. The hole pattern and the planar structure of the hydration sensing unit 320 will be described in more detail below with reference to FIG. 11, etc.

The photo sensing unit 330 senses light irradiated on the attached skin. The photo sensing unit 330 may generate the changed electric current in response to a change in light irradiated on the attached skin. The skin sensor device 1 may sense whether light is irradiated on the user's skin by the sensor module 30 including the photo sensing unit 330 and the band of the irradiated light, or may measure the intensity of the irradiated light.

Figure 6:
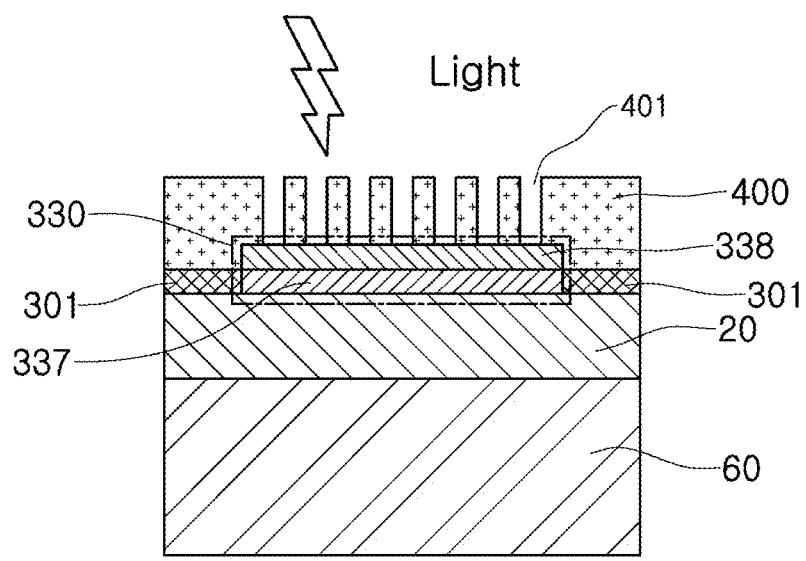
FIG. 6 is a schematic cross-sectional view of a photo sensing unit according to an embodiment of the present disclosure.

FIG. 6 is a schematic cross-sectional view of the photo sensing unit according to an embodiment of the present disclosure.

Referring to FIG. 6, the photo sensing unit 330 may include a photo responsive layer 337.

The photo responsive layer 337 is made of a material that changes in semiconductor properties in response to light irradiation. For example, the photo responsive layer 337 may be made of a semiconductor material having band gap energy corresponding to a specific frequency band. When a specific frequency band of light is irradiated, the photo responsive material changes in electrical properties (for example, semiconductor properties) in response to the irradiated light.

In an embodiment, the photo responsive material may be a material having a band gap included in the specific frequency band. Here, the specific frequency band may be all or part of the ultraviolet (UV) band. For example, the frequency band to which the photo responsive semiconductor material responds is a range of frequencies converted to wavelengths of 400 nm or 380 nm or less.

The photo responsive material that responds to the above-described specific frequency band may include, for example, ZnO, AlN and/or GaN. The photo responsive material may have a monocrystalline or polycrystalline structure. For example, the photo responsive layer 337 may be made of polycrystalline ZnO.

ZnO and GaN have band gap energy (i.e., approximately 3.4 eV) corresponding to the frequency that is converted to approximately 365 nm wavelength. Accordingly, the sensor module 30 having the photo responsive layer made of ZnO and GaN may be used as a UV light sensor.

However, the photo responsive material is not limited to the above-described materials, and may be any other piezoelectric material and any other light active material.

The photo sensing unit 330 generates the electric current in response to to light irradiation on the photo responsive layer 337. The photo sensing unit 330 may generate the changed electric current in response to a change in light irradiation.

When the specific band of light is irradiated, the photo responsive layer 337 may generate the electric current in response to the irradiated light, and/or the photo responsive layer 337 may generate the change electric current when the intensity of the irradiated light changes.

The photo responsive layer 337 is connected to the interconnect 301 positioned near the photo sensing unit 330. One end and the other end of the photo responsive layer 337 having a predetermined area may be connected to the adjacent interconnect 301. The connected part of the adjacent interconnect 301 may act as the electrode of the photo sensing unit 330.

In an embodiment, the two ends of the photo responsive layer 337 may be connected on the surface of the adjacent interconnect 301. The photo responsive layer 337 may be built with a free-standing structure that the two ends are supported by the electrode part of the interconnect 301.

The generated electric current is transmitted to the analyzer (not shown) through the interconnect 301.

In an embodiment, the sensor module 30 may include the second passivation layer 400 having at least one auxiliary through-hole 401 in an area that covers the photo sensing unit 330.

The auxiliary through-hole 401 is part of the second passivation layer 400, and may be formed in a sensing area of the photo sensing unit 330. The sensing area is an area range in which light can directly travel to the photo responsive layer 337 in the absence of the second passivation layer 400. For example, the auxiliary through-hole 401 may be formed in part of the second passivation layer 400 that covers the photo responsive layer 337 of the temperature sensing unit 330.

In a situation in which the second passivation layer 400 absorbs some or all of the specific frequency band of light to which the photo responsive material responds, when the photo responsive layer 337 of the photo sensing unit 330 is entirely covered with the second passivation layer 400, the photo sensing unit 330 may not detect a signal for the irradiated light. However, when the second passivation layer 400 has the auxiliary through-hole 401 as shown in FIG. 6, the photo responsive layer 337 may be optically exposed to the outside, and eventually the sensor module 30 may detect the specific signal corresponding to the specific frequency band more stably.

When the auxiliary through-hole 401 is formed in the second passivation layer 400 part on the photo sensing unit 330, light can directly travel to the photo responsive layer 337 through the cavity of the auxiliary through-hole 401. Light is directly irradiated on the photo responsive layer 337 through the auxiliary through-hole 401. Accordingly, the photo sensing unit 330 has more sensitive light sensing performance.

In an embodiment, the photo sensing unit 330 may further include a capping layer 338 formed on the photo responsive layer 337. The capping layer 338 is positioned at the interface between the photo responsive layer 337 and the second passivation layer 400.

The capping layer 338 is made of a transparent material to allow light having passed through the auxiliary through-hole 401 to travel to the photo responsive layer 337 without interruption.

Additionally, the capping layer 338 prevents chemical damages of the photo responsive layer 337 caused by the contact of an external material with the photo responsive layer 337 through the auxiliary through-hole 401.

The capping layer 338 may be made of, for example, a material including $HfO_2$, $Si_3N_4$, SiNx or a combination thereof, but is not limited thereto.

In an embodiment, the photo sensing unit 330 may be built across one end and the other end of the specific through-hole of the flexible patch 60. For example, one end of the photo sensing unit 330 may be positioned on part of the flexible patch 60 surrounding the specific through-hole of the flexible patch 60, and the other end of the photo sensing unit 330 may be positioned on the opposite part of the flexible patch 60. The specific through-hole is a through-hole having a planar shape and/or size that is different from each perforation of the perforated pattern formed by the stack of the hole patterns for each layer of the skin sensor device 1.

In an embodiment, the flexible patch 60 may be formed such that its part is positioned across the specific through-hole. Thus, the photo sensing unit 330 may be built on the part of the flexible patch 60 positioned across the specific through-hole. The photo sensing unit 330 may be supported by the part of the flexible patch 60 positioned across the specific through-hole.

The planar structure of the photo sensing unit 330 will be described in more detail below with reference to FIGS. 16 and 30.

The strain sensing unit 340 senses strain of the attached skin. The strain sensing unit 340 may generate the changed electric current in response to the strain of the attached skin.

Figure 7:
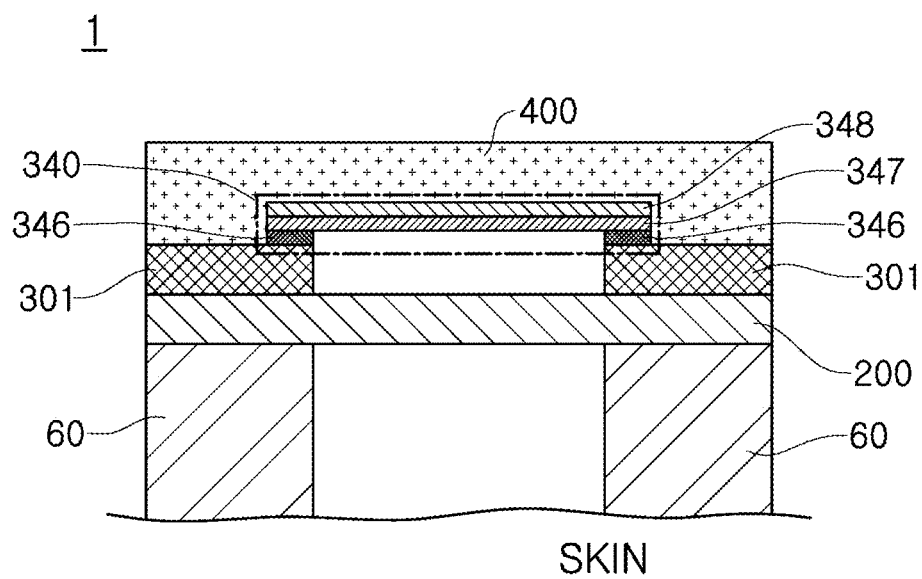
FIG. 7 is a schematic cross-sectional view of a strain sensing unit according to an embodiment of the present disclosure.

FIG. 7 is a schematic cross-sectional view of the strain sensing unit according to an embodiment of the present disclosure.

Referring to FIG. 7, the strain sensing unit 340 may include an active layer 347.

The active layer 347 is made of a material that changes in semiconductor properties in response to strain. A change in semiconductor properties is represented as a change in electric current, resistance or other electricity related properties. With the semiconductor properties, the generation of the electric current is activated when strain is applied to the sensor module 30 (or the skin sensor device 1). The strain responsive material having the semiconductor properties may be a material that has good electron transport characteristics and may be used as a piezoelectric material. For example, the strain responsive material may be a material including ZnO, AlN, GaN or a combination thereof, but is not limited thereto, and may be any other piezoelectric material.

The strain sensing unit 340 generates the electric current in response to the strain of the skin sensor device 1. When strain is applied to the skin to which the skin sensor device 1 is attached, the strain is also applied to the active layer 347. For example, the structure of the active layer 347 may change depending on the skin strain. Thus, the strain sensing unit 340 may generate the changed electric current in response to a change in the strain of the active layer 347.

The active layer 347 is connected to the interconnect 301 positioned near the strain sensing unit 340. One end and the other end of the active layer 347 having a predetermined area may be connected to the adjacent interconnect 301. The connected part of the adjacent interconnect 301 may act as the electrode of the strain sensing unit 340.

In an embodiment, the two ends of the active layer 347 may be connected on the surface of the adjacent interconnect 301. The active layer 347 may be built with a free-standing structure that the two ends are supported by the electrode part of the interconnect 301.

The generated electric current is transmitted to the analyzer (not shown) through the interconnect 301.

The strain sensing unit 340 is encapsulated with the upper/lower passivation layers 200, 400 and the unit is positioned close to the neutral mechanical plane (NMP). Accordingly, the mechanical robustness of the sensor module 30 is improved.

In an embodiment, the strain sensing unit 340 may further include a bottom capping layer 346 and/or a top capping layer 348. The bottom capping layer 346 and the top capping layer 348 are an interfacial layer which is inserted into the interface between the active layer 347 and the passivation layers 200, 400. As shown in FIG. 7, the bottom capping layer 346 is positioned below the active layer 347. The top capping layer 348 is positioned on the active layer 347.

The bottom capping layer 346 is inserted into the electrodes 341, 342 of the active layer 347/the interconnect 301 to form a Schottky barrier for allowing the strain sensing unit 340 to use the piezoelectric effect.

The top capping layer 348 is formed on the strain sensing unit 340, and protects the strain sensing unit (for example, the active layer 347) in the subsequent process.

The thickness of the bottom capping layer 346 and the top capping layer 348 may be different. For example, the top capping layer 348 may be 2.5 nm to 3.5 nm, for example, approximately 3 nm in thickness. The bottom capping layer 346 may be 1 nm to 2 nm, for example, approximately 1.5 nm in thickness.

The bottom capping layer 346 and/or the top capping layer 348 may be made of a material including $HfO_2$, $Si_3N_4$, SiNx, epoxy resin or a combination thereof, but is not limited thereto, and may be made of any other resin material.

In an embodiment, the strain sensing unit 340 may be built across one end and the other end of the specific through-hole of the flexible patch 60. For example, one end of the strain sensing unit 340 (for example, the active layer 347) is positioned on part of the flexible patch 60 disposed around the specific through-hole of the flexible patch 60, and the other end of the strain sensing unit 340 (for example, the active layer 347) may be positioned on the other part opposite the part of the flexible patch 60. The specific through-hole is a through-hole having a planar shape and/or size that is different from each perforation of the perforated pattern formed by the stack of the hole patterns for each layer of the skin sensor device 1.

In an embodiment, the flexible patch 60 may be formed such that its part is positioned across the specific through-hole. Thus, the strain sensing unit 340 may be built on the part of the flexible patch 60 positioned across the specific through-hole. The strain sensing unit 340 may be supported by the part of the flexible patch 60 positioned across the specific through-hole.

In an embodiment, the strain sensing unit 340 may be positioned on the cavity formed in the specific through-hole. For example, as shown in FIG. 7, the stack of the first passivation layer 200 and the strain sensing unit 340 may be positioned across one end and the other end of the flexible patch 60 near the specific through-hole. As opposed to the photo sensing unit 330, the strain sensing unit 340 may not be supported by the patch 60. Accordingly, when the structure of the skin sensor device 1 changes due to skin strain, the strain may be applied to the strain sensing unit 340 more sensitively.

The specific through-hole in which the strain sensing unit 340 is built may be a specific through-hole that is the same as or different from the specific through-hole in which the photo sensing unit 330 is built. The photo sensing unit 330 and the strain sensing unit 340 may be configured to go across a same large through-hole, or each of the strain sensing unit 340 and the photo sensing unit 330 may be built in each specific through-hole disposed in different regions as shown in FIG. 2.

The planar structure of the photo sensing unit 330 and the strain sensing unit 340 will be described in more detail with reference to the following FIGS. 16 and 17.

In an embodiment, the thickness of each layer 60, 200, 310, 320, 330, 340, 400 in the skin sensor device 1 is designed based on the material component of each layer and the following Equation:

$$H = \frac{\sum_{i=1}^{n} E_i t_j \left( \sum_{j=1}^{i} t_j - \frac{t_j}{2} \right)}{\sum_{i=1}^{n} E_i t_j}$$

The above Equation 1 is an equation for calculating the height H of NMP present in the multi-stack structure having n layers. Here, the height H is the distance from the bottom of the multi-stack structure. Here, $E_i$ and $t_i$ are the plane-strain coefficient and thickness of the $i^{th}$ layer, and the bottom layer is i=1.

For example, in the region 5 in which the strain sensing unit 340 is built, the flexible patch 60 may be designed with the thickness of 20 um, the first passivation layer 200 with the thickness of 2 um, the electrodes 341, 342 with the thickness of 100 nm, the bottom capping layer 346 with the thickness of 1.5 nm, the active layer 347 with the thickness of 100 nm, the top capping layer 348 with the thickness of 3 nm, the second passivation layer 400 with the thickness of 2 um, respectively, according to the above Equation 1. However, these values are provided by way of illustration, and the thickness of each layer of the skin sensor device 1 is not limited thereto.

In an embodiment, the skin sensor device 1 may further include an alignment key 500 for fixing the stack and connection of each component 60, 200, 300, 400. The alignment key 500 is implemented with a structure that is difficult for each component 60, 200, 300, 400 to make planar rotation.

Additionally, the skin sensor device 1 may include a plurality of alignment keys 500 as shown in FIG. 2.

The sensor module 30 may include at least one sensing unit for each type. Each sensing unit obtains information of different directions and different regions.

In an embodiment, the sensor module 30 may include a pair of strain sensing units 340. Here, one of strain sensing units 340 may be positioned to sense the x-axial strain of the NMP, and the other strain sensing unit 340 may be positioned to sense the y-axial strain of the NMP. For example, as shown in FIG. 2, the strain sensing units 340 may be positioned, for example, perpendicular to each other to obtain strain information of each direction, unique to the dimensional axis.

The components 60, 200, 300, 400 stacked in the skin sensor device 1 have a plurality of through-holes. In each component 60, 200, 300, 400 of the skin sensor device 1, some or all of the plurality of through-holes may form a particular hole pattern in which specific through-holes are arranged repeatedly.

When the components 60, 200, 300, 400 having the corresponding hole patterns are stacked upon each other to build the skin sensor device 1, each specific hole pattern has a planar pattern structure corresponding to each other to form a perforated pattern passing through the cross section from one surface of the skin sensor device 1 to the other surface. For example, a hole pattern formed by at least some of the plurality of through-holes of the first passivation layer 200, a hole pattern formed by at least some of the plurality of through-holes of the electronic circuit unit 300, and a hole pattern formed by at least some of the plurality of through-holes of the second passivation layer 400 have planar patterns corresponding to each other to form open channels when the first passivation layer 200, the electronic circuit unit 300 and the second passivation layer 400 are stacked.

In certain embodiments, the specific hole pattern is a hole pattern formed with an array structure having auxetic properties, and may be referred to as an auxetic hole pattern.

In general, the auxetic structure refers to a structure of which the dimension increases in a direction perpendicular to a first direction when subjected to a tensile force in the first direction. For example, in case that the auxetic structure may be described as having a length, a width and a thickness, when the auxetic structure is subjected to a tensile force in the vertical direction, its width increases. Additionally, the auxetic structure is bidirectional so that when stretched in the vertical direction, its length and width increases, and when stretched in the horizontal direction, its width and length increases, but its thickness does not increase. The auxetic structure has a negative poisson's ratio.

Figure 8:
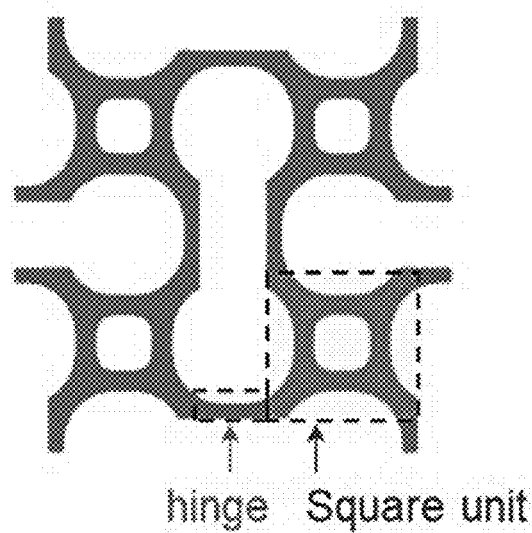
FIG. 8 is a diagram showing an auxetic hole pattern according to an embodiment of the present disclosure.

FIG. 8 is a diagram showing the auxetic hole pattern according to an embodiment of the present disclosure.

Referring to FIG. 8, the auxetic hole pattern is a pattern structure in which dumbbell shaped through-holes (hereinafter, the "dumbbell holes") and/or circular holes are arranged. For example, the auxetic hole pattern may be a pattern of arrangement of dumbbell holes and circular holes.

The dumbbell hole includes a circular part positioned at each of two ends and a central part connecting the circular parts. The width of the central part may be narrower than the diameter of each circular part.

In the auxetic hole pattern, the dumbbell hole is arranged in an interdigitated array with respect to the adjacent other dumbbell hole such that the circular part in the linear extension direction is close to the linear part of the other dumbbell hole. As shown in FIG. 8, each dumbbell hole has an interdigitated planar structure in which the connecting part of each dumbbell hole is positioned perpendicular to the connecting part of the adjacent dumbbell hole. Thus, hole pattern forms an auxetic hole pattern having auxetic properties.

The plurality of dumbbell holes arranged in an interdigitated array forms a hinge area between adjacent other dumbbell holes.

The auxetic hole pattern may further include a plurality of circular holes that may be formed in the remaining region in which the array of dumbbell holes is not formed. The remaining region is a sub region (the hinge area of FIG. 8) surrounded by the interdigitated dumbbell holes. As shown in FIG. 8, each circular hole in the array of circular holes may be arranged such that it is surrounded by the circular part of the adjacent other dumbbell hole.

When the plurality of circular holes is added, the skin sensor device 1 having an auxetic perforated pattern by the stack of the auxetic hole patterns has improved air permeability.

In an embodiment, each circular hole of the array of circular holes may have a diameter that is different from that of the circular part of each dumbbell hole of the array of dumbbell holes. For example, each circular hole of the array of circular holes may be configured to have a smaller diameter than the circular part of each dumbbell hole of the array of dumbbell holes.

Additionally, each through-hole in the auxetic hole pattern may be distributed such that the interspacing between at least some holes is 60 μm or less. For example, the interspacing between all the through-holes of the auxetic hole pattern in the skin sensor device 1 may be 60 μm or less. Additionally, when an auxetic perforated pattern is formed by the stack of the auxetic hole patterns for each layer, each perforation in the auxetic perforated pattern may be distributed such that the interspacings between at least some perforations each other are 60 μm or less.

It is known that the area of the sweat pore has a diameter of 60 μm or more and an average diameter of 80 μm. Additionally, since the amount of waste products to be secreted and biological functions performed by sweat such as temperature control are different depending on skin location, sweat pores are arranged with different distribution densities depending on the body parts. For example, sweat pores are distributed with the density of 60 $cm^{-2}$ in the back, 400 $cm^{-2}$ in the palm, and 180 $cm^{-2}$ in the forehead.

When the interspacing between the through-holes is 60 μm or more, the surface of the flexible patch 60 near the holes may block the sweat pores at least in part. In contrast, the skin sensor device 1 having the hole interspacing of less than 60 μm may obtain higher air permeability (for example, almost 100% air permeability).

Each layer 60, 200, 300, 400 that constitutes the skin sensor device 1 forms the auxetic hole pattern. The skin sensor device 1 is fabricated by stacking each layer 60, 200, 300, 400 in a sequential order. Thus, perforations which are open channels through which a fluid flows may be built between the lowermost layer 60 of the skin sensor device 1 that contacts the skin and the uppermost layer 400 opposite the lowermost layer 60.

The sidewall of each perforation in the perforated pattern of the skin sensor device 1 includes sidewalls of the through-holes of the auxetic hole patterns for each layer 60, 200, 300, 400. When the auxetic hole patterns for each layer 200, 300, 400 of the sensor module 30 are stacked, open channels that constitute some of the perforation sidewalls in the perforated pattern of the skin sensor device 1 are built.

Figure 9:
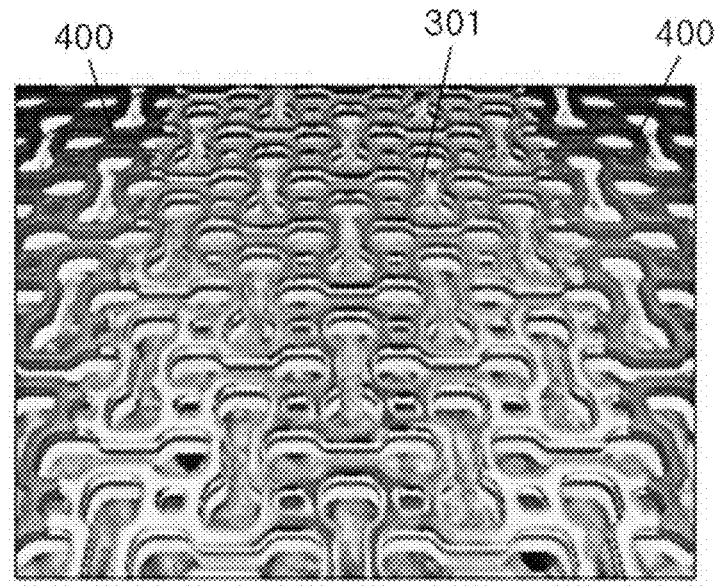
FIG. 9 is a schematic diagram of region 1 in which interconnect is built according to an embodiment of the present disclosure.

FIG. 9 is a schematic diagram of region 1 in which the interconnect 301 is built according to an embodiment of the present disclosure. In FIG. 9, the area that covers the interconnect 301 in the second passivation layer 400 is omitted.

Referring to FIG. 9, each of the flexible patch 60, the first passivation layer 200, the interconnect 301 and the second passivation layer 400 stacked in region 1 includes an auxetic hole pattern. The auxetic hole patterns for each layer 60, 200, 301, 400 form an auxetic perforated pattern when stacked such that the through-holes correspond to each other.

The interconnect 301 of the auxetic hole pattern may be configured such that the pattern of the edge is connected to the auxetic hole pattern of the adjacent second passivation layer 400.

Figure 10:
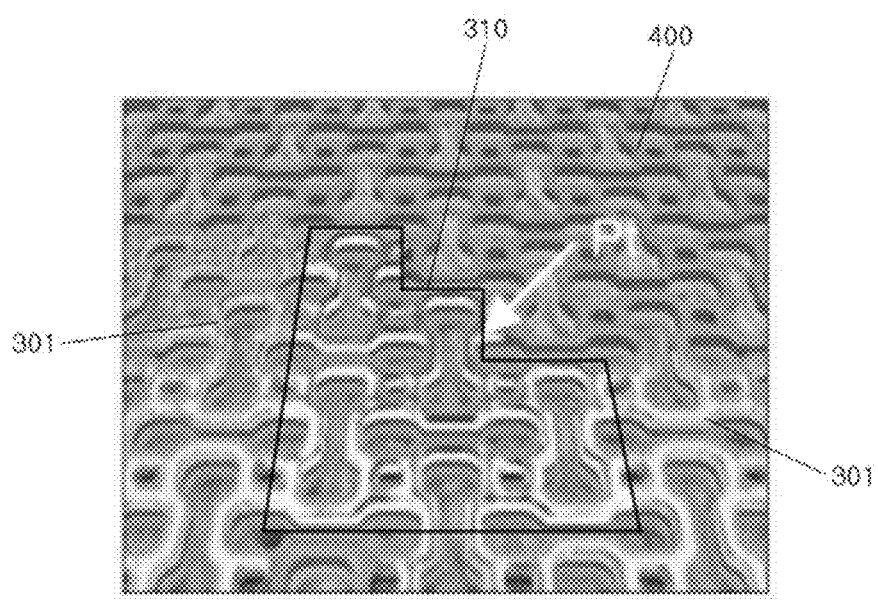
FIG. 10 is a schematic diagram of region 2 in which a temperature sensing unit is built according to an embodiment of the present disclosure.

FIG. 10 is a schematic diagram of region 2 in which the temperature sensing unit 310 is built according to an embodiment of the present disclosure. In FIG. 10, the area that covers the temperature sensing unit 310 in the second passivation layer 400 is omitted.

Referring to FIG. 10, each to the flexible patch 60, the first passivation layer 200, the temperature sensing unit 310 and the interconnect 301 connected the temperature sensing unit 310 stacked in region 2 includes an auxetic hole pattern.

The temperature sensing unit 310 may be implemented as mesh construction of the auxetic hole pattern.

The auxetic hole pattern in the temperature sensing unit 310 (for example, the temperature responsive layer 317) has a planar pattern partially corresponding to the hole pattern of the first passivation layer 200 and the hole pattern of the second passivation layer 400. The entire auxetic hole pattern of the temperature sensing unit 310 may correspond to a sub pattern of the auxetic hole pattern of the passivation layers 200, 400.

The edge to be connected to the interconnect 301 in the auxetic hole pattern of the temperature sensing unit 310 may be implemented in a shape that completes an auxetic hole pattern when connected to the interconnect 301.

Figure 11:
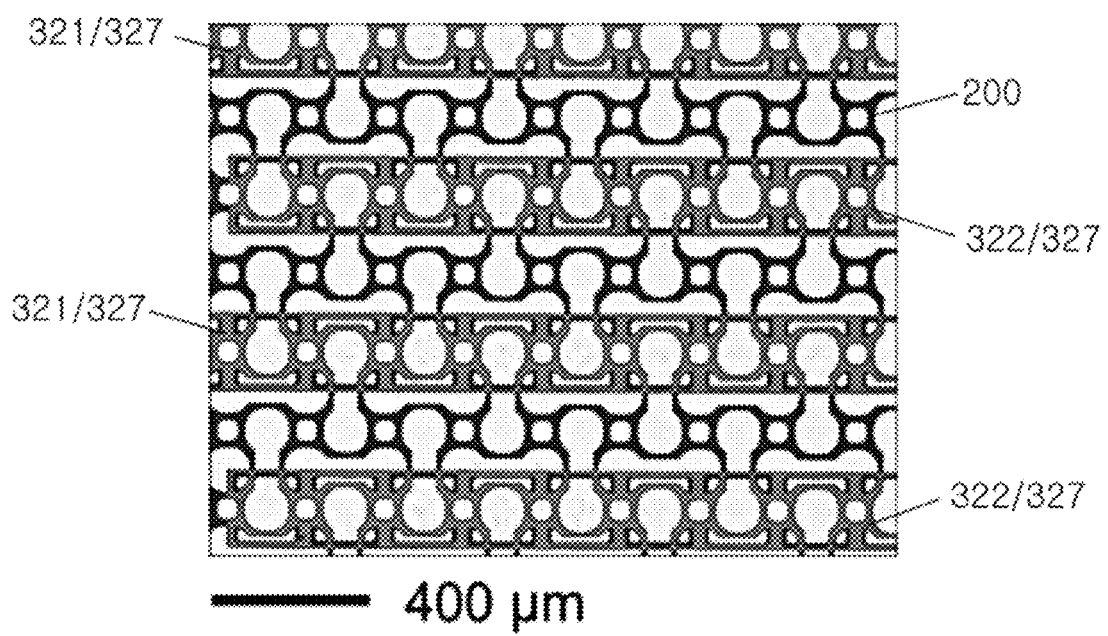
FIG. 11 is a plan view of region 3 in which a hydration sensing unit is built according to an embodiment of the present disclosure.

FIG. 11 is a plan view of region 3 in which the hydration sensing unit 320 is built according to an embodiment of the present disclosure. In FIG. 11, the second passivation layer 400 is omitted.

Referring to FIG. 11, the hydration sensing unit 320 includes an auxetic hole pattern. In certain embodiments, the electrodes 321, 322 and the hydration responsive layer 327 include the auxetic hole pattern.

The auxetic hole pattern of the electrodes 321, 322 and the auxetic hole pattern of the hydration responsive layer 327 correspond to each other. In an embodiment, the plane of the auxetic hole pattern of the electrodes 321, 322 and the plane of the auxetic hole pattern of the hydration responsive layer 327 may match each other.

The plurality of through-holes that forms the auxetic hole pattern of the hydration sensing unit 320 (for example, the auxetic hole pattern of the electrodes 321, 322 and the auxetic hole pattern of the hydration responsive layer 327) has a planar shape corresponding to the planar shape of the through-holes in the hole pattern of the first passivation layer 200 and the hole pattern of the second passivation layer 400, at least in part.

The auxetic hole pattern of the hydration sensing unit 320 includes through-holes corresponding to the entire planar shape of the through-holes of the other layers 200, 400. For example, as shown in FIG. 11, the circular holes arranged in parallel to the electrodes 321, 322 are a sub pattern of the auxetic hole pattern of the other layers 200, 400, and correspond to the entire shape of the circular holes.

The auxetic hole pattern of the hydration sensing unit 320 includes through-holes corresponding to part of the shape of the through-holes of the other layers 200, 400. As shown in FIG. 11, the dumbbell holes included in the electrodes 321, 322 have a planar shape formed by a portion of the circular part and its connected central part in the dumbbell holes of the other layers 200, 400. The dumbbell hole of the hydration sensing unit 320 partially corresponds to the planar shape of the dumbbell holes of the other layers 200, 400.

Additionally, the edges of the electrodes 321, 322 and the hydration responsive layer 327 that form the edges of the cantilever in the hydration sensing unit 320 may have a planar shape corresponding to part of the shape of the through-holes of the other layers 200, 400. As shown in FIG. 11, a planar shape partially corresponding to the circular holes of the other layers 200, 400 may be formed at the extended end.

When the electronic circuit unit 300 including the temperature sensing unit 310 and the hydration sensing unit 320 having the planar structure of the auxetic hole pattern is stacked with the flexible patch 60, the first passivation layer 200 and the second passivation layer 400 having the corresponding auxetic hole pattern, a perforated pattern having the plane of the auxetic hole pattern is formed.

Due to the planar structure (for example, the mesh structure) of the auxetic hole pattern, the sensor module 30 may maintain the open channels that allow the skin to breathe in the region in which the temperature sensing unit 310 and/or the hydration sensing unit 320 are built.

Even though the hole pattern of the hydration sensing unit 320 partially corresponds to the hole pattern of the other layers 200, 400, a perforated pattern that act as open channels in the sensor module 30 and the skin sensor device 1 may be formed. The perforations in the perforated pattern can sufficiently act as open channels even though they are partially blocked. It is because the mesh of the hydration sensing unit 320 has a small width such as a few tens of nm to a few hundreds of nm.

In an embodiment, in the auxetic hole patterns for each layer that form the perforated pattern, the auxetic hole pattern of a layer may have respective specifications that are different from that of the auxetic hole pattern of the other layer. The specification of the auxetic hole pattern for each layer is based on the hole size and the hole interspacing.

Figure 12A:
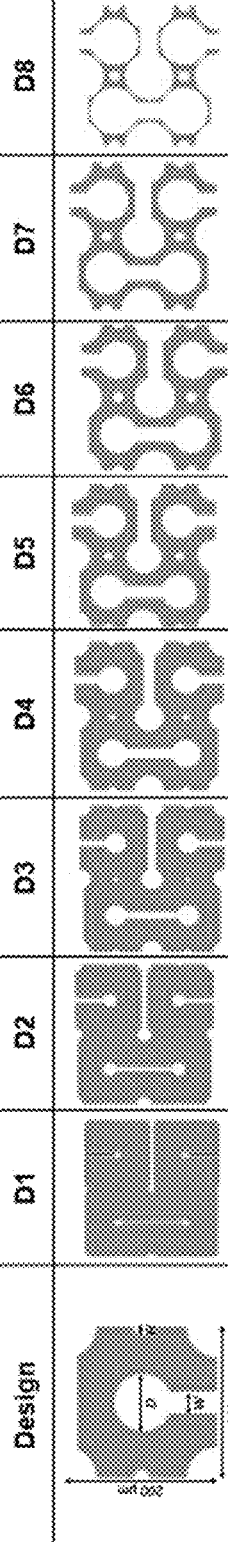
FIG. 12A is a table showing the structural properties of an auxetic hole pattern for each specification.
Figure 12B:
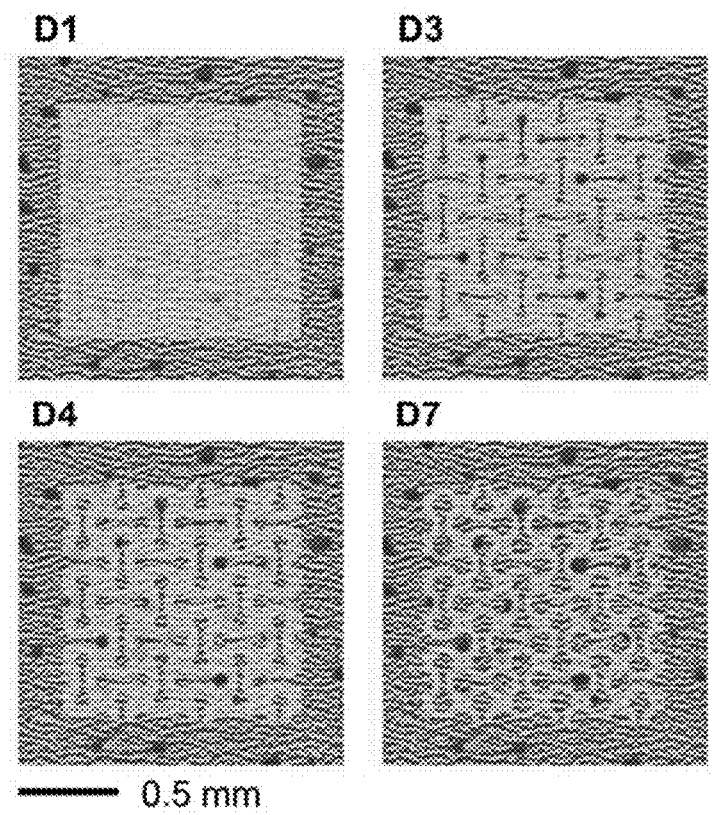
FIG. 12B is an image of an auxetic hole pattern for each layer having the specification selected from the table of FIG. 12A.
Figure 12C:
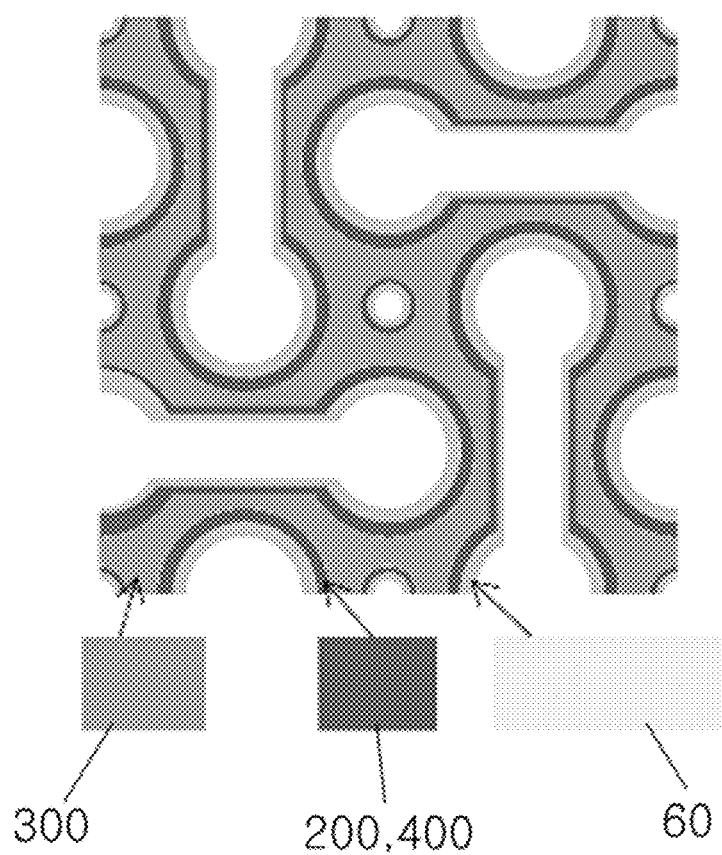
FIG. 12C is a plan view of a skin sensor device including a stack of layers having the specification of the auxetic hole pattern of FIG. 12B.

FIGS. 12A to 12C are diagrams showing the auxetic hole pattern for each layer according to an embodiment of the present disclosure.

FIG. 12A is a table showing the structural properties of the auxetic hole pattern for each specification, and FIG. 12B is an image of the auxetic hole pattern for each layer having the specification selected from the table of FIG. 12A. FIG. 12C is a plan view of the skin sensor device 1 including the stack of the layers 60, 200, 300, 400 having the specification of the auxetic hole pattern of FIG. 12B.

The table of FIG. 12A is obtained under the fixed ratio of the diameter D of the circular part in the dumbbell hole, the auxetic cut width W and the radius R of the circular hole.

Since the material properties and/or purpose of each layer differ, the corresponding through-hole in the auxetic hole pattern for each layer may not match each other.

For example, the auxetic hole pattern of the flexible patch 60 may be designed with the specification D4 of the table of FIG. 12A. In contrast, the auxetic hole pattern of the passivation layer 200, 400 may be designed with the specification D6 of the table of FIG. 12A. Additionally, the auxetic hole pattern of the electronic circuit unit 300 (for example, the Au interconnect 301) may be designed with the specification D7 of the table of FIG. 12A.

The skin sensor device 1 having the planar structure of the auxetic hole pattern has the following advantages: a) high work of adhesion; b) high air permeability; c) high durability. Due to these advantages, the skin sensor device forms a highly conformal contact on the curved skin surface including wrist wrinkles.

Figure 13:
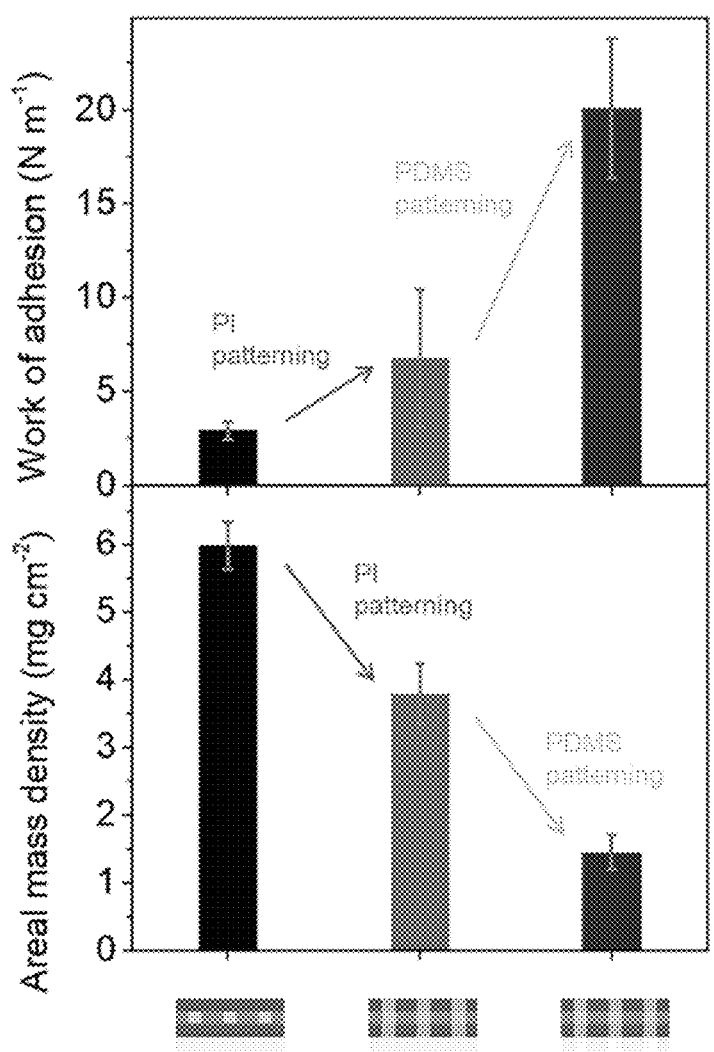
FIG. 13 is a diagram illustrating high work of adhesion of a skin sensor device according to an embodiment.

FIG. 13 is a diagram illustrating high work of adhesion of the skin sensor device according to an embodiment.

As the flexible patch 60 of the skin sensor device 1 is attachable, when the contact area of the flexible patch 60 with the skin increases, the work of adhesion of the skin sensor device 1 increases. Additionally, to implement the imperceptible skin sensor device 1, it is necessary to minimize the areal density of the skin sensor device 1. As the skin sensor device 1 is lighter in weight, the user does not recognize the fact that the skin sensor device 1 is attached to the user's skin, and the skin sensor device 1 does not delaminate from the skin.

Referring to FIG. 13, as each of the stack of the flexible patch 60 and the sensor module 30 has a larger number of perforations of the auxetic hole pattern, the areal mass density of the corresponding stack decreases and the work of adhesion increases.

As the perforation of the auxetic hole pattern is added to the stack, the mass of the space corresponding to the inner cavity of the perforation decreases. Additionally, it is because as the number of perforations increases, the interspacing between perforations decreases and the effective area that contacts the curved skin surface increases.

That is, the skin sensor device 1 has the perforated pattern of the auxetic hole pattern, thereby minimizing the weight load applied to the user's skin, and as a result, the skin sensor device 1 has high work of adhesion.

Figure 14:
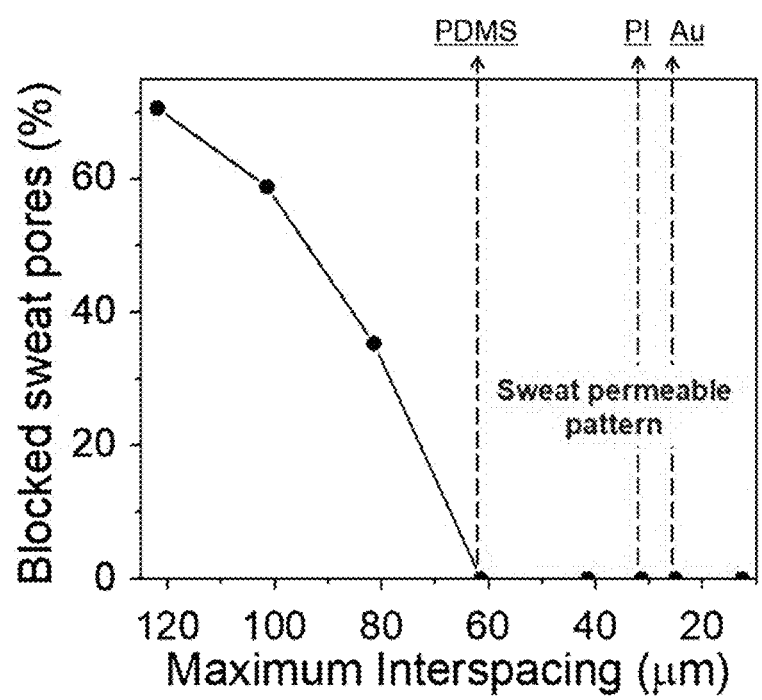
FIG. 14 is a diagram illustrating high air permeability of a skin sensor device according to an embodiment.

FIG. 14 is a diagram illustrating high air permeability of the skin sensor device according to an embodiment.

As described above, the auxetic hole pattern of the skin sensor device 1 has the hole interspacing (for example, the hole interspacing of the flexible patch 60) of 60 μm or less. As shown in FIG. 14, when the widest hole interspacing of the flexible patch 60 that contacts the skin is less than 60 μm, the skin sensor device 1 may have almost 100% air permeability.

Figure 15:
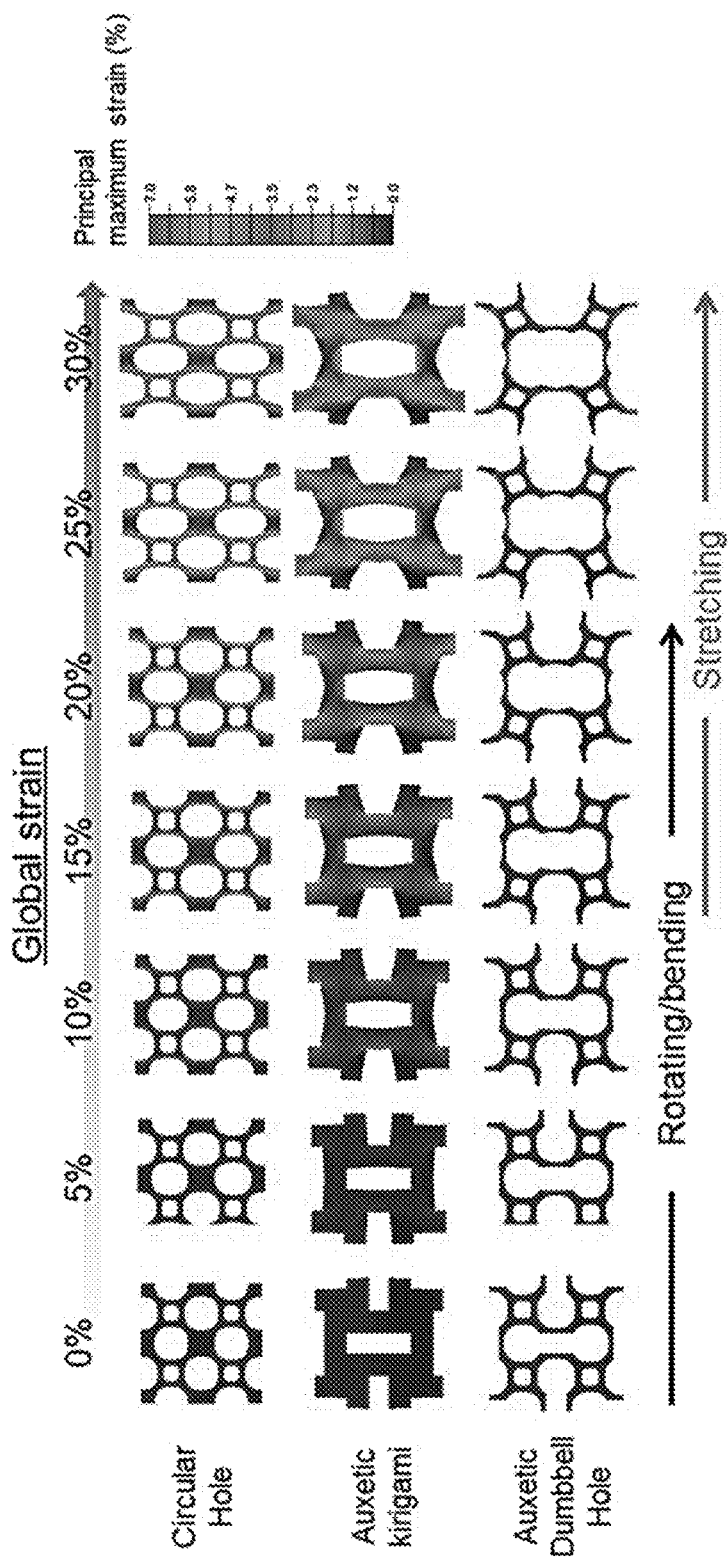
FIG. 15A shows a principal maximum strain distribution of global strain in a pattern formed by circular through-holes alone; a pattern formed by square through-holes alone; an auxetic hole pattern of the present disclosure.
FIG. 15B shows a stress-strain curve of a skin sensor device having an auxetic perforated pattern.
Figure 15B:
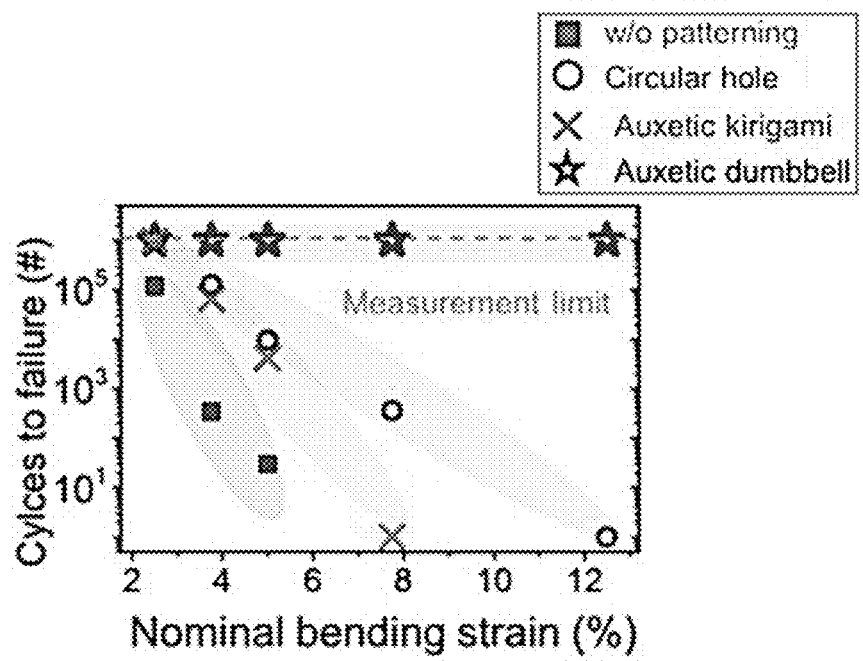

FIGS. 15A to 15B are diagrams illustrating high durability of the skin sensor device according to an embodiment.

FIG. 15A shows a principal maximum strain distribution of global strain in a pattern formed by circular through-holes alone; a pattern formed by square through-holes alone (hereinafter, Auxetic kirigami pattern), and the auxetic hole pattern of the present disclosure. FIG. 15A shows definite element analysis (FEA) results of the tensile properties up to the strain of 30% for each pattern.

The auxetic hole pattern generates elasticity while suppressing cracks caused by strain localization. The auxetic hole pattern is designed in a combined pattern of the auxetic kirigami pattern and the circular pattern to complement the disadvantages of the auxetic kirigami pattern and the circular pattern and provide their unique advantages.

Specifically, part corresponding to the auxetic kirigami pattern in the auxetic hole pattern provides extreme conformability on the bumpy skin surface due to the nonlinear elastic properties, while the other part corresponding to the circular pattern in the auxetic hole pattern provides open channels and lessens the local strain at the edge of the kirigami pattern part.

When the circular hole pattern model is stretched and a network placed in parallel to the axial direction is stretched, the entire structure becomes narrow in the lateral direction. When the auxetic bar pattern or dumbbell through-hole pattern is subjected to a tensile force, structural opening is formed before the material is stretched.

In the circular pattern, when deformation is applied, the square unit rotates and its connected hinge bends. The local deformation is generated at the hinge of the auxetic bar pattern. This is the disadvantage of the auxetic bar pattern which is vulnerable to a mechanical failure and may limit the engineering application program.

However, the auxetic hole pattern of the present disclosure solves the disadvantage at least in part.

As described above with reference to FIG. 8, the auxetic hole pattern formed in each layer include a square rotation unit connected by the hinges as well as dumbbell-shaped through-holes. The dumbbell pattern greatly reduces the strain occurring at the hinge. The C-shaped arc of the circular pattern effectively makes the sharp tip edge dull and finally reduces the strain level. For example, when the overall strain exceeds 15%, the structure of the dumbbell pattern is fully open and stretching of the material itself (i.e., the auxetic hole pattern itself) starts.

The strain delocalization greatly improves the mechanical reliability of the skin sensor as shown in FIG. 15B. Based on the results of FIG. 15, it is obvious that the auxetic dumbbell hole design of the skin sensor that delocalizes the strain distribution can withstand the repeated mechanical strains on the skin during long-term monitoring.

Due to the advantage of the auxetic hole pattern structure, the skin sensor may be used to monitor the user's skin condition for a long time. In addition to the mechanical robustness and the skin-like mechanical properties, it is possible to prevent sensor malfunction caused by sweat accumulation, thereby achieving long-term skin condition monitoring without malfunction of the electronic module for at least 1-2 weeks.

Additionally, with the properties of the auxetic structure by the auxetic perforated pattern, the skin sensor device 1 has human skin-like nonlinear behavioral characteristics.

FIG. 15B shows a stress-strain curve of the skin sensor device having the auxetic perforated pattern. According to the stress-strain curve, the skin sensor device 1 has nonlinear mechanical behaviors, and the mechanical parameters have similar characteristics to the human skin. Accordingly, the skin sensor device 1 can be used as electronic skins (e-skins) that replace human skin in a variety of applications.

Meanwhile, the electronic circuit unit 300 may further include a unit having a planar structure that does not correspond to the auxetic hole pattern of the flexible patch 60. In certain embodiments, the electronic circuit unit 300 may further include the photo sensing unit 330 and/or the strain sensing unit 340. The photo sensing unit 330 and the strain sensing unit 340 may be built in the through-hole that is different from the auxetic hole pattern of the flexible patch 60.

Figure 16:
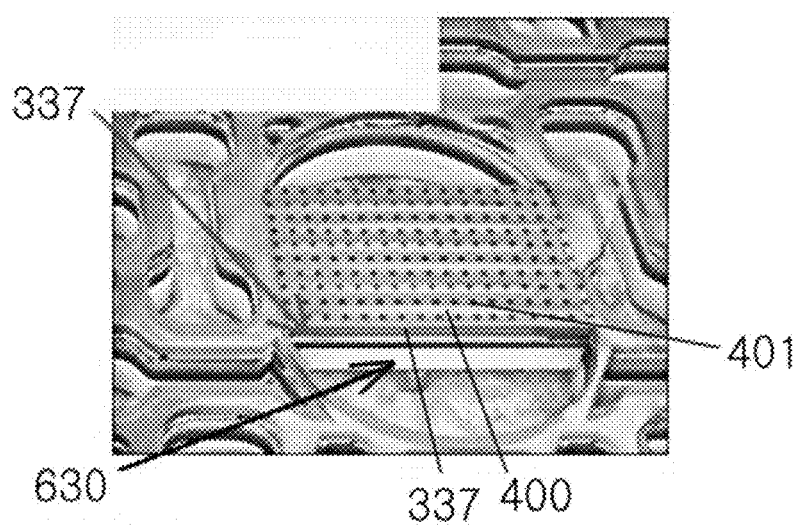
FIG. 16 is a schematic diagram of region 4 in which a photo sensing unit is built according to an embodiment of the present disclosure.

FIG. 16 is a schematic diagram of region 4 in which the photo sensing unit is built according to an embodiment of the present disclosure.

Referring to FIG. 16, the photo sensing unit 330 may be built in the specific through-hole of the flexible patch 60.

As described above with reference to FIG. 6, for the photo sensing unit 330 to perform a photo sensing operation, it is necessary to irradiate light on the surface of the photo responsive layer 337. The photo responsive layer 337 has higher responsivity to light as the area of the plane is wider.

In case that an auxetic hole pattern is formed in the photo responsive layer 337, the area decreases as much as the formed dumbbell/circular holes. Accordingly, the photo responsive layer 337 has lower need to form an auxetic hole pattern, and thus does not need to be built in the auxetic hole pattern of the flexible patch 60.

The specific through-hole in which the photo sensing unit 330 will be built is a through-hole formed in a specific other region that is different from the region in which the auxetic hole pattern is formed, and is an unmatched through-hole having a size and/or shape that is different from the circular hole or dumbbell hole of the other region. For example, the photo sensing unit 330 may be built in the specific through-hole of the flexible patch 60 having a larger size than the dumbbell/circular hole of the auxetic hole pattern of the flexible patch 60 of the other region to form a perforated pattern.

In an embodiment, the flexible patch 60 that will be positioned at the lower end of the photo sensing unit 330 may further include a supporter 630 connecting two ends in the plane of the specific through-hole. As shown in FIG. 16, the supporter 630 connects one end and the other end of a large through-hole. The supporter 630 of the flexible patch 60 supports at least part of the photo sensing unit 330.

In an embodiment, the second passivation layer 400 in contact with the photo sensing unit 330 may be configured to have a plurality of auxiliary through-holes 401.

Each auxiliary through-hole 401 is a through-hole formed in the upper passivation layer 400 formed in the specific region, not the region in which the auxetic hole pattern formed in the upper passivation layer 400 is formed. By the opening 401, the photo responsive layer 337 is not blocked all over the entire area by the upper passivation layer 400, and is partially exposed.

The auxiliary through-hole 401 may be smaller in size than the though-hole that forms the auxetic hole pattern.

Figure 17:
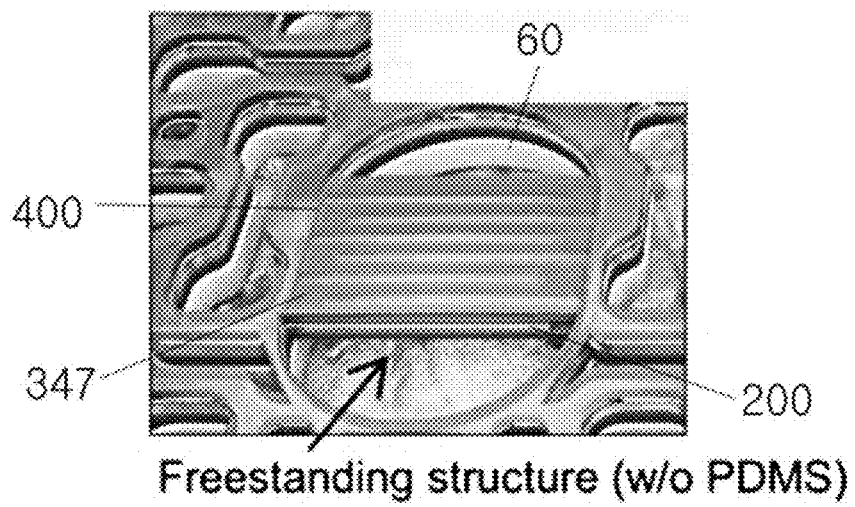
FIG. 17 is a schematic diagram of region 5 in which a strain sensing unit is built according to an embodiment of the present disclosure.

FIG. 17 is a schematic diagram of region 5 in which the strain sensing unit is built according to an embodiment of the present disclosure.

Referring to FIG. 17, the strain sensing unit 340 may be built in the specific through-hole of the flexible patch 60.

The specific through-hole in which the strain sensing unit 340 will be built is a through-hole formed in a specific other region that is different from the region in which the auxetic hole pattern is formed, and is an unmatched through-hole having a size and/or shape that is different from the circular hole or dumbbell hole of the other region. For example, the active layer 347 of the strain sensing unit 340 may be built in the specific through-hole of the flexible patch 60 having a larger size than the dumbbell/circular hole in the auxetic hole pattern of the flexible patch 60 of the other region for forming a perforated pattern as shown in FIG. 17.

The active layer 347 of the strain sensing unit 340 extends from the electrode 341 or 342 to the other electrode 342 or 341. The strain sensing unit 340 has a suspended freestanding structure. For example, the active layer 347 may be implemented as a cantilever structure extended from the electrode 341 or 342.

Part of the active layer 347 is positioned on the plane of the specific through-hole of the flexible patch 60. The cavity may be an internal space surrounded by the sidewalls of the specific through-hole of the flexible patch 60 such as furrow. As opposed to the photo sensing unit 330 supported by the supporter 630, the strain sensing unit 340 is not supported by the flexible patch 60.

When strain occurs in the skin, part of the free-standing structure bends in the cavity formed by the sidewalls of the specific through-hole of the flexible patch 60. All or part of a projection area of the bendable part in the free-standing structure may be included in the planar inner area of the specific through-hole.

The specific through-hole in which the strain sensing unit 340 is built may be different from the specific through-hole in which the photo sensing unit 330 is built. As shown in FIG. 2, the strain sensing unit 340 may be built in region 5 that is different from region 4 in which the photo sensing unit 330 is installed.

The skin sensor device 1 having the sensing unit 310, 320, 330 and/or 340 may have high adhesion, air permeability and durability, and obtain various types of skin related information skin such as temperature information, moisture information, light information and strain information of the skin.

FIGS. 18A to 18D are partial enlarged views of regions 2 to 5 of FIG. 2. FIGS. 19 to 22 are diagrams illustrating the performance for each sensing unit included in the skin sensor device 1 of FIG. 18.

As shown in FIGS. 18A to 18D, when the sensor module 30 includes the sensing units 310, 320, 330, 340, the skin sensor device 1 may obtain information associated with the user's skin condition (the temperature information, hydration information, stain information and/or light information), in the regions 2, 3, 4, 5 of the skin in which each sensing unit 310, 320, 330, 340 is built.

Figure 18A:
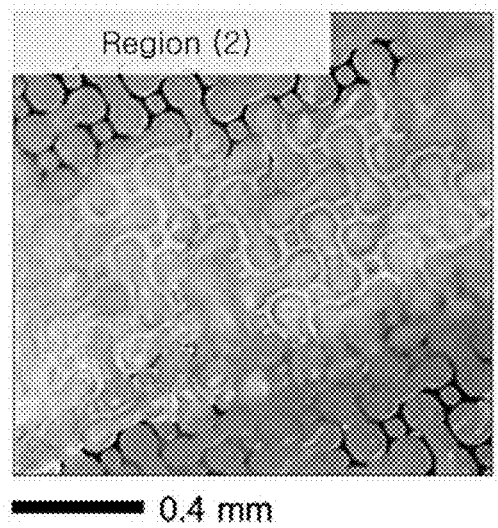
FIGS. 18A to 18D are partial enlarged views of the regions 2 to 5 of FIG. 2.
Figure 19:
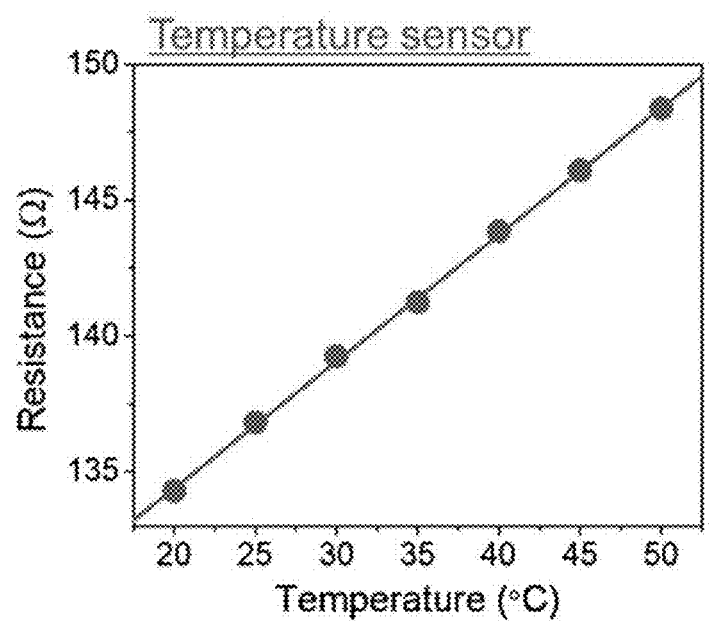
FIG. 19 shows the temperature sensing performance of a skin sensor device including the temperature sensing unit of FIG. 18A.

FIG. 19 shows the temperature sensing performance of the skin sensor device including the temperature sensing unit of FIG. 18A.

As shown in FIG. 19, the temperature responsive layer 317 (for example, the Pt thin film layer) of the temperature sensing unit 310 changes in electrical properties such as resistance in response to a change in temperature around the skin. The temperature responsive layer 317 has the electrical properties that the resistance characteristics change with change in temperature. Using this predetermined correlation, the skin sensor device 1 may be used as a sensor device for monitoring temperature information.

Figure 18B:
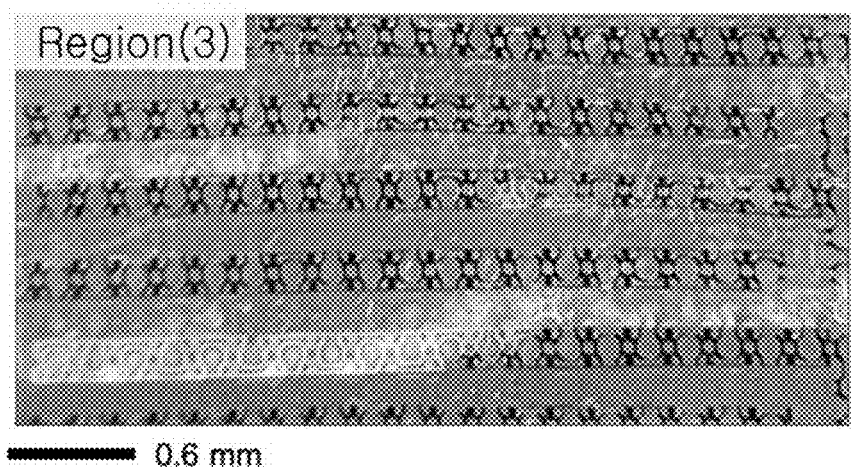
Figure 20:
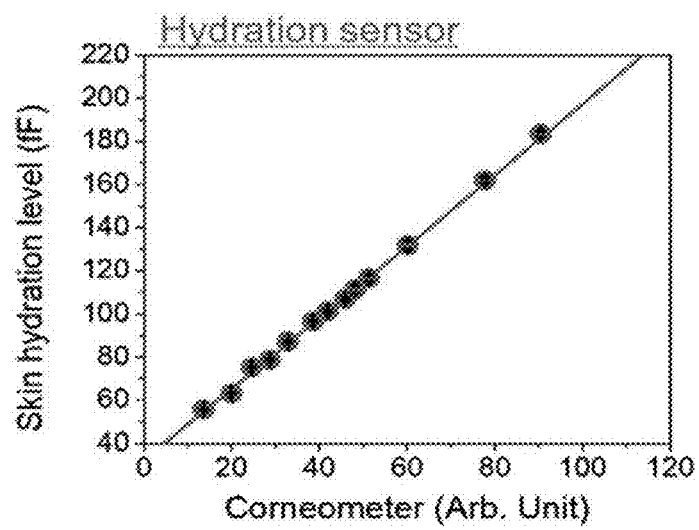
FIG. 20 shows the moisture sensing performance of a skin sensor device including the hydration sensing unit of FIG. 18B.

FIG. 20 shows the moisture sensing performance of the skin sensor device including the hydration sensing unit of FIG. 18B.

FIG. 20 is a graph obtained using the moisture sensing performance of the existing moisture sensor device (Courage Khazaka electronic Corneometer CM-825, Germany) and the skin sensor device 1 of FIG. 18 including the hydration sensing unit 320. The moisture sensing performance of the existing moisture sensor device is indicated by a line, and the sensing results of the skin sensor device 1 including the hydration sensing unit 320 are indicated by points.

Referring to FIG. 20, the hydration responsive layer 327 (for example, the Pt thin film layer) of the hydration sensing unit 320 changes in capacitance values of the hydration sensing unit 320 in response to a change in hydration around the skin. The hydration responsive layer 327 has the electrical properties that the capacitance value change with change in moisture. Using this predetermined correlation, the skin sensor device 1 may be sufficiently used as a sensor device for monitoring moisture information. In particular, as shown in FIG. 20, the correlation of the hydration sensing unit 320 matches the performance trend of the existing hydration sensing device, and thus it is found that the skin sensor device 1 including the hydration sensing unit 320 has the equivalent sensing performance to the performance of the existing hydration sensing device.

Figure 18C:
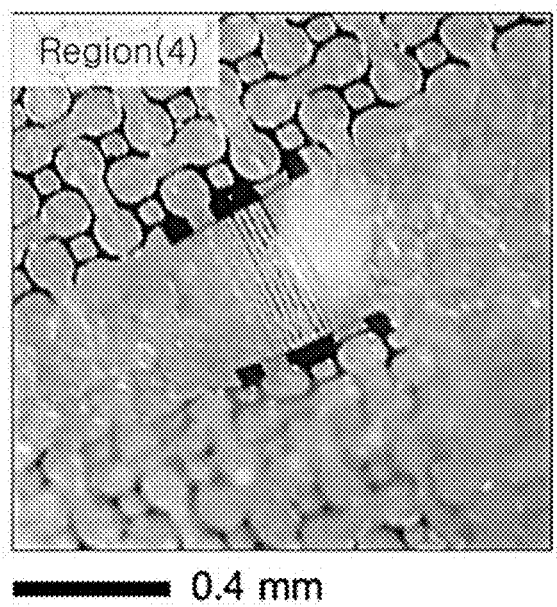
Figure 18D:
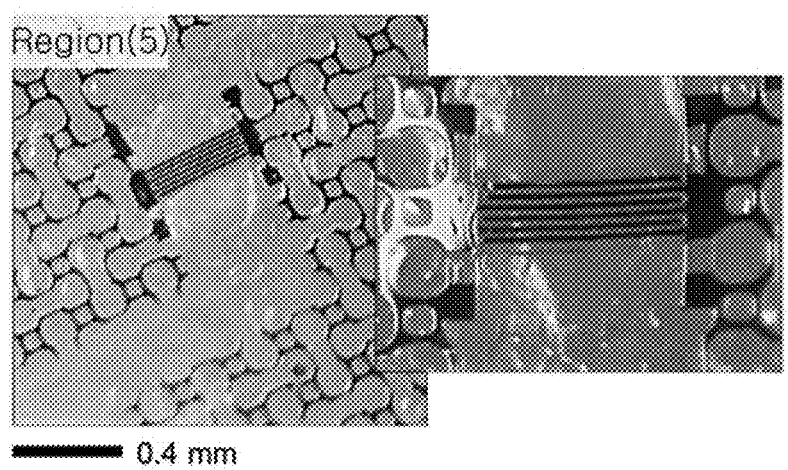
Figure 21A:
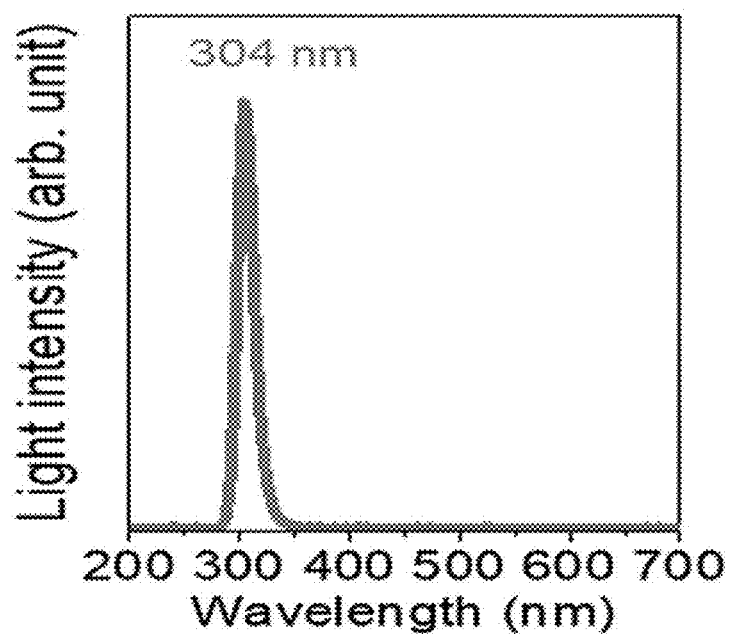
FIG. 21A shows the response of the photo sensing unit of FIG. 18C to a specific band of light.
Figure 21B:
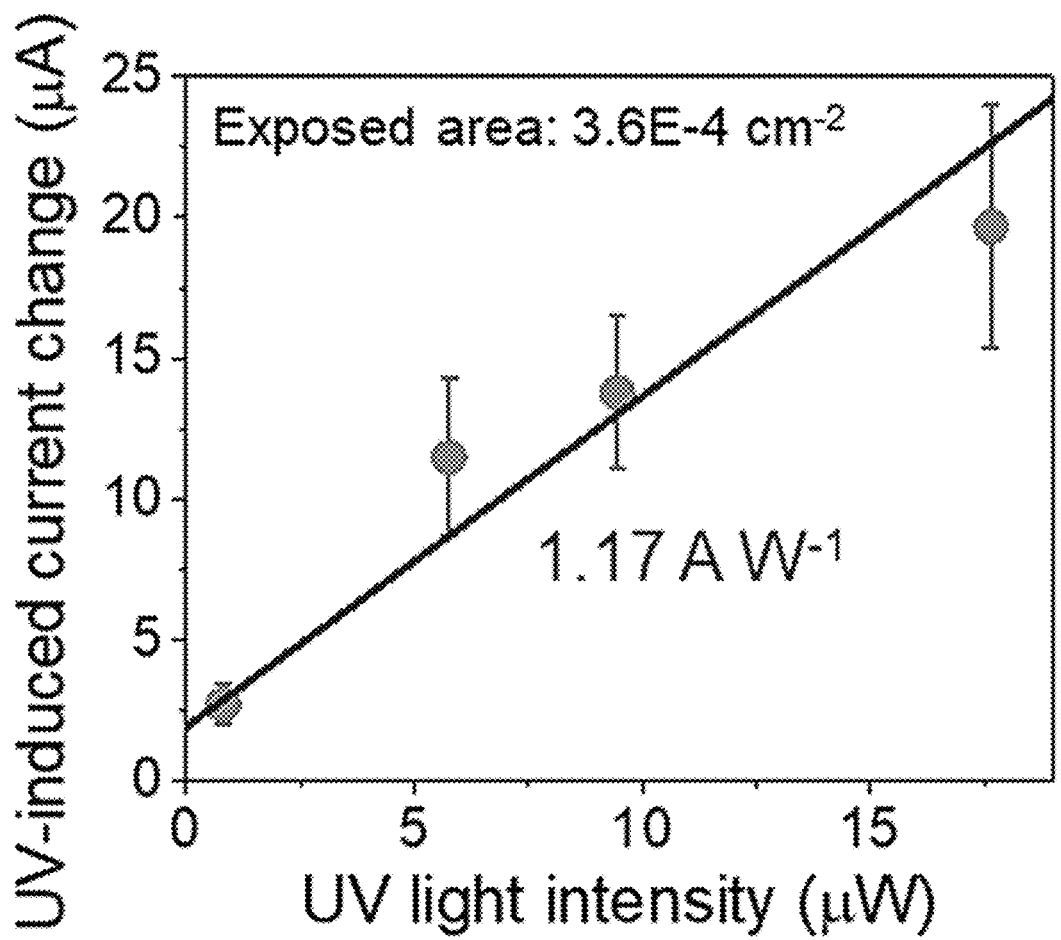
FIG. 21B shows electric current generation by the photo sensing unit of FIG. 18C as a function of light intensity.
Figure 21C:
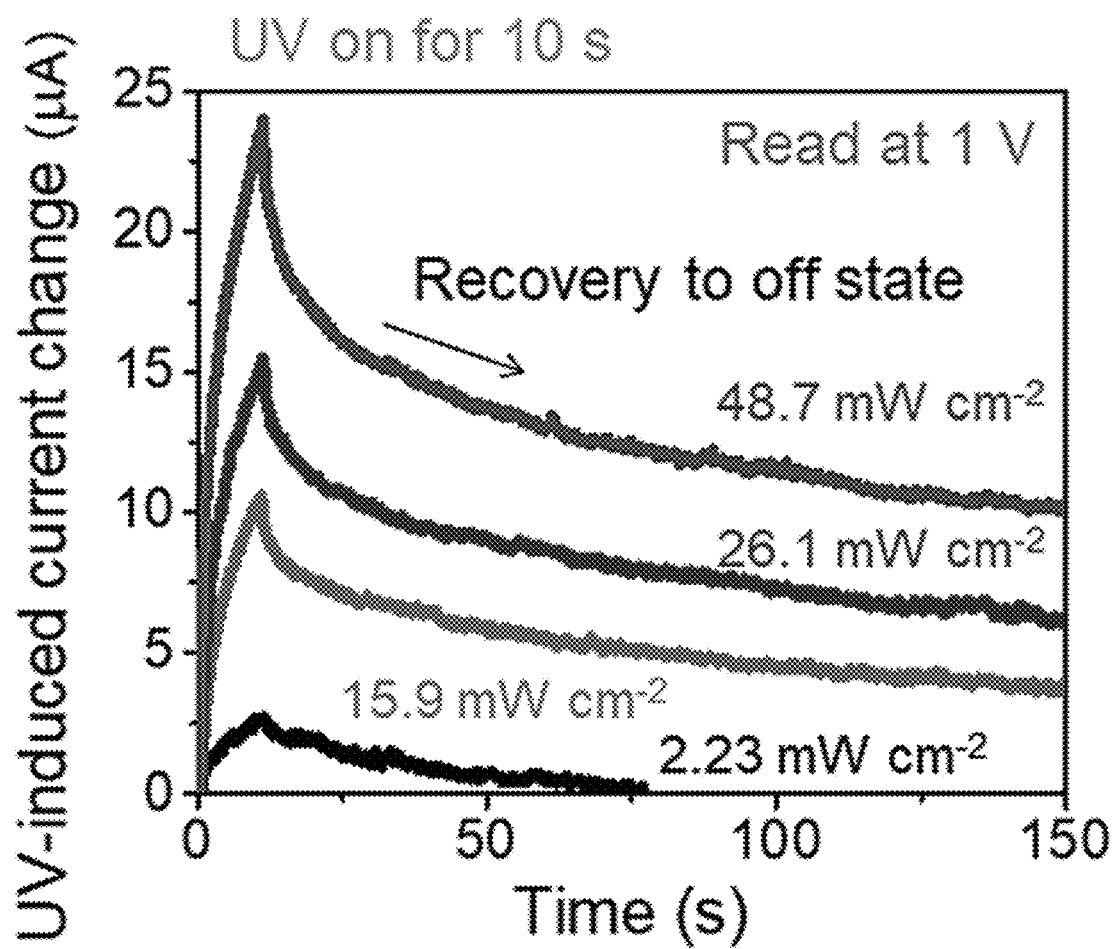
FIG. 21C is a diagram illustrating the response speed of the photo sensing unit of FIG. 18C.

FIGS. 21A to 21C show the UV sensing performance of the skin sensor device including the photo sensing unit of FIG. 18C. The photo sensing unit 330 of FIG. 18C includes a ZnO thin film as the photo responsive layer 337.

FIG. 21A shows the response of the photo sensing unit of FIG. 18C to a specific band of light.

Referring to FIG. 21A, the skin sensor device 1 including the photo sensing unit 330 may sense if light irradiated on the skin includes the UV band component. It is found that when light is irradiated on the skin, the responsivity and switching speed of the photo sensing unit 330 including the photo responsive layer 337 sharply changes in the specific wavelength band (for example, about 300 nm). Accordingly, when the responsivity and switching speed of the photo sensing unit 330 changes, the skin sensor device 1 may sense light irradiation on the skin.

FIG. 21B shows electric current generation of the photo sensing unit of FIG. 18C as a function of light intensity. FIG. 21C is a diagram illustrating the response speed of the photo sensing unit of FIG. 18C.

Additionally, referring to FIGS. 21B and 21C, the skin sensor device 1 including the photo sensing unit 330 may measure the intensity of light irradiated on the skin. The photo sensing unit 330 may generate the electric current that changes as a function of the light intensity.

When UV light having the maximum UV peak wavelength of 304 nm is irradiated with the light intensity of 2.23-48.7 mW cm$^{-2}$ for approximately 10 seconds, the photo electric current of the photo sensing unit 330 changes as a function of the light intensity as shown in FIG. 21B. When the intensity of irradiated light differs, the photo electric current value also differs in response.

The responsivity of the skin sensor device 1 including the photo sensing unit 330 is extracted from the photo electric current change and the slope of a UV light intensity curve as indicated in FIG. 21C. Referring to FIGS. 21A to 21C, the responsivity of the skin sensor device 1 is 1.17 AW$^{-1}$. The skin sensor device 1 having the device characteristics such as responsivity may be sufficiently used as a sensor device for monitoring light information.

Figure 22:
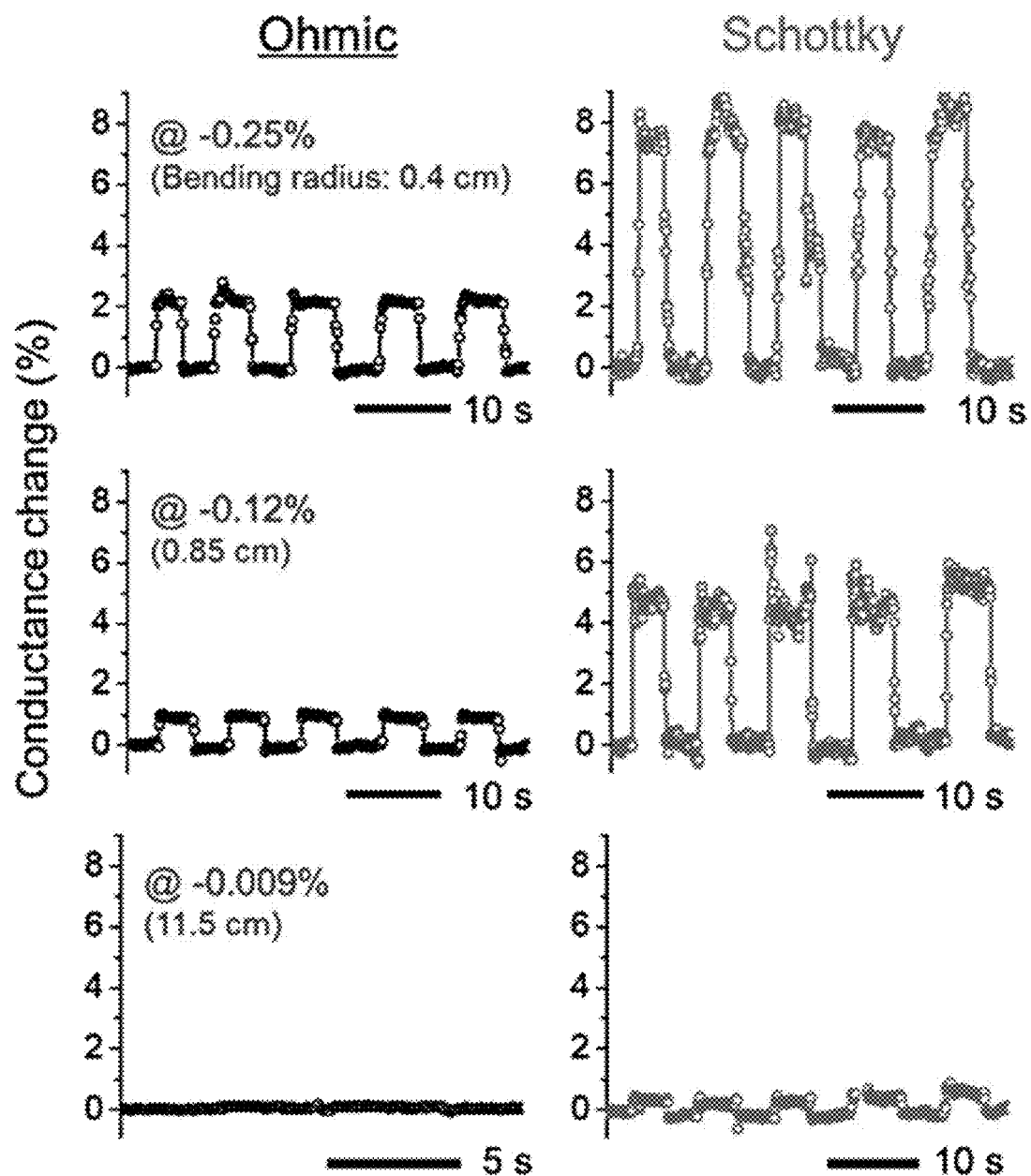
FIG. 22 shows the strain sensing performance of a skin sensor including a strain sensing unit according to an embodiment.

FIG. 22 shows the strain sensing performance of the skin sensor including the strain sensing unit according to an embodiment. FIG. 22 is a graph the influence of Schottky contact on bending responsivity, obtained using the skin sensor device 1 including the active layer 347 of polycrystalline ZnO.

Referring to FIG. 22, the strain sensing unit 340 changes in semiconductor properties when skin strain occurs. It is found that as the strain level of the active layer 347 gradually increases to 0.009%, 0.12%, 0.25%, a conductance change increases. Accordingly, the skin sensor device 1 including the strain sensing unit 340 can be sufficiently used as a sensor device for sensing skin strains.

Figure 23:
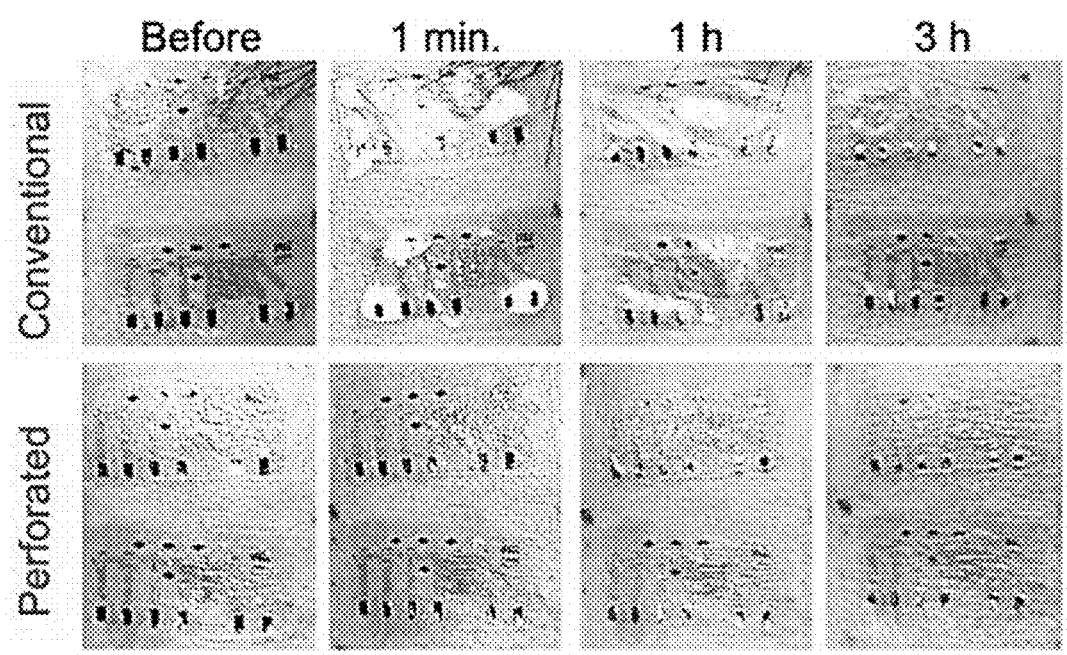
FIG. 23 is an image of a skin sensor device attached to a user's skin over time during sweating in the skin according to an embodiment.

FIG. 23 is an image of the skin sensor device attached to the user's skin over time during sweating in the skin according to an embodiment. FIGS. 24A to 24F show the monitoring results by the skin sensor device of FIG. 23.

In the process of monitoring the user's skin condition for a long time, the skin sensor attached to the skin inevitably contacts sweat coming from the user's skin. To maintain long-term accurate monitoring, it is necessary to prevent the skin sensor from delaminating due to sweat and causing damage to the skin.

Referring to FIG. 23, as opposed to the existing skin sensor, the skin sensor device 1 of the present disclosure has no sweat accumulation at the interface between the skin sensor device 1 and the skin by high air permeability in the presence of the auxetic hole pattern. It is because air permeability is maintained by the perforated pattern. The skin sensor device 1 having no sweat accumulation keeps in close contact with the skin.

Figure 24A:
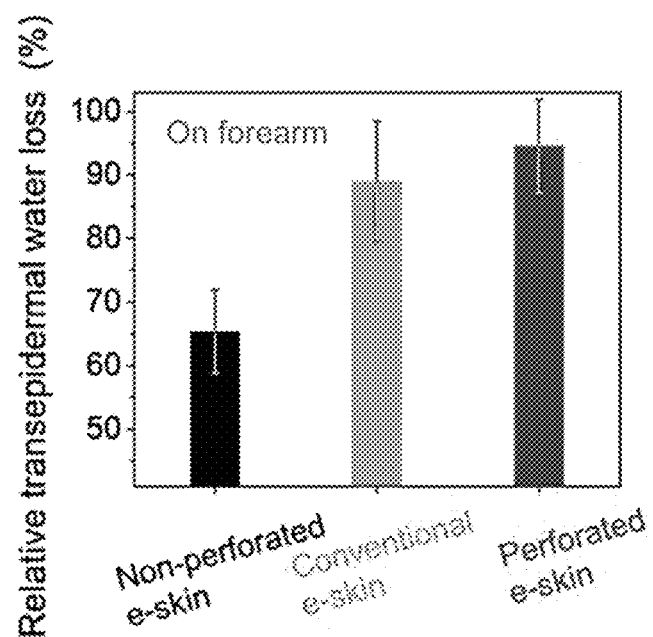
FIGS. 24A to 24F show the monitoring results by the skin sensor device of FIG. 23.

In contrast, as shown in FIGS. 23 and 24A, the existing skin sensor having no perforated pattern has more sweat accumulation at the interface with the skin. Thus, the existing skin sensor cannot manage sweat accumulation and eventually is separated.

Figure 24B:
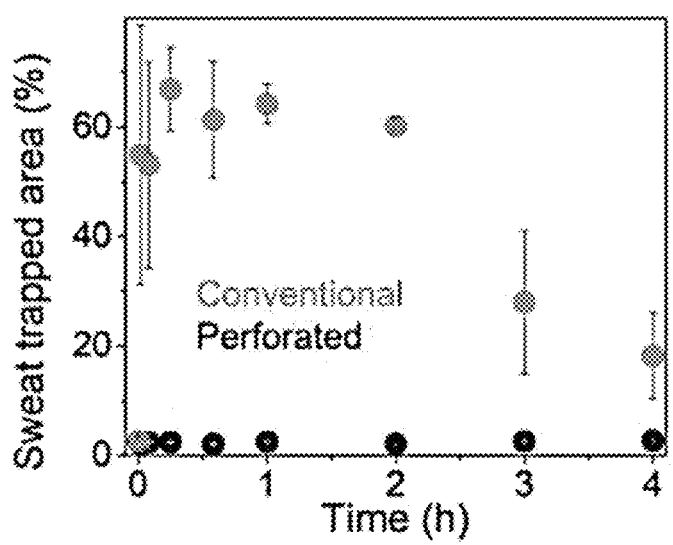

Referring to FIG. 24B showing the result of measuring by the image analyzer, quantitative analysis on sweat trapped area confirms that sweat is trapped below the existing skin sensor, while sweat is effectively evacuated from the skin sensor having the perforated pattern.

Figure 24C:
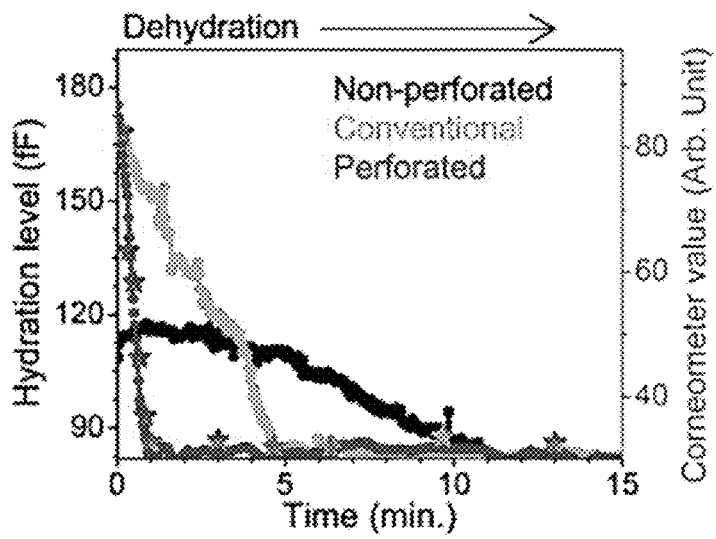

Additionally, referring to FIG. 24C, the skin sensor device 1 having the perforated pattern immediately senses the hydration level of the skin, as consistent with the estimated results by a commercial hydration sensor (Corneometer CM 825). In contrast, the existing skin sensor having no perforated pattern has the delayed sensing operation. Based on FIG. 24C, as opposed to the existing skin sensor that allows only vapor exchange, the skin sensor having the perforated pattern allow both vapor and liquid permeation.

Figure 24D:
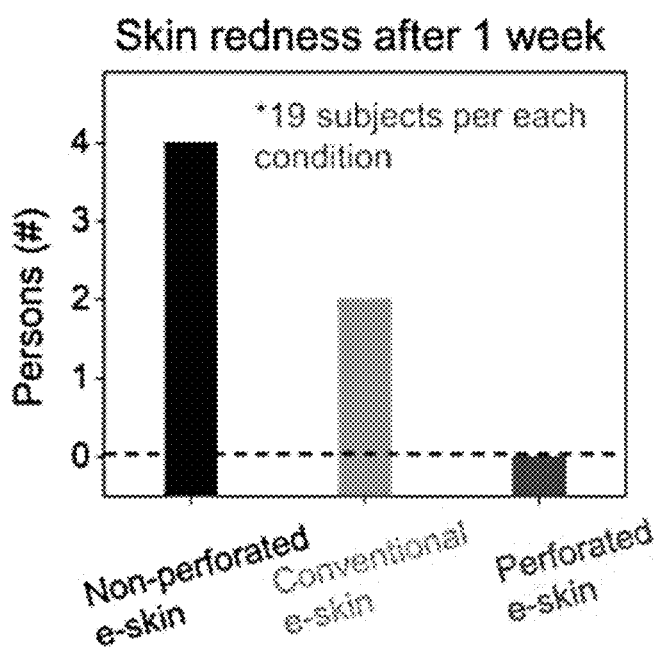

For long-term monitoring, it is necessary to consider skin allergic reaction. FIG. 24D shows the result of monitoring skin allergic reaction by a dermatologist after laminating onto the forearm over a period of 1 week. Referring to FIG. 24D, users wearing the existing nonperforated skin sensor show skin damage, while none of users wearing the skin sensor device 1 having the perforated pattern show skin irritation. Accordingly, the skin sensor device 1 has excellent long-term skin compatibility.

Figure 24E:
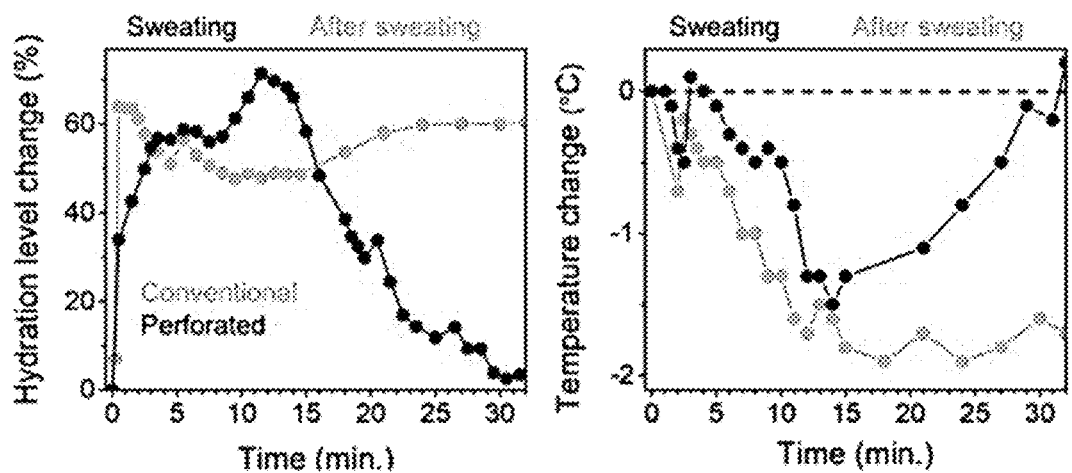

Referring to FIG. 24E, after the user sweats, the skin sensor device 1 having the perforated pattern accurately monitors the hydration and temperature response. In contrast, the existing skin sensor cannot accurately monitor the hydration and temperature response due to malfunction of the skin sensor. As shown in FIG. 24E, in the skin sensor device 1 of the present disclosure, the measured hydration level/temperature level shows the increased skin hydration and the decreased body temperature by perspiration. That is, the skin sensor device 1 of the present disclosure measures successful relaxation of the hydration and temperature values after sweating. However, the hydration and temperature values of the existing skin sensor do not obey the current hydration and temperature values of the skin any longer after sweating.

Figure 24F:
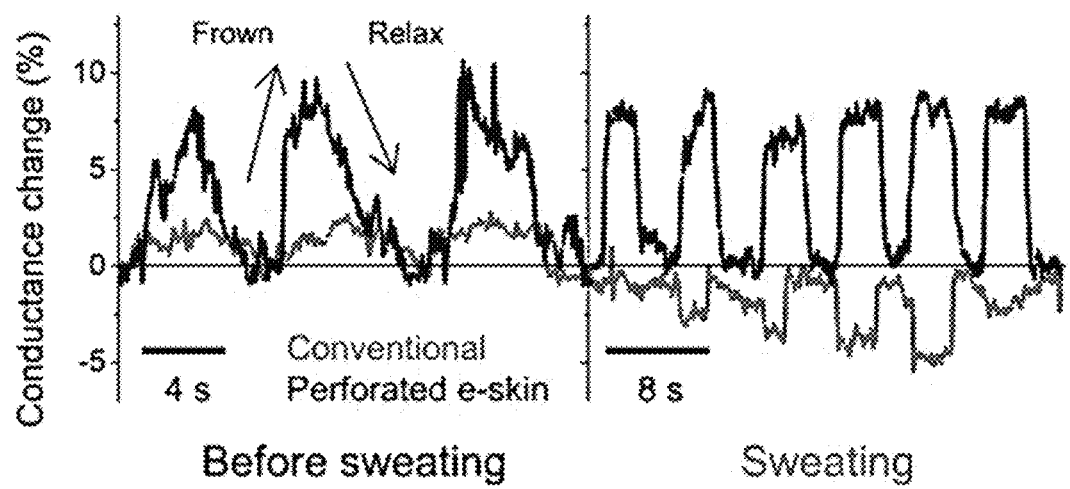

Referring to FIG. 24F, the skin sensor device 1 having the perforated pattern can accurately measure skin strains since sweat is not trapped. In contrast, the existing skin sensor cannot accurately measure strains due to trapped sweat.

Before sweating, the two sensors accurately monitor tension and relaxation when frowning or relieving. However, after sweating, only the skin sensor of the present disclosure accurately monitors strains without malfunction. In particular, the suspended free-standing structure (for example, the cantilever structure) of the strain sensor reduces the flexural rigidity of the sensing area, thereby suppressing the strain damping effect of the flexible patch 60, and thus the skin sensor device 1 having the perforated pattern has higher strain responsivity (approximately 4 times).

Figure 25:
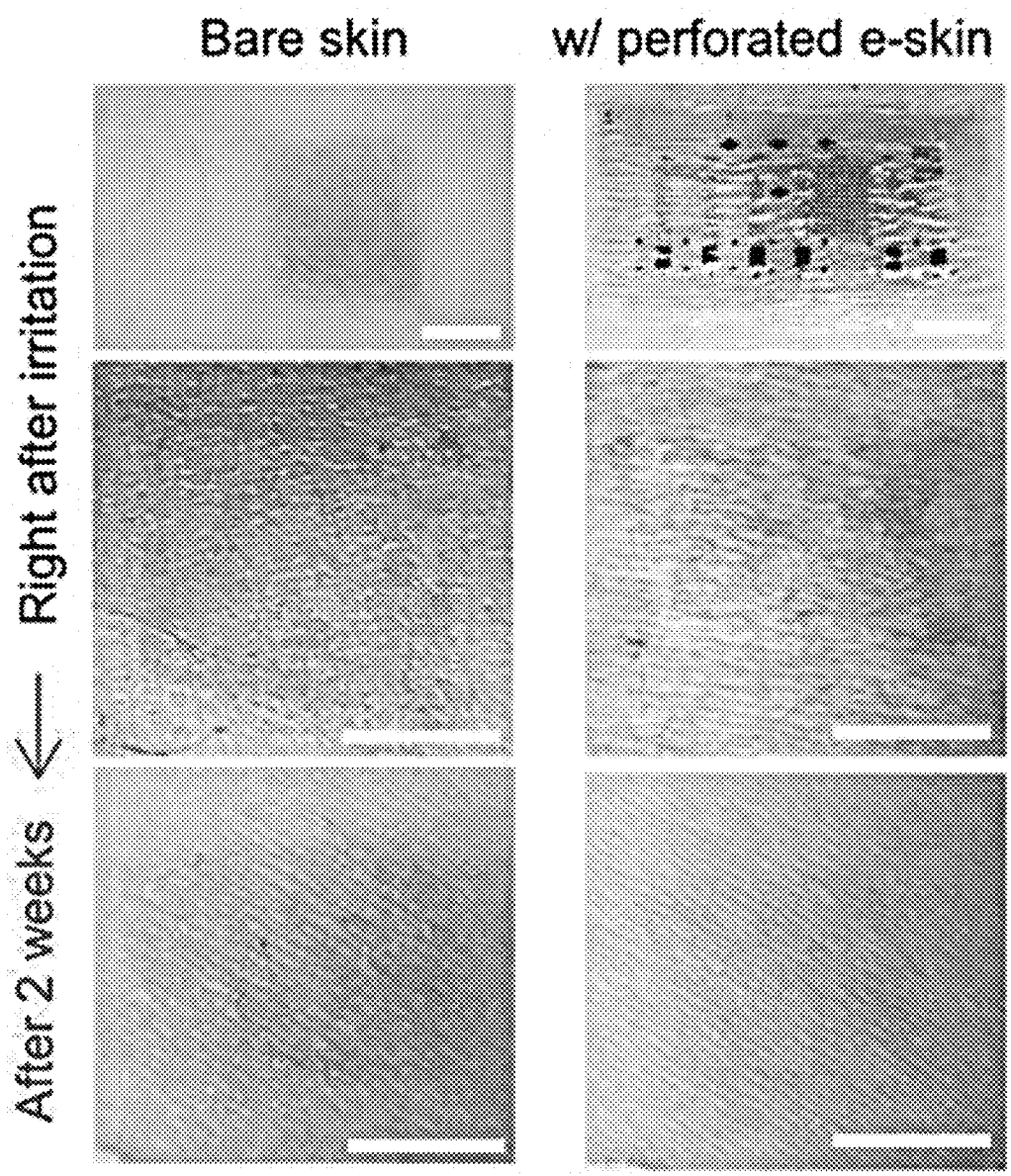
FIG. 25 is an image of a process of monitoring the extent of recovery of skin to which a skin sensor device is attached.
Figure 26:
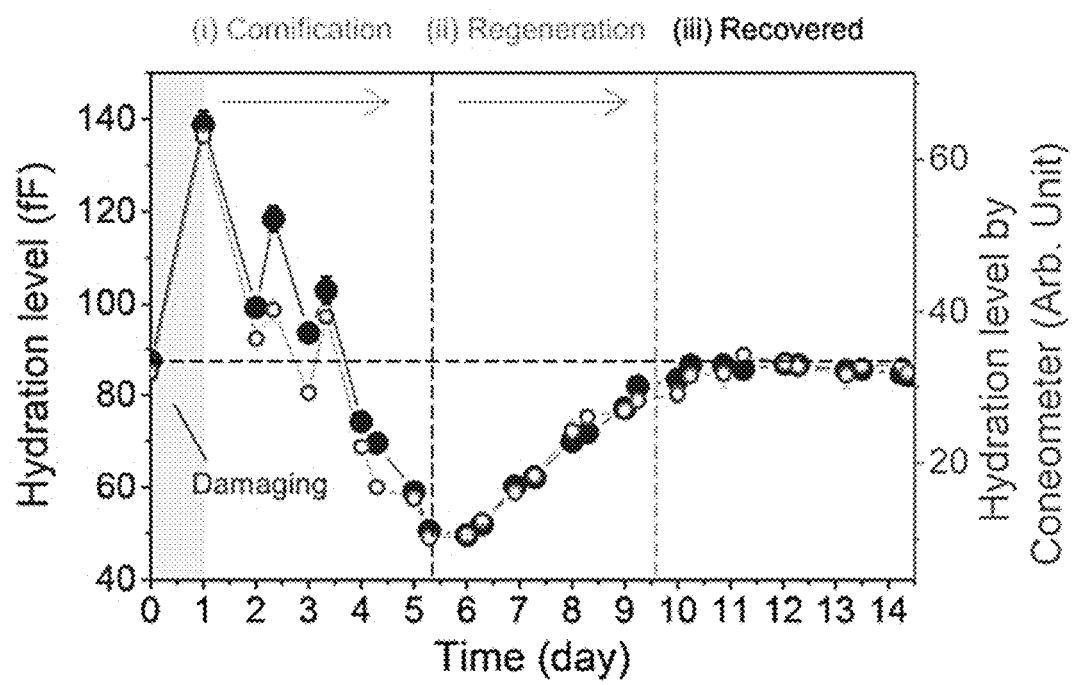
FIG. 26 shows the monitoring results of FIG. 25.

FIG. 25 is an image of a process of monitoring the extent of recovery of the skin to which the skin sensor device is attached. FIG. 26 shows the monitoring results of FIG. 25.

Referring to FIGS. 25 and 26, the skin sensor device 1 does not impede the recovery of damaged skin when attached to the skin due to high air permeability.

The monitoring results of FIGS. 25 and 26 are obtained by continuously monitoring the skin hydration level for 2 weeks using the skin sensor having the perforated pattern of the present disclosure as a hydration sensor after causing red spots on the skin by applying a Sodium Lauryl Sulfate (SLS) solution.

The result of measuring the moisture level of the control area using Cutometer (Corneometer) without the skin sensor device 1 is used as control. As a result, it is found that the skin sensor device 1 maintains long-term sensing accuracy for 2 weeks.

As shown in FIG. 26, the result of measuring the recovery of damaged skin shows three stages: i) keratinization due to dehydration, ii) restoration to normal hydration level and regeneration, iii) recovery of maintaining normal hydration level. The skin area that contacts the skin sensor device 1 having the perforated pattern shows skin recovery track for 2 weeks in the same way as measured by Cutometer (Corneometer) while the skin is covered with the patch of the skin sensor device 1. This signifies i) the perforations prevent the wound healing process from being prohibited by the skin sensor device 1 attached to the skin due to the full exposure of sweat pores to the external environment, and ii) the skin sensor device 1 can continuously monitor the skin condition of two persons as a hydration sensor.

Figure 27:
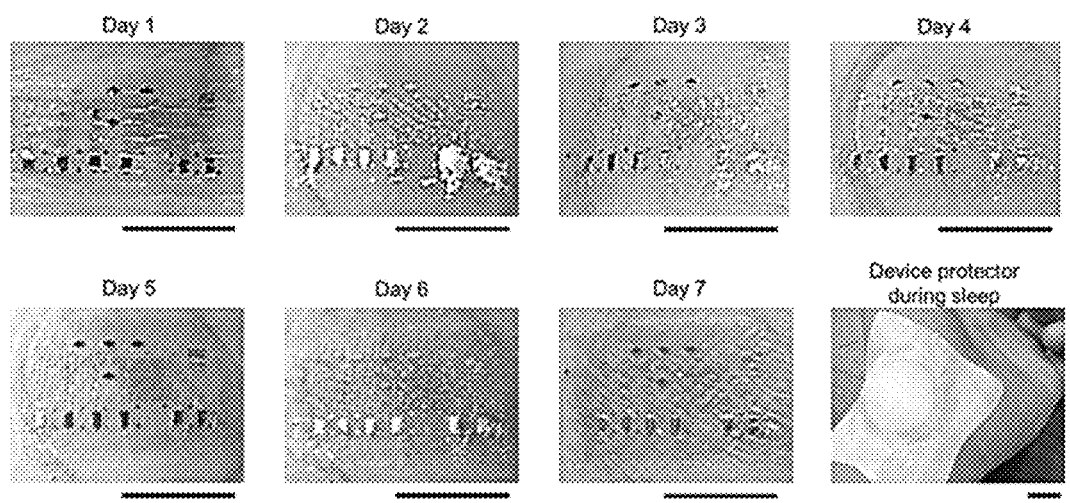
FIG. 27 is an image of a skin sensor device attached for a long time according to an embodiment of the present disclosure.
Figure 28A:
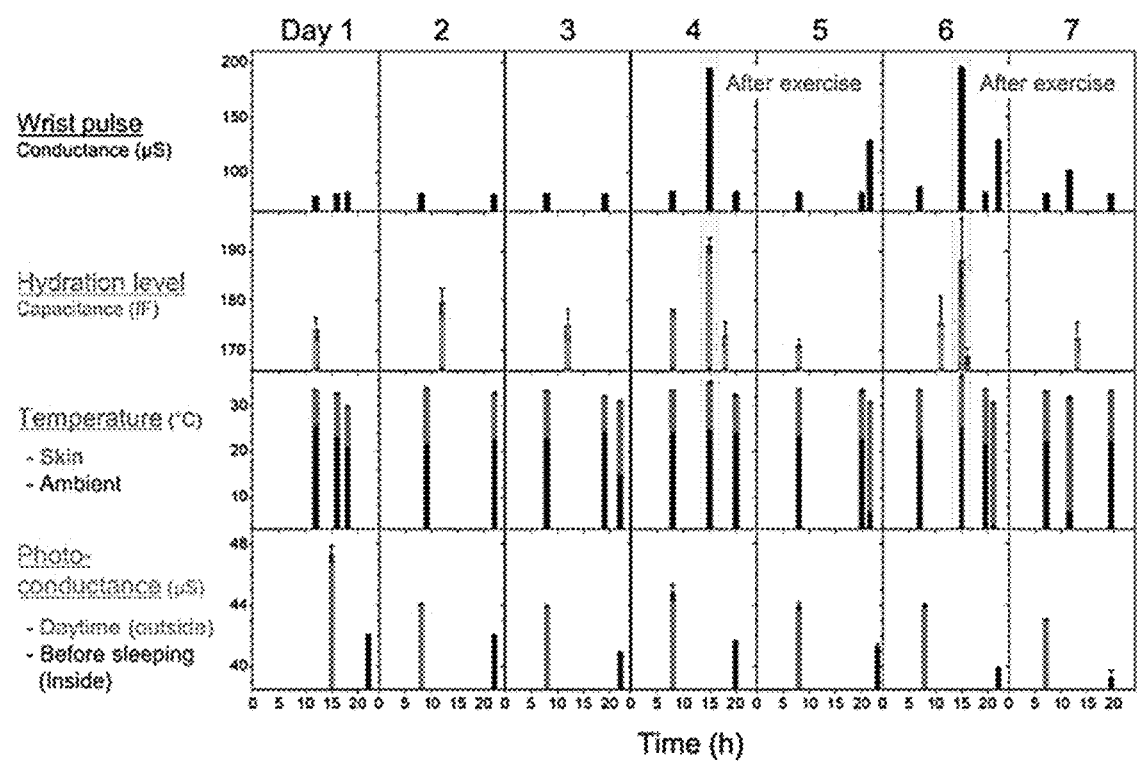
FIGS. 28A and 28B show the skin monitoring results of FIG. 27 over time.
Figure 28B:
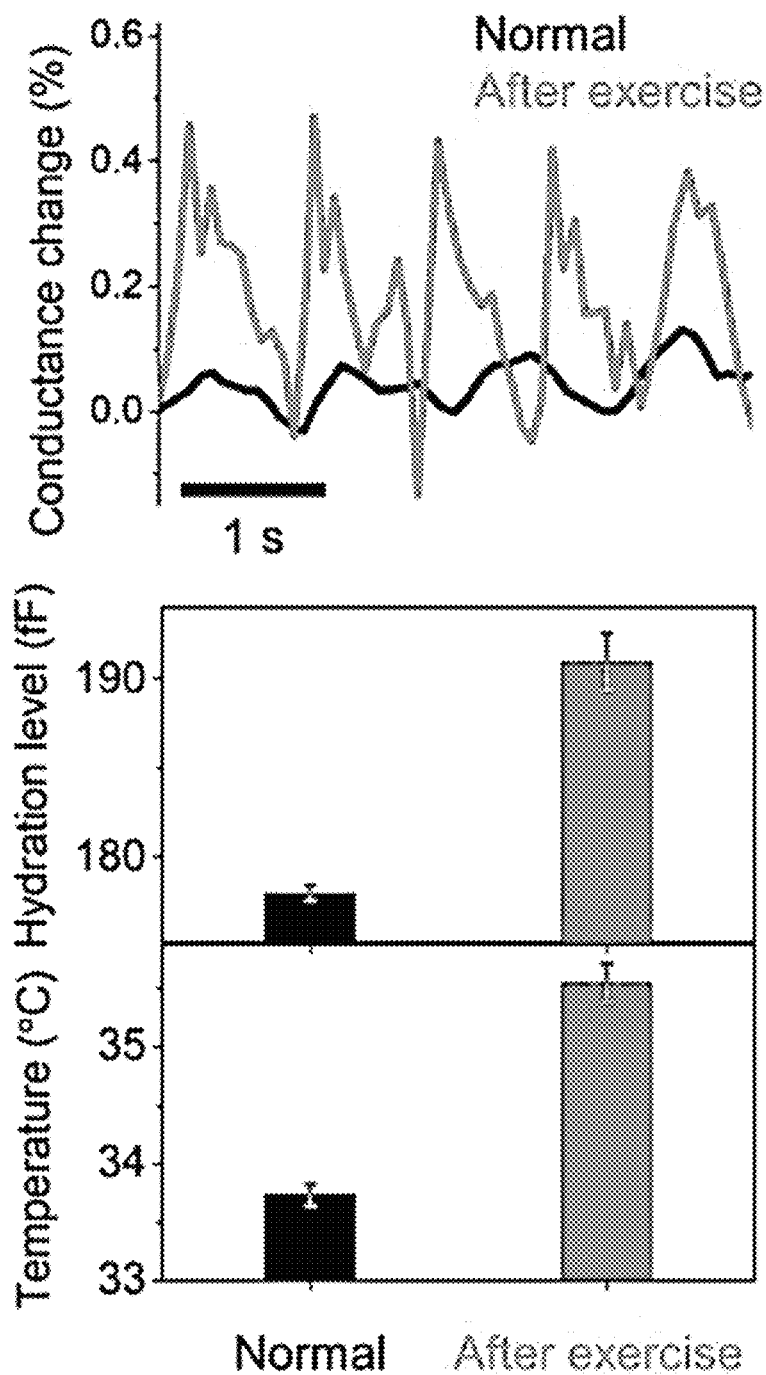

FIG. 27 is an image of the skin sensor device 1 attached for a long time according to an embodiment of the present disclosure. FIGS. 28A and 28B show the skin monitoring results of FIG. 27 over time.

The skin sensor of FIGS. 28A and 28B is attached to the user's wrist for a week. The skin sensor measures the wrist pulse, skin hydration level, skin temperature and light exposure level for a week.

As the skin sensor device 1 continuously monitors information for a week, it is found that the skin sensor device 1 does not delaminate from the skin.

Additionally, the skin sensor device 1 continuously monitors activity information of the skin without malfunction for seven days as shown in FIG. 28A. When the user runs for 30 minutes on the fourth day and the sixth day, increases in the number/intensity of pulse and moisture supply are accurately measured by the strain sensing unit and the hydration sensing unit as shown in FIG. 28B. It is intuitively understood from the graph of FIG. 28B that the heartbeat increases and sweat is produced during activities. Except the running event, the wrist pulse, skin hydration level and skin temperature level are almost uniform. For example, the user's monitoring results include beats per minute (BPM) of 51, skin hydration level of ~87 keratometry value and skin temperature information of 33.7° C. Additionally, time-space information of an object is distinctly distinguished due to a difference in photoconductivity between an external environment (exposure to the Sun) during the day and home (no light) before sleeping.

Based on the results of FIG. 28, the skin sensor device 1 may obtain skin related information including wrist pulse, hydration, temperature and exposure to light using multiple sensing units embedded into the perforated patch. As a result, the skin sensor device 1 may work as all electronic modules for long-term skin information monitoring.

In the skin sensor device 1 attached to the skin surface, the sensor module 30 that performs the sensor operation is disposed on the flexible patch 60. As opposed to the commonly used circuit boards, the flexible patch 60 is soft and sticky. Accordingly, it is difficult to fabricate the skin sensor device 1 of the present disclosure simply by the process of integrating the circuit components on the substrate in a sequential order.

A method for fabricating the skin sensor device 1 according to another aspect of the present disclosure may place the sensor module 30 on the flexible patch 60 more easily.

Figure 29A:
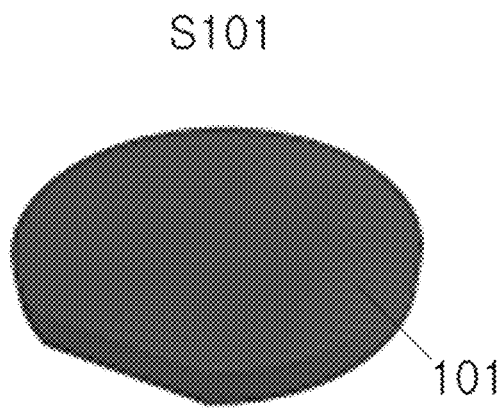
FIGS. 29A to 29O are schematic flowcharts of a method for fabricating a skin sensor device according to another aspect of the present disclosure.
Figure 29B:
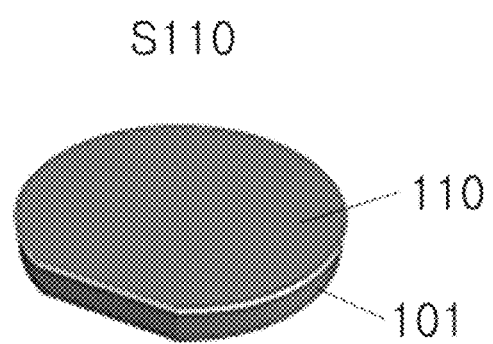
Figure 29C:
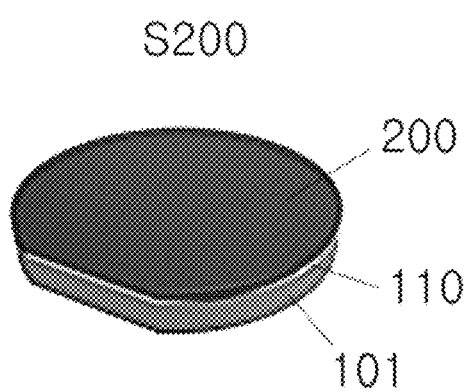
Figure 29D:
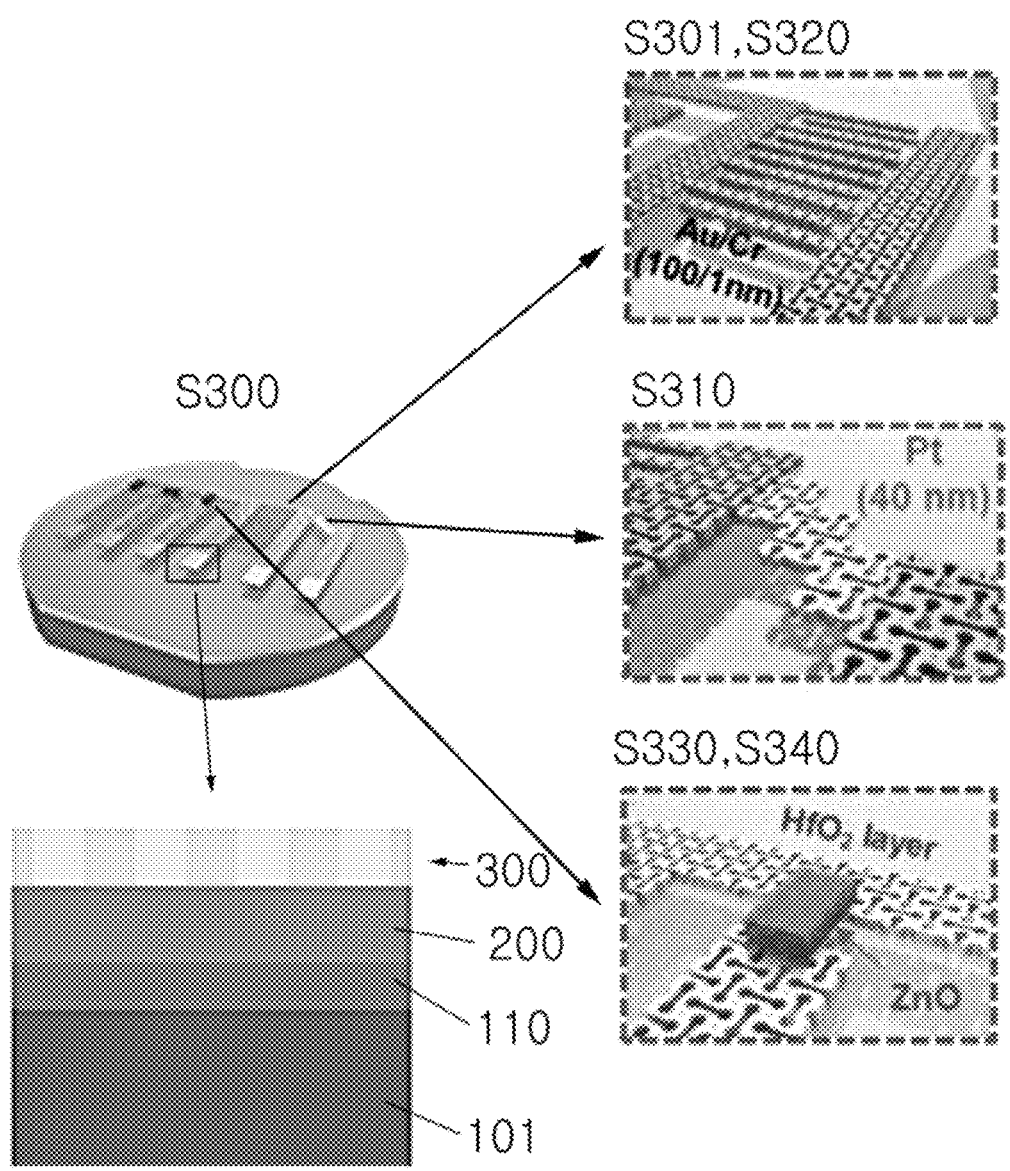
Figure 29E:
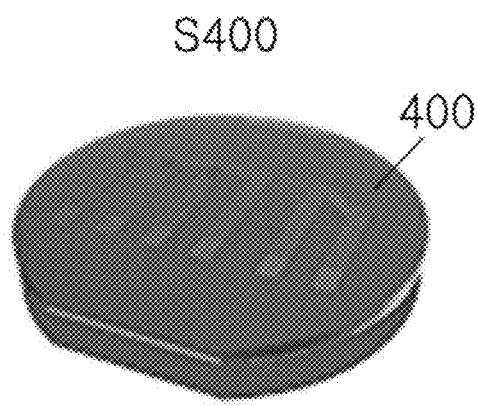
Figure 29F:
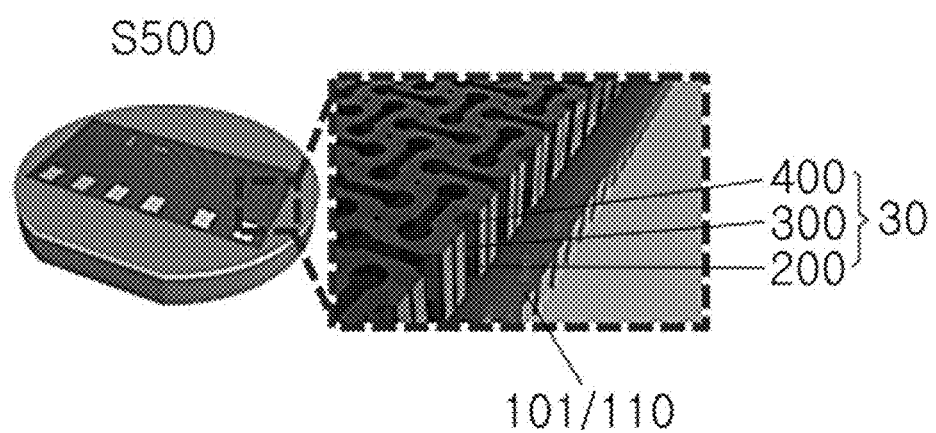
Figure 29G:
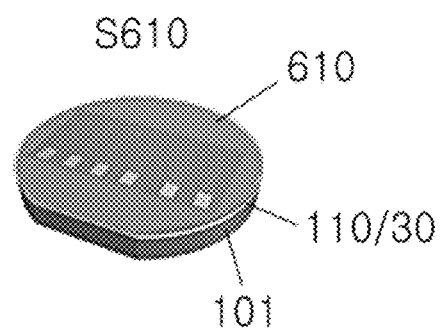
Figure 29H:
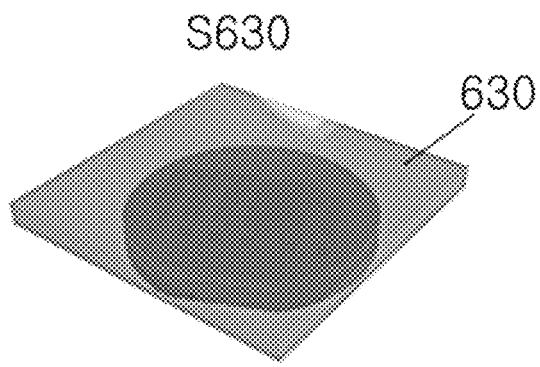
Figure 29I:
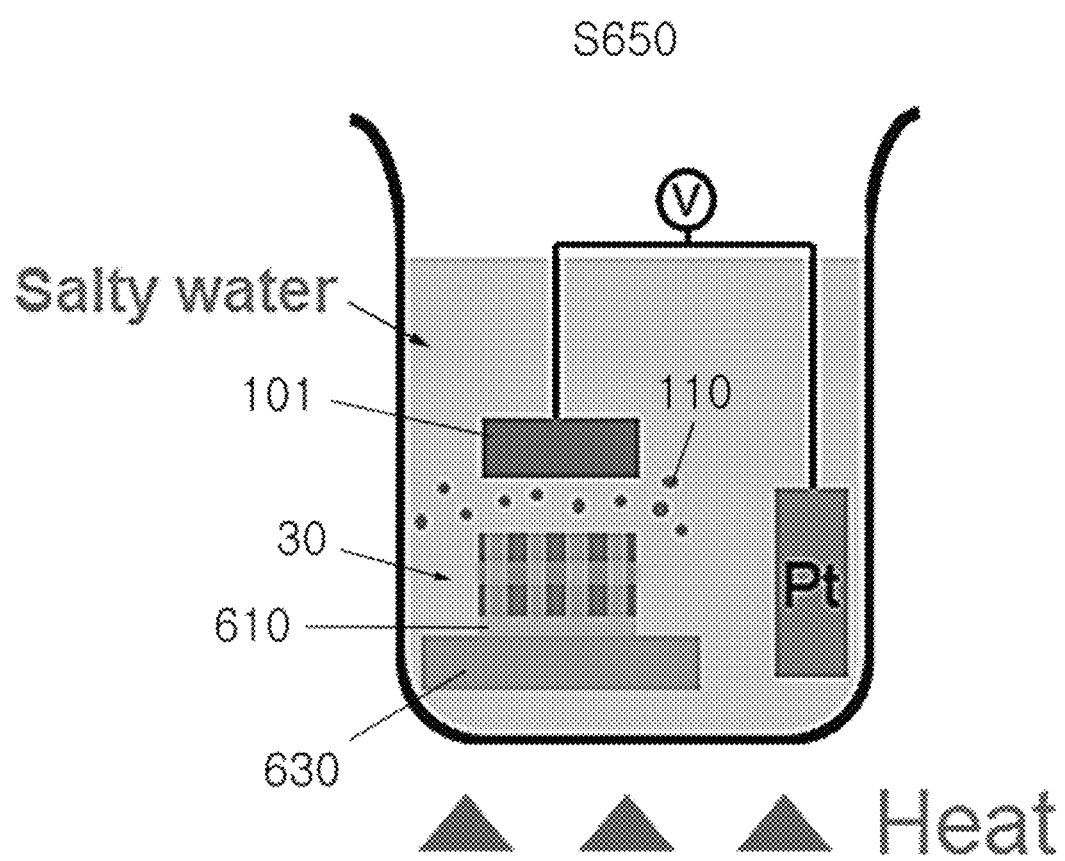
Figure 29J:
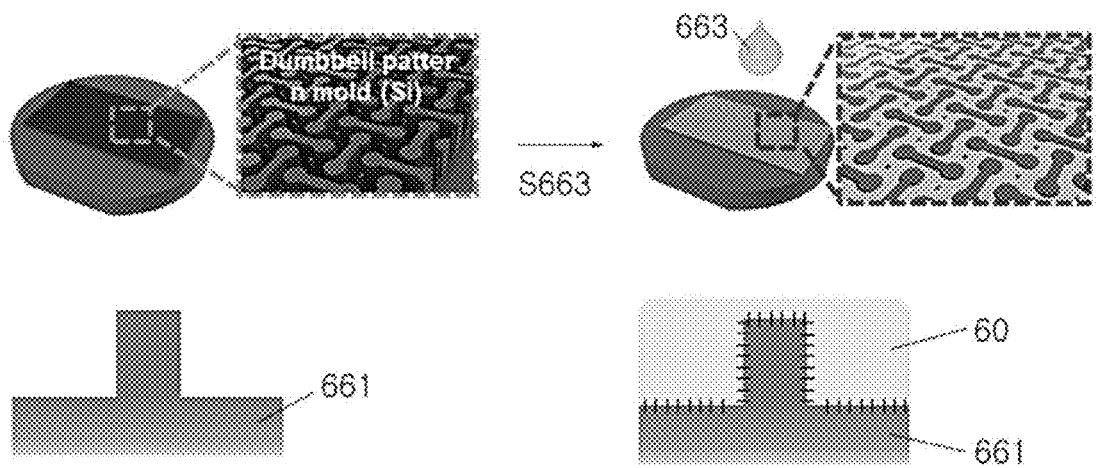
Figure 29K:
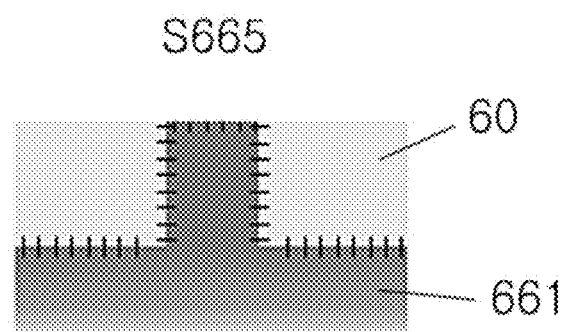
Figure 29L:
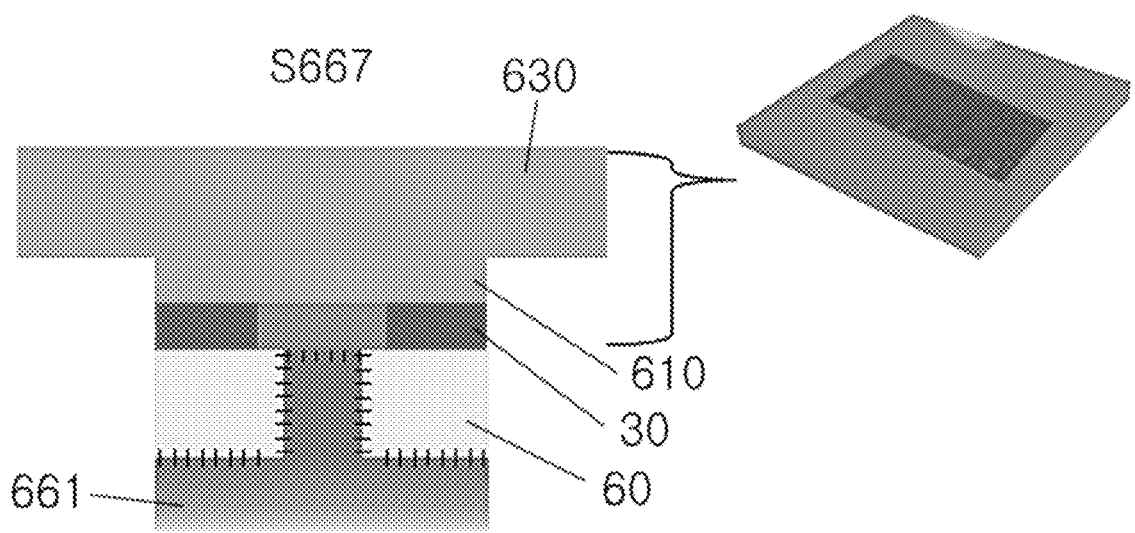
Figure 29M:
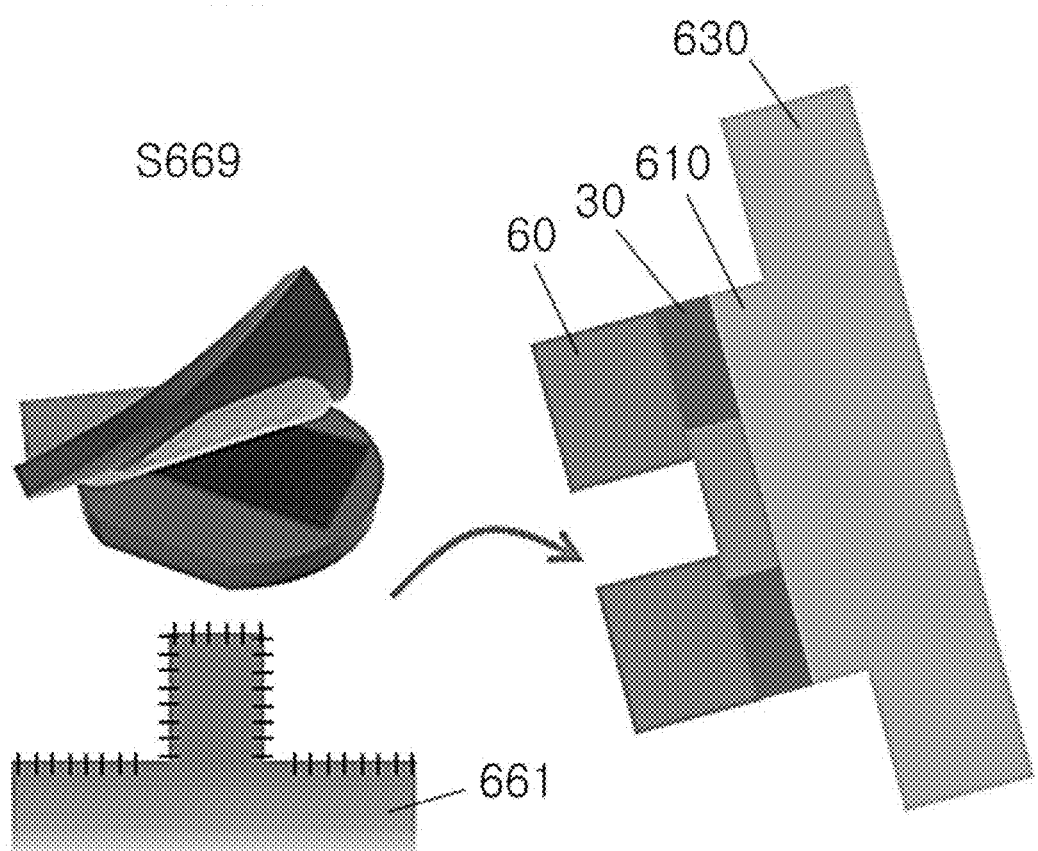
Figure 29N:
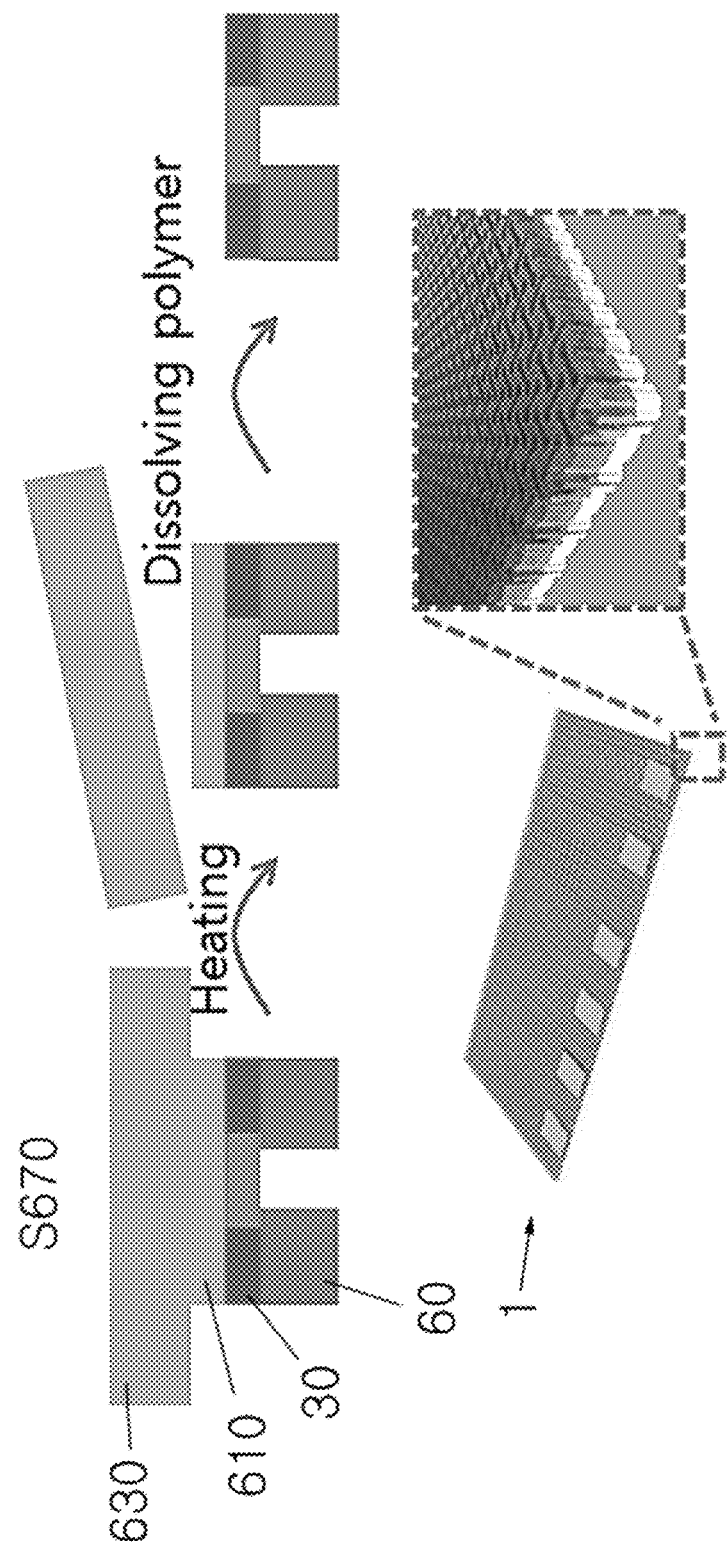
Figure 29O:
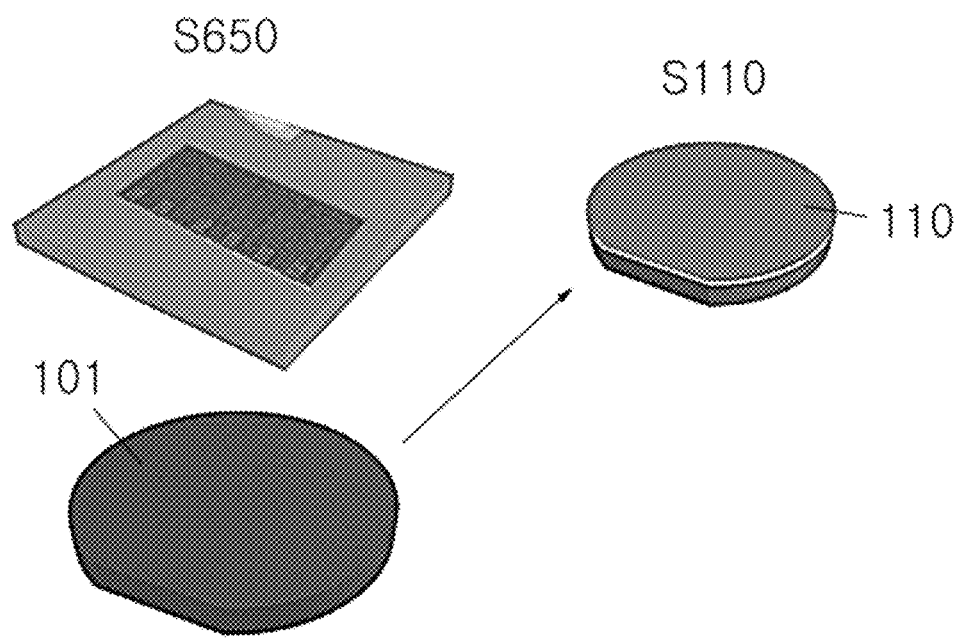

FIGS. 29A to 29O are schematic flowcharts of the method for fabricating a skin sensor device according to another aspect of the present disclosure. FIGS. 29A to 29O show the stack status for each process.

Referring to FIGS. 29A to 29I, the method for fabricating a skin sensor device includes: fabricating the sensor module 30; and bonding the sensor module 30 to the flexible patch 60.

The step of fabricating the sensor module 30 includes preparing a parent substrate 101 (S101) (FIG. 29A). The parent substrate 101 is made of a rigid material. Additionally, the parent substrate 101 may be a material having semiconductor properties. For example, the parent substrate may be made of a material including Si, but is not limited thereto. In an embodiment, the first substrate may be high-concentration doped Si (<0.01 Ωcm).

Referring to FIG. 29B, the step of fabricating the sensor module 30 includes: forming the first sacrificial layer 110 on the parent substrate 101 (S110).

The first sacrificial layer 110 is made of a material capable of separating an upper layer from the parent substrate 101 through an electrochemical lift-off process. For example, the first sacrificial layer 110 may be made of a material including at least one of Al, Cu, Fe or a combination thereof.

In an embodiment, the first sacrificial layer 110 may be a removable material by electrolytic etching. For example, the first sacrificial layer 110 may be made of a material including Al and/or Ti. The first sacrificial layer 110 may be an Al/Ti coating layer. Thus, a stack having the Al/Ti coating on the surface of the parent substrate 101 made of Si is obtained.

When the first sacrificial layer 110 includes a plurality of materials, each sacrificial material may be coated with different thicknesses. For example, the first sacrificial layer 110 may include a 200 nm thick Al layer and a 40 nm thick Ti layer.

Referring to FIG. 29C, the step of fabricating the sensor module 30 includes: forming the first passivation layer 200 on the first sacrificial layer 110 (S200).

The first passivation layer 200 is formed by a coating and/or curing process. A variety of spin coating techniques may be used to form the first passivation layer 200. The curing process for forming the first passivation layer 200 may be performed at 200° C. to 300° C., 240° C. to 260° C., for example, approximately 250° C. for 50 minutes to 70 minutes, for example, 1 hour. The thickness may be 2 um, but is not limited thereto.

Referring to FIG. 29D, the step of fabricating the sensor module 30 includes: forming the electronic circuit unit 300 (S300). In certain embodiments, the step S300 may include: forming the interconnect 301 (S301). Additionally, the step S300 may further include: building the temperature sensing unit 310 (S310); building the hydration sensing unit 320 (S320); building the photo sensing unit 330 (S330); and/or building the strain sensing unit 340 (S340).

In an embodiment, the step S301 of forming the interconnect 301 includes: depositing a material (for example, Au) for forming the interconnect 301 on the first passivation layer 200; and patterning the deposited interconnect 301 to form an auxetic hole pattern on the interconnect 301 at least in part.

The interconnect 301 may be deposited on a bottom PI 200, for example, by e-beam evaporation. The Au interconnect may be 100 nm in thickness.

The auxetic hole pattern may be patterned, for example, by a photoresist based lift-off process using LOR 3A, Microchem.

In an embodiment, the step S310 of building the temperature sensing unit 310 may include: forming the temperature responsive layer 317; and patterning the temperature responsive layer 317 to form the planar mesh structure of the auxetic hole pattern.

The temperature responsive layer 317 may be formed on the bottom PI layer 200, for example, by e-beam evaporation.

The auxetic hole pattern of the temperature responsive layer 317 may be formed through the lift-off process subsequent to the lift-off of the step S301.

The mesh structure of the auxetic hole pattern is formed as the temperature responsive layer 317 between the interconnects 301 by the e-beam evaporation deposition and the subsequent lift-off treatment. Part (for example, the edge) of the temperature responsive layer 317 and the adjacent interconnect 301 are connected to each other to complete the auxetic hole pattern. To this end, the same mask may be used in the patterning process.

In an embodiment, the step S320 of building the hydration sensing unit 320 may include: building at least one of the electrode 321 or the electrode 322; forming the hydration responsive layer 327 on the formed electrode 321 and/or 322; and patterning the hydration responsive layer 327 to form the planar mesh structure of the auxetic hole pattern.

In an embodiment, the at least one electrode 321 and at least one electrode 322 may be built. In this case, the plurality of electrodes 321, 322 may be arranged in an interdigitated array to implement a structure of interdigitated electrodes. The hydration responsive layer 327 is formed on the plurality of electrodes 321, 322 having the interdigitated electrodes shape. For example, the hydration responsive layer 327/the electrode 321 or 322 may be implemented as an Au/Cr (100 nm/1 nm) stack.

Referring to FIG. 29E, the step of fabricating the sensor module 30 includes: forming the second passivation layer 400 on the electronic circuit unit 300 (S400).

In an embodiment, some interfaces between the layers 200, 300, 400 may undergo chemical treatment to improve the interfacial strength. For example, some interfaces between the layers 200, 300, 400 may be treated with 1% v/v 3 APTES (aminopropyltriethoxysilane) in ionized water.

Additionally, referring to FIG. 29F, the step of fabricating the sensor module 30 includes: patterning the first passivation layer 200 and the second passivation layer 400 form the auxetic hole pattern (S500).

The top PI layer 400 is patterned by plasma treatment. For example, the top PI layer 400 may be patterned by oxygen plasma treatment using a hard mask made of Cu to form the auxetic hole pattern.

At the same time with the patterning of the top PI layer 400, the bottom PI layer 200 is also patterned.

When the surface of the top PI layer 400 is exposed to oxygen plasma, the exposed pattern area includes a pattern corresponding to the auxetic hole pattern of the electronic circuit unit 300 to form a perforated pattern. When the area exposed to oxygen plasma is patterned, an auxetic hole pattern including the pattern corresponding to the auxetic hole pattern of the electronic circuit unit 300 is formed on the top PI layer 400.

When the auxetic hole pattern of the top PI layer 400 is formed, the bottom PI layer 200 that directly contacts the top PI layer 400 in which the electronic circuit unit 300 is not built is automatically exposed to oxygen plasma. Meanwhile, since the electronic circuit unit 300 already has an auxetic hole pattern corresponding to the auxetic hole pattern of the top PI layer 400 at least in part, when the auxetic hole pattern of the top PI layer 400 is formed in the region in which the electronic circuit unit 300 is built, the bottom PI layer 200 is automatically exposed to oxygen plasma through the auxetic hole pattern of the electronic circuit unit 300. Thus, the bottom PI layer 200 has an auxetic hole pattern corresponding to the auxetic hole pattern of the top PI layer 400.

As each layer 200, 300, 400 of the sensor module 30 has the auxetic hole pattern at least in part and the shape of each auxetic hole pattern corresponds to each other, when each layer 200, 300, 400 is stacked through the steps 200 to S500, the sensor module 30 may have an auxetic perforated pattern in which perforations of open channels have a pattern of auxetic properties.

Additionally, in the step of fabricating the sensor module 30, each of the steps S200 to S400 may further include additionally forming an array hole. Additionally, the step of fabricating the sensor module 30 may further include: installing an alignment key in the array hole formed through patterning. As shown in the upper part of FIG. 2, the alignment key 500 of a cross shape is inserted to fix the alignment of the auxetic hole patterns for each layer 200, 300, 400 of the sensor module 30, thereby maintaining the open channels of the auxetic perforated pattern.

Figure 30A:
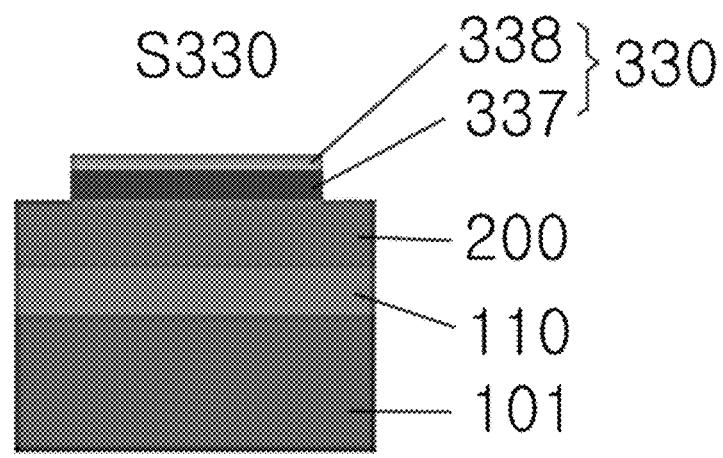
FIGS. 30A to 30C are schematic diagram of a process of fabricating a sensor module 30 including a photo sensing unit 330 according to an embodiment of the present disclosure.
Figure 30B:
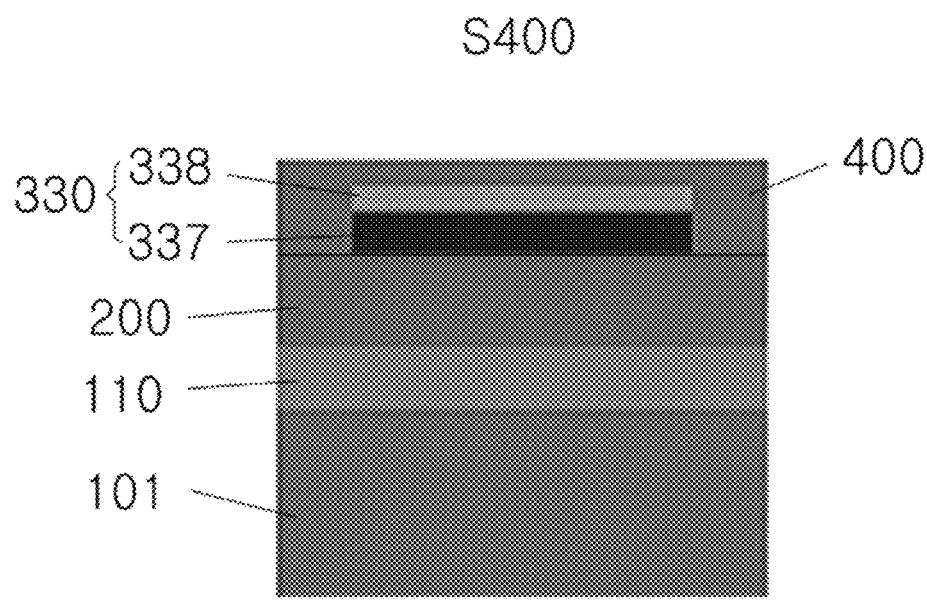
Figure 30C:
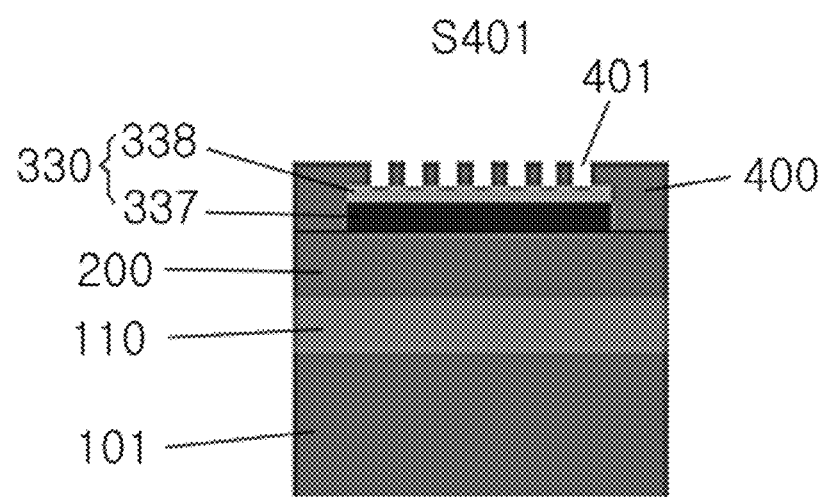

FIGS. 30A to 30C are schematic diagrams of a process of fabricating the sensor module 30 including the photo sensing unit 330 according to an embodiment of the present disclosure. The process of fabricating the sensor module 30 including the photo sensing unit 330 is similar to the process of fabricating the sensor module 30 including the other sensing unit (for example, 310, 320), and difference(s) will be described.

Referring to FIG. 30A, the step S330 of building the photo sensing unit 330 includes: forming the photo responsive layer 337 connected to the adjacent interconnect 301 on the first passivation layer 200 after the step S301 of building the adjacent interconnect 301. In some embodiments, the step S330 of building the photo sensing unit 330 may further include: forming the capping layer 338 on the photo responsive layer 337.

The adjacent interconnect 301 to which the photo responsive layer 337 is connected is formed on the first passivation layer 200, and when the adjacent interconnect 301 is projected toward the flexible patch 60, the projection area of the adjacent interconnect 301 may be disposed near the specific through-hole of the flexible patch 60. For example, the adjacent interconnect 301 may be positioned on two sides such that it is disposed between the specific through-holes of the flexible patch 60 in the stack structure of the skin sensor device 1.

In an embodiment, the photo responsive layer 337 may be formed such that two ends are positioned on the surface of the adjacent interconnect 301. The photo responsive layer 337 is built with a free-standing structure in the electrode part of the adjacent interconnect 301.

Subsequent to the step S330, in the same way as the other units 310, 320, as shown in FIG. 30B, the second passivation layer 400 may be formed on the photo sensing unit 330 (S400).

Referring to FIG. 30C, the step of fabricating the sensor module 30 may further include: after the steps S330 and S400, forming at least one auxiliary through-hole 401 in the sensing area of the photo sensing unit 330 in the second passivation layer 400 (S401). When there is no auxiliary through-hole 401, propagation of light or a specific band of light (for example, UV) to the photo responsive layer 337 may be blocked by the top PI layer 400, and thus light-induced electric current may not be generated. Additionally, the photo sensing unit 330 may be positioned on the flexible patch 60 in the opposite direction to the strain design to reduce strain dependency of the device conductance.

The second passivation layer 400 includes the auxiliary through-hole 401 formed by patterning the sensing area of the photo sensing unit 330 and the auxetic hole pattern formed by patterning part or all of the remaining area. Here, the remaining area is an area except the specific through-hole in which the photo sensing unit 330 is built.

Referring back to FIG. 29D, the step S340 of building the strain sensing unit 340 includes: forming the active layer 347 connected to the adjacent interconnect 301 on the first passivation layer 200 after the step S301 of building the adjacent interconnect 301.

The adjacent interconnect 301 to which the active layer 347 is connected is formed on the first passivation layer 200, and when the adjacent interconnect 301 is projected toward the flexible patch 60, the projection area of the adjacent interconnect 301 may be disposed near the specific through-hole of the flexible patch 60. For example, the adjacent interconnect 301 may be positioned on two sides such that it is disposed between the specific through-holes of the flexible patch 60 in the stack structure of the skin sensor device 1.

In an embodiment, the active layer 347 may be formed such that two ends are positioned on the surface of the adjacent interconnect 301. The active layer 347 is built with a free-standing structure in the electrode part of the adjacent interconnect 301.

The active layer 347 may be formed with the planar structure of FIG. 17 by deposition by radio frequency deposition and patterning. The active layer 347 may be made of polycrystalline ZnO. Thus, the deposition process for the ZnO thin film layer 347 may be performed at 150° C.-250° C., 180° C.-220° C., 200° C. The body of the active layer 347 is patterned using a chemical solution such as HCL solution.

In some embodiments, the step S340 of building the strain sensing unit 340 may further include: forming the bottom capping layer 346 that will be positioned at the interface between the active layer 347 and the first passivation layer 200; and/or forming the top capping layer 348 that will be positioned at the interface between the active layer 347 and the second passivation layer 400.

To make use of the piezoelectric effect of the strain sensing unit 340 having the ZnO layer, Schottky barrier may be formed by inserting a $HfO_2$ layer as the bottom capping layer 346 into ZnO/Au contact at 200-250° C., for example, approximately 225° C. by an atomic layer deposition process.

After the stack of the parent substrate 101, the first sacrificial layer 110 and the sensor module 30 is formed, the step of fabricating the skin sensor device 1 includes: bonding the sensor module 30 to the flexible patch 60.

Referring to FIG. 29G, the step of bonding the sensor module 30 to the flexible patch 60 includes: forming the second sacrificial layer 610 on one surface of the sensor module 30 (for example, one surface of the second passivation layer 400).

The second sacrificial layer 610 is made of a material that is different from the first sacrificial layer 110. The second sacrificial layer 610 is made of a material that is not removed in the process for removing the first sacrificial layer 110 (for example, an electrochemical lift-off process). The material of the second sacrificial layer 610 may be a material that is not affected by heat or decomposition. For example, the second sacrificial layer 610 may be made of a water-insoluble polymer (for example, PMMA, etc.), or any other water-insoluble material.

Referring to FIG. 29H, the step of bonding the sensor module 30 to the flexible patch 60 includes: attaching a transferor 630 to the second sacrificial layer 610 (S630). The transferor 630 may be a thermal release tape (TRT), but is not limited thereto. The transferor 630 may be transparent, but is not limited thereto.

Referring to FIG. 29I, the step of bonding the sensor module 30 to the flexible patch 60 includes: removing the first sacrificial layer 110 to separate the parent substrate 101 from the sensor module 30 (S650). The first sacrificial layer 110 may be removed by an electrochemical lift-off process. The first sacrificial layer 110 is electrolyzed in a salty solvent.

In an embodiment, to promote the decomposition of the first sacrificial layer 110, the solvent containing the stack of the step S101 to S630 may be heated (S650).

Additionally, the step of bonding the sensor module 30 to the flexible patch 60 includes: bonding the sensor module 30 separated from the parent substrate 101 to the flexible patch 60 (S670). The sensor module 30 is bonded to the flexible patch 60 by transferring part of the sensor module 30 (i.e., the first passivation layer 200) opposite the transferor 630 to the surface of the flexible patch 60 using the transferor 630.

In an embodiment, the sensor module 30 is bonded such that the auxetic hole pattern of the flexible patch 60 and the auxetic hole pattern of the sensor module 30 correspond to each other (S670). After the bonding, when the through-hole of the auxetic hole pattern of the flexible patch 60 and the through-hole of the auxetic hole pattern of the sensor module 30 are aligned to correspond to each other, a perforated pattern extending outward from the skin surface is formed in the skin sensor device 1.

In an embodiment, the flexible patch 60 may have an array hole corresponding to the array hole of the sensor module 30. These array holes may have a planar shape that matches the alignment key 500. After the bonding, the connection of the flexible patch 60 and the sensor module 30 may be fixed by the alignment key 500.

In alternative embodiments, the step of bonding the sensor module 30 to the flexible patch 60 may further include: before the step S670, fabricating the flexible patch 60 having the auxetic hole pattern using a mold substrate.

Referring to FIG. 29J, the step of fabricating the flexible patch 60 may include: coating a flexible material on the mold substrate 661 having a furrow pattern for forming the auxetic hole pattern to form the flexible patch 60 (S663).

An island step that protrudes from the surface of the mold substrate 661 in the furrow pattern of the mold substrate 661 matches the through-hole in the auxetic hole pattern of the flexible patch 60. As shown in FIG. 29J, each island step has a dumbbell plane or a circular plane that matches the through-hole that forms the auxetic hole pattern. A planar array of the island step of the mold substrate 661 matches the planar structure of the auxetic hole pattern formed by the dumbbell holes/circular hole that the flexible patch 60 will have.

In contrast, the furrow surrounded by the island step in the furrow pattern of the mold substrate 661 matches the planar shape of the sidewall that surrounds the through-hole in the auxetic hole pattern of the flexible patch 60.

The flexible material of which the flexible patch 60 is made is coated on the furrow of the mold substrate 661 and the internal space of the furrow is filled with the flexible material. As shown in FIG. 29J, the height of the filled flexible layer may be higher than the furrow height of the mold substrate 661.

In an embodiment, the flexible material may be coated to form the first flexible layer 61 and the second flexible layer 62 (S663).

Referring to FIG. 29K, the step of fabricating the flexible patch 60 may include: removing part or all of the flexible patch 60 present on top of the sidewall (i.e., the island step) that form the furrow (S665).

The flexible patch 60 beyond the furrow (i.e., formed at a higher position than the sidewall of the furrow of the mold substrate 661) is removed at least in part to expose part or all of the sidewall surface on top of the sidewall through the flexible patch 60 (S665).

In an embodiment, all or part of the flexible patch 60 present on top in an uncured state may be removed.

The part beyond the furrow is removed by contacting a board (not shown) with the flexible patch layer beyond the sidewall of the furrow of the mold and rubbing the board (not shown) and/or the flexible patch 60 (a cast-mold structure) (S665). The board plays a role of a plastering board that pushes the excessive flexible material to remove it.

Referring to FIG. 29L, the step of bonding the sensor module 30 to the flexible patch 60 may include: after the step S665, arranging the sensor module 30 adhered with the transferor 630 on the surface of the flexible patch 60 formed on the mold substrate 661 such that the through-hole of the auxetic hole pattern of the flexible patch 60 and the through-hole of the auxetic hole pattern of the sensor module 30 correspond to each other (S667). For example, the sensor module 30 and the flexible patch 60 may be bonded such that each island step of the mold substrate 661 corresponds to each through-hole of the sensor module 30.

Figure 31A:
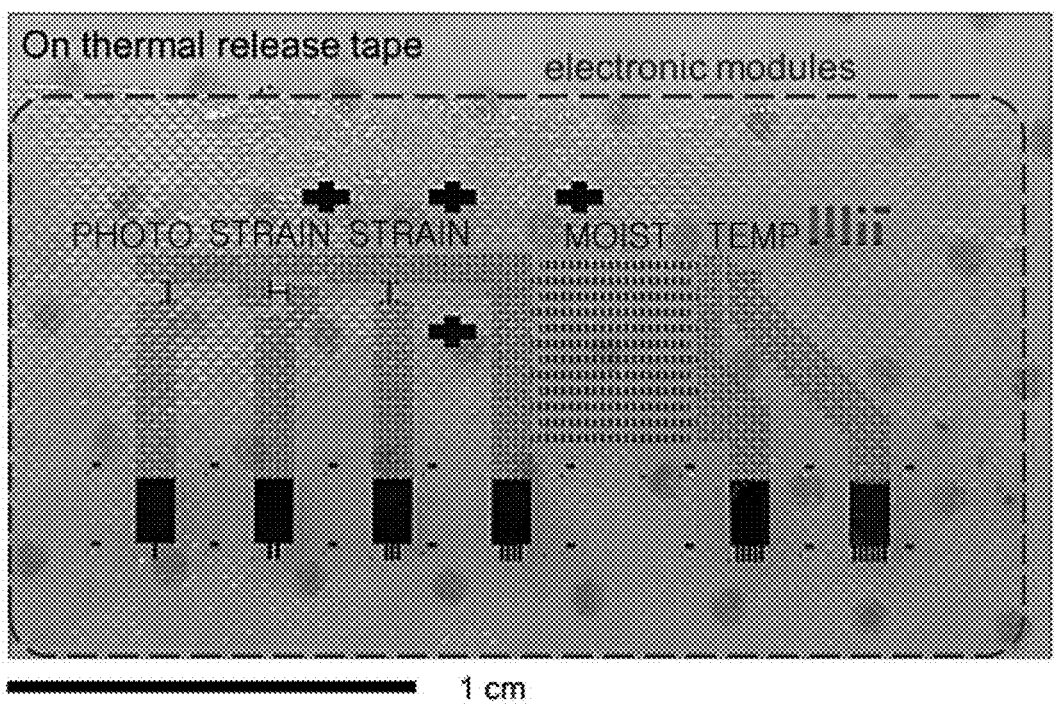
FIGS. 31A to 31D are plan views of a sensor module transferred after attached to a thermal release tape (TRT).
Figure 31B:
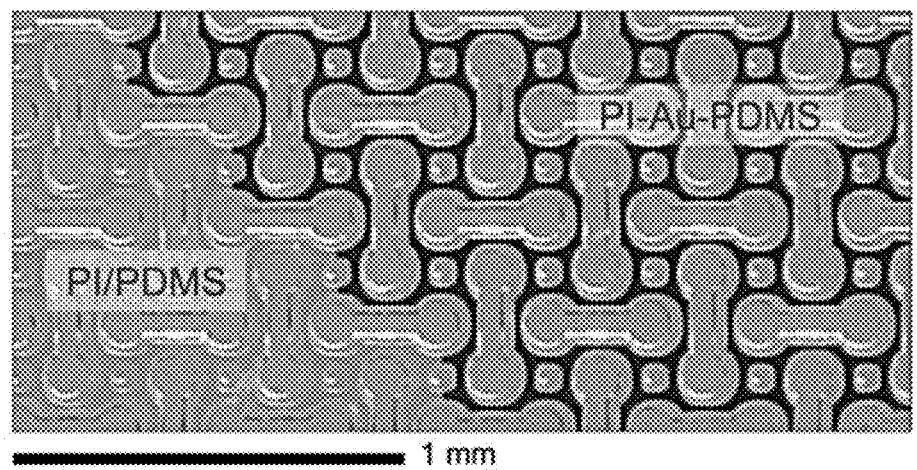
Figure 31C:
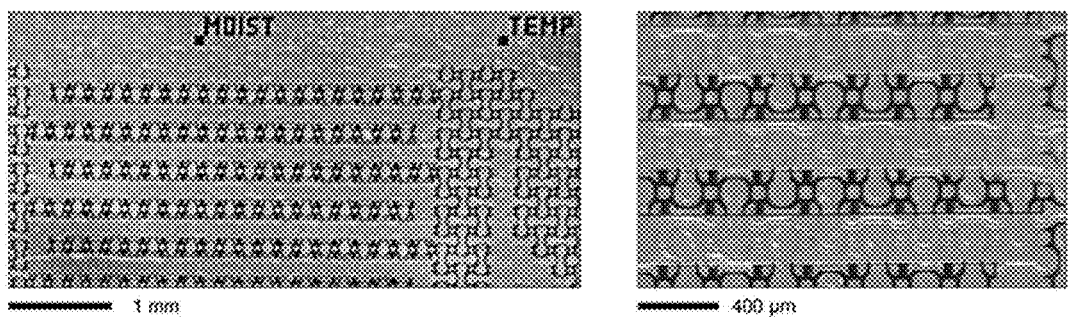
Figure 31D:
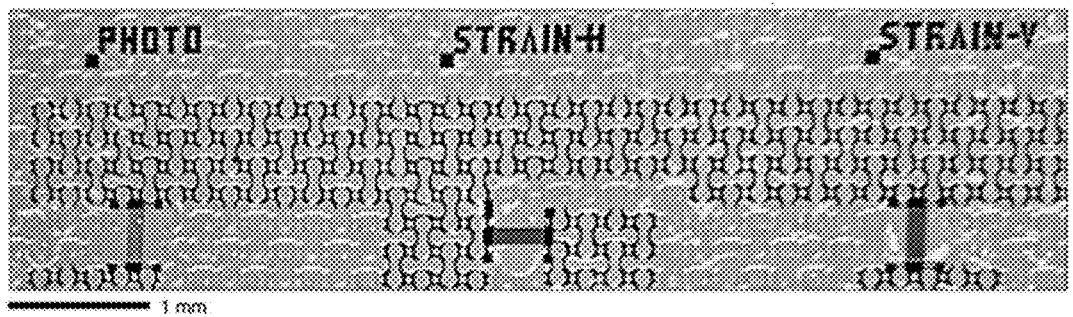

FIGS. 31A to 31D are plan views of the sensor module transferred after attached to the TRT 630. FIGS. 31B to 31D are partial enlarged views of FIG. 31A.

As shown in FIG. 31, the sensor module 30 of the structure of the sensor module 30; the flexible patch 60; and the second sacrificial layer 610 and the transferor 630 are bonded to the surface of the flexible patch 60 of FIG. 29K through the transferor 630 (S667).

The sidewall part of the furrow of the mold substrate 661 that matches the through-hole of the flexible patch 60 is arranged to correspond to the through-hole of the sensor module 30 (S667).

In an embodiment, the step S667 of arranging may include compressing the arranged sensor module 30 with the flexible patch 60.

Referring to FIG. 29M, the step of bonding the sensor module 30 to the flexible patch 60 may include: separating the flexible patch 60 bonded with the sensor module 30 from the mold substrate 661 (S669). The structure of the sensor module 30; the flexible patch 60; the second sacrificial layer 610 and the transferor 630 is separated from the mold substrate 661 through the transferor 630.

Referring to FIG. 29N, the step S670 of bonding the sensor module 30 separated from the parent substrate 101 to the flexible patch 60 may include separating the transferor 630 from the structure of the sensor module 30; the flexible patch 60; the second sacrificial layer 610 and the transferor 630; and removing the second sacrificial layer 610.

For example, when the transferor 630 is a TRT, the TRT 630 may be separated by heating the structure at approximately 150° C.

The second sacrificial layer 610 may be removed by chemical etching. The second sacrificial layer 610 is a water-insoluble material. The remaining structure including the second sacrificial layer 610 may be dipped into an etching solution (for example, acetone) to remove the second sacrificial layer 610 (for example, PMMA). When the PMMA layer 610 dissolves, the skin-attachable skin sensor device 1 having a perforated pattern is fabricated.

In an embodiment, the step S670 may further include: cleaning off the etching solution residue or the surface residue from the structure of the skin sensor device 1 free of the second sacrificial layer.

For example, acetone remaining on the surface of the sensor module 30 (for example, the second passivation layer 400) from which the second sacrificial layer 610 is peeled using cellulose wipers (TX2009, Texwipe) may be cleaned off with isopropanol.

The separated parent substrate 101 may be reused to fabricate other sensor module 30.

Referring to FIG. 29O, the parent substrate 101 separated in the step S650 may be used to fabricate other sensor module 30. There is no need to prepare a separate parent substrate 101 to fabricate other sensor module 30. As a result, it is possible to minimize economic ad physical resources for fabricating the skin sensor device 1.

While the present disclosure has been hereinabove described with reference to the embodiments shown in the drawings, this is provided by way of illustration and those skilled in the art will understand that a variety of modifications and variations may be made thereto. However, it should be noted that such modifications fall in the technical protection scope of the present disclosure. Accordingly, the true technical protection scope of the present disclosure should be defined by the technical spirit of the appended claims.

DETAILED DESCRIPTION OF MAIN ELEMENTS

1: Non-invasive electronic device
30: Electronic module
60: Flexible patch
101: Parent substrate
110: First sacrificial layer
200, 400: Passivation layer
300: Electronic circuit unit
310: Temperature sensing unit
320: Hydration sensing unit
330: Photo sensing unit
340: Strain sensing unit

The invention claimed is:

1. An electronic module for monitoring a skin condition, comprising:
   a first passivation layer configured to be positioned closer to a skin surface;
   an electronic circuit unit built on the first passivation layer, and including a plurality of interconnects made of a conductive material and at least one sensing unit including a semiconductor property material, wherein each sensing unit includes at least one type of sensing unit selected from the group consisting of: one or more temperature sensing units, one or more hydration sensing units, one or more photo sensing units, and one or more strain sensing units; and
   a second passivation layer formed on the electronic circuit unit,
   wherein each of the first passivation layer, the electronic circuit unit and the second passivation layer includes a plurality of through-holes, wherein at least some of the plurality of through-holes in each layer form respective hole patterns, and
   wherein the respective hole patterns in the first passivation layer, the electronic circuit unit and the second passivation layer have corresponding planar patterns that align to form a continuous open channel when the first passivation layer, the electronic circuit unit and the second passivation layer are stacked.

2. The electronic module according to claim 1, wherein the plurality of through-holes forming the respective hole patterns comprise a plurality of dumbbell through-holes,
   wherein each dumbbell through-hole includes circular parts at two ends connected by an extended part, and
   wherein the plurality of dumbbell through-holes are arranged in an interdigitated array such that a circular part of one dumbbell through-hole is adjacent to an extended part of a neighboring dumbbell through-hole.

3. The electronic module according to claim 2, wherein each respective hole pattern further comprises a plurality of circular through-holes, and
   wherein the circular through-holes are formed in regions surrounded by the dumbbell through-holes arranged in the interdigitated array.

4. The electronic module according to claim 1, wherein of the respective hole patterns in the first passivation layer, the electronic circuit unit and the hole pattern of the second passivation layer are configured with different specifications to provide varying degrees of flexibility.

5. The electronic module according to claim 1, wherein each temperature sensing unit includes:
   a temperature responsive layer connected to a corresponding interconnect among the plurality of interconnects,
   wherein the temperature responsive layer generates an electric current in response to temperature, and
   wherein the temperature responsive layer is connected to be positioned on a same plane as the corresponding interconnect.

6. The electronic module according to claim 5, wherein the temperature responsive layer includes through-holes forming a hole pattern partially corresponding to the respective hole patterns in the first passivation layer and the second passivation layer.

7. The electronic module according to claim 1, wherein each hydration sensing unit includes:
   a plurality of electrodes connected to a corresponding interconnect among the plurality of interconnects, wherein the plurality of electrodes include at least one first electrode and at least one second electrode; and
   a hydration responsive layer formed on a surface of the plurality of electrodes,
   wherein each of the plurality of electrodes and the hydration responsive layer includes through-holes that form an open channel when stacked upon each other, and
   wherein the through-holes of the plurality of electrodes and the through-holes of the hydration responsive layer have a planar pattern corresponding to the planar patterns of the through-holes in the first passivation layer and the second passivation layer.

8. The electronic module according to claim 7, wherein the each hydration sensing unit has a cantilever structure such that the first electrode extends from a first interconnect, and the second electrode extends from a second interconnect, and
   wherein extended parts of the at least one first electrode and the at least one second electrode are arranged in an interdigitated array.

9. The electronic module according to claim 1, wherein each photo sensing unit includes:
   a photo responsive layer having two ends positioned on a surface of a corresponding interconnect among the plurality of interconnects,
   wherein the photo responsive layer generates an electric current in response to light irradiation, and
   wherein the photo responsive layer generates an electric current when a specific band of light is irradiated, or generates a different electric current when an intensity of the irradiated light changes.

10. The electronic module according to claim 9, wherein a part of the second passivation layer formed at a sensing area of each photo sensing unit further includes at least one auxiliary through-hole.

11. The electronic module according to claim 10, wherein each photo sensing unit further includes a capping layer formed at an interface between the part of the second passivation layer having the auxiliary through-hole and the photo sensing unit.

12. The electronic module according to claim 1, wherein the each strain sensing unit includes:
an active layer having two ends positioned on a surface of a corresponding interconnect among the plurality of interconnects, wherein the active layer generates an electric current in response to strain of the electronic module.

13. The electronic module according to claim 12, wherein the strain sensing unit further includes at least one of a first capping layer formed at an interface between the active layer and the first passivation layer, or a second capping layer formed at an interface between the active layer and the second passivation layer.

14. The electronic module according to claim 12, wherein the electronic circuit unit includes a pair of the strain sensing units,
wherein a first strain sensing unit of the pair is positioned on the first passivation layer to sense x-axial strain, and
wherein a second strain sensing unit of the pair is positioned on the first passivation layer to sense y-axial strain.

15. A non-invasive electronic device comprising the electronic module of claim 1, wherein the non-invasive electronic device comprises:
a skin attachable flexible patch configured to contact the first passivation layer,
wherein the flexible patch includes a plurality of through-holes, wherein at least some of the plurality of through-holes of the flexible patch form a patch hole pattern, and
wherein the patch hole pattern has a planar pattern corresponding to the respective hole patterns of the electronic module to form a perforated pattern when stacked with the electronic module.

16. The non-invasive electronic device according to claim 15, wherein the plurality of through-holes of the flexible patch includes at least one specific through-hole that is different from other through-holes,
wherein a size of the specific through-hole is different from a size of the other through-holes of the electronic module, and
wherein one of the photo sensing units and one of the strain sensing units are built in the specific through-hole.

17. The non-invasive electronic device according to claim 16, wherein the flexible patch further includes a supporter which extends from one side to an opposing side in the at least one specific through-hole to support the photo sensing unit.

* * * * *